«12» United States Patent
Zariri et al.

(10) Patent No.: US 11,292,808 B2
(45) Date of Patent: Apr. 5, 2022

(54) MODIFIED HEXA-ACYLATED NEISSERIAL LPS

(71) Applicant: De Staat der Nederlanden, vert. door de minister van VWS, Ministerie van Volksgezondheid, Welzijn en Sport, The Hague (NL)

(72) Inventors: Afshin Zariri, Uithoorn (NL); Elder Pupo Escalona, Amersfoort (NL); Peter André Van Der Ley, Utrecht (NL)

(73) Assignee: Intravacc B.V., Bilthoven (NL)

( * ) Notice: Subject to any disclaimer, the term of this patent is extended or adjusted under 35 U.S.C. 154(b) by 113 days.

(21) Appl. No.: 16/072,895

(22) PCT Filed: Jan. 27, 2017

(86) PCT No.: PCT/EP2017/051801
§ 371 (c)(1),
(2) Date: Jul. 26, 2018

(87) PCT Pub. No.: WO2017/129761
PCT Pub. Date: Aug. 3, 2017

(65) Prior Publication Data
US 2019/0031700 A1      Jan. 31, 2019

(30) Foreign Application Priority Data

Jan. 28, 2016   (NL) ..................................... 2016170

(51) Int. Cl.
| | |
|---|---|
| *C07H 15/06* | (2006.01) |
| *C12N 1/20* | (2006.01) |
| *A61K 39/095* | (2006.01) |
| *A61P 31/04* | (2006.01) |
| *A61K 31/7024* | (2006.01) |
| *C12R 1/36* | (2006.01) |

(52) U.S. Cl.
CPC ......... *C07H 15/06* (2013.01); *A61K 31/7024* (2013.01); *A61K 39/095* (2013.01); *A61P 31/04* (2018.01); *C12N 1/205* (2021.05); *C12R 2001/36* (2021.05)

(58) Field of Classification Search
None
See application file for complete search history.

(56) References Cited

FOREIGN PATENT DOCUMENTS

| | | |
|---|---|---|
| WO | WO00/26384 A1 | 5/2000 |
| WO | WO2014/138696 A1 | 9/2014 |

OTHER PUBLICATIONS

Pupo et al (Journal of Biological Chemistry, 289(12):8668-8680, 2014).*

Montminy Sara W et al: Virulence factors of Yersinia pestis are overcome by a strong lipopolysaccharide response, Nature Immunology, Nature Publishing Group, GB, vol. 7, No. 10,pp. 1066-1073.

M G Sunshine et al: Mutation of the htrB gene in a virulent *Salmonella typhimurium* strain by intergeneric transduction: strain construction and phenotypic characterization, Journal of Bacteriology, Sep. 1, 1997 (Sep. 1, 1997), pp. 5521-5533.

E. Pupo et al: "Lipopolysaccharide Engineering in Neisseria meningitidis: Structural Analysis of Different Pentaacyl Lipid A Mutants and Comparison of Their Modified Agonist Properties", Journal of Biological Chemistry, vol. 289, No. 12, Mar. 21, 2014, pp. 8668-8680.

Zughaier et al (2007) Physicochemical characterization and biological activity of lipooligosaccharides and lipid A from Neisseria meningitidis. Journal of endotoxin research 13, 343-357.

Van Der Ley et al (2001) Modification of lipid A biosynthesis in Neisseria meningitidis lpxL mutants: influence on lipopolysaccharide structure, toxicity, and adjuvant activity. Infection and immunity 69, 5981-5990.

Van De Waterbeemd (2010) Improved OMV vaccine against Neisseria meningitidis using genetically engineered strains and a detergent-free purification process. Vaccine 28, 4810-4816.

Steeghs, L., et al (2008) Differential activation of human and mouse Toll-like receptor 4 by the adjuvant candidate LpxL 1 of Neisseria meningitidis. Infection and immunity 76, 3801-3807.

Carty S. M., et al (1999) Effect of cold shock on lipid A biosynthesis in *Escherichia coli*. Induction at 12 degrees C of an acyltransferase specific for palmitoleoyl-acyl carrier protein. The Journal of biological chemistry 274, 9677-9685.

* cited by examiner

*Primary Examiner* — Patricia Duffy
(74) *Attorney, Agent, or Firm* — N.V. Nederlandsch Octrooibureau

(57) ABSTRACT

The present invention relates to neisserial LPS having a hexa-acylated lipid A moiety, wherein the hexa-acylated lipid A moiety is modified as compared to the lipid A moiety of a wild-type neisserial LPS in that it comprises a palmitoleoyl instead of a lauroyl secondary acyl chain on the glucosamine at the non-reducing end of the lipid A moiety. The invention further relates to mixtures of the hexa-acylated LPS with the corresponding penta-acylated LPS, lacking a secondary acyl chain on the glucosamine at the non-reducing end of the lipid A moiety. The invention also relates to neisserial bacteria that have been genetically modified to reduce expression of the endogenous lpxL1 gene and to introduce expression of a heterologous thermosensitive lpxP gene for producing the hexa- and penta-acylated LPS. By selecting the time and/or temperature at which the bacterium is grown, it is feasible to increase or decrease the amount of hexa-acylated lipid A structure relative to the corresponding penta-acylated structure and thereby modulate the TLR4 agonist activity of the neisserial LPS of the invention, to the exact level of activity required for a particular immunotherapeutic approach.

20 Claims, 10 Drawing Sheets
Specification includes a Sequence Listing.

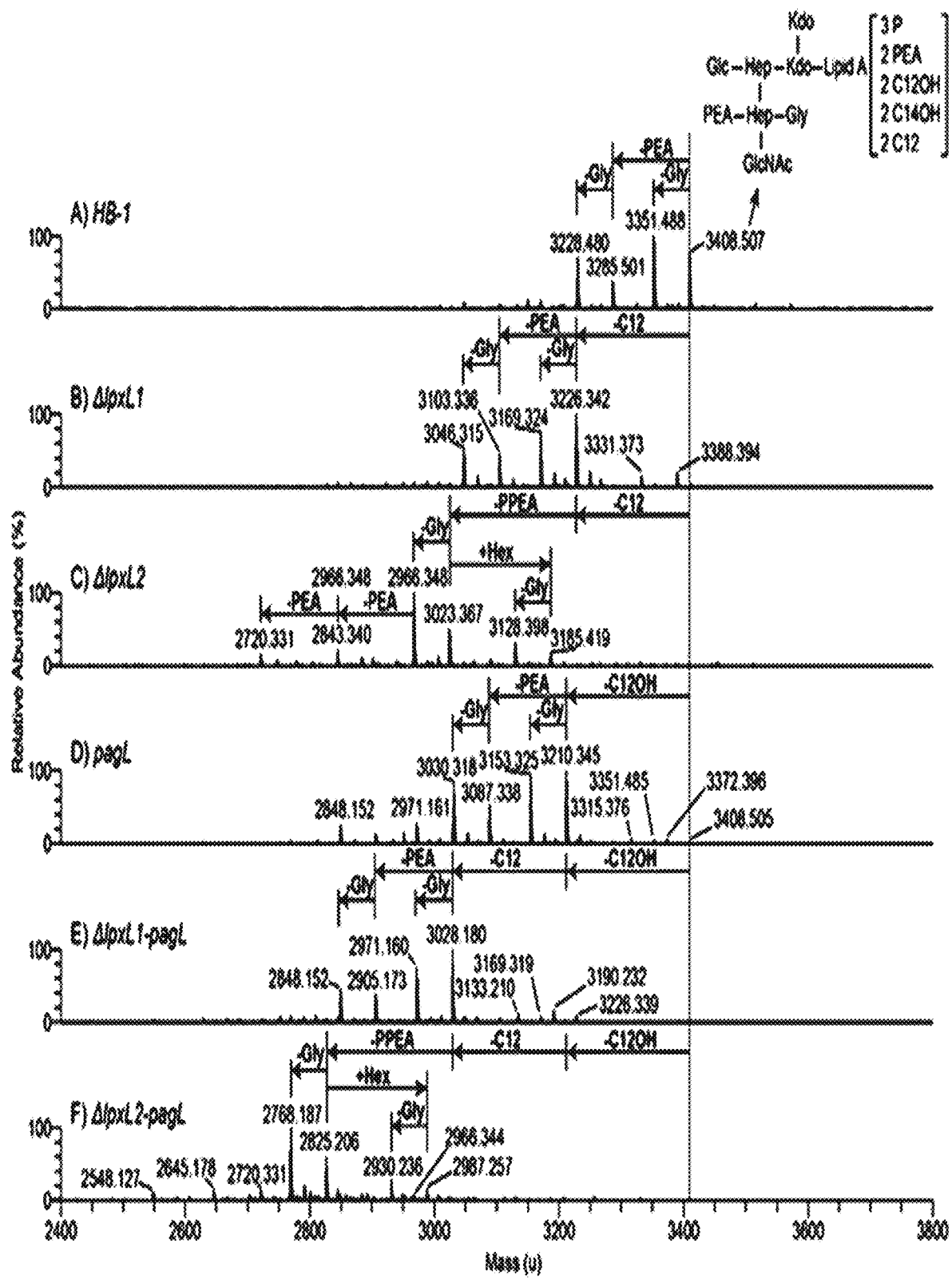
Fig. 1A-F

Fig. 1G-L
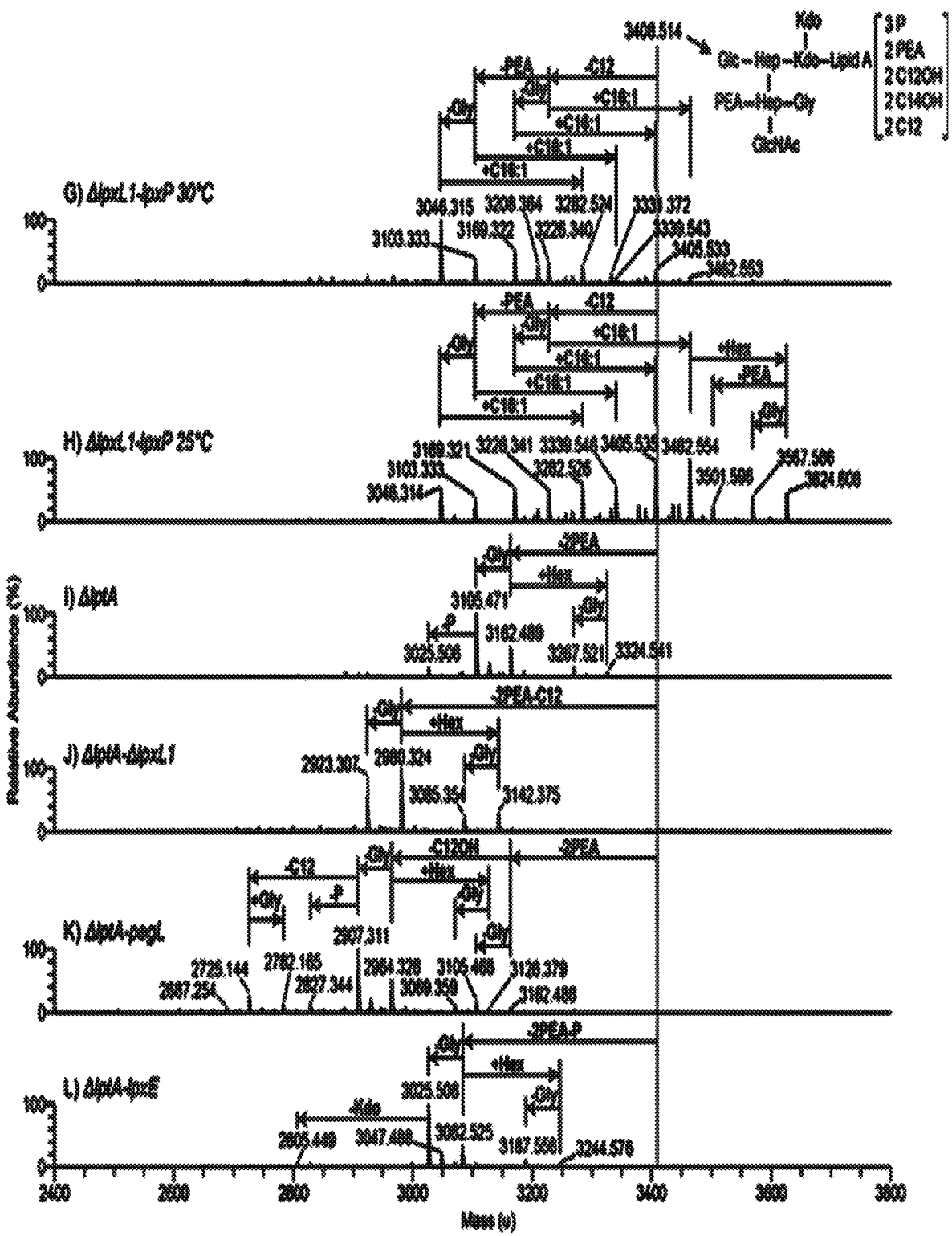

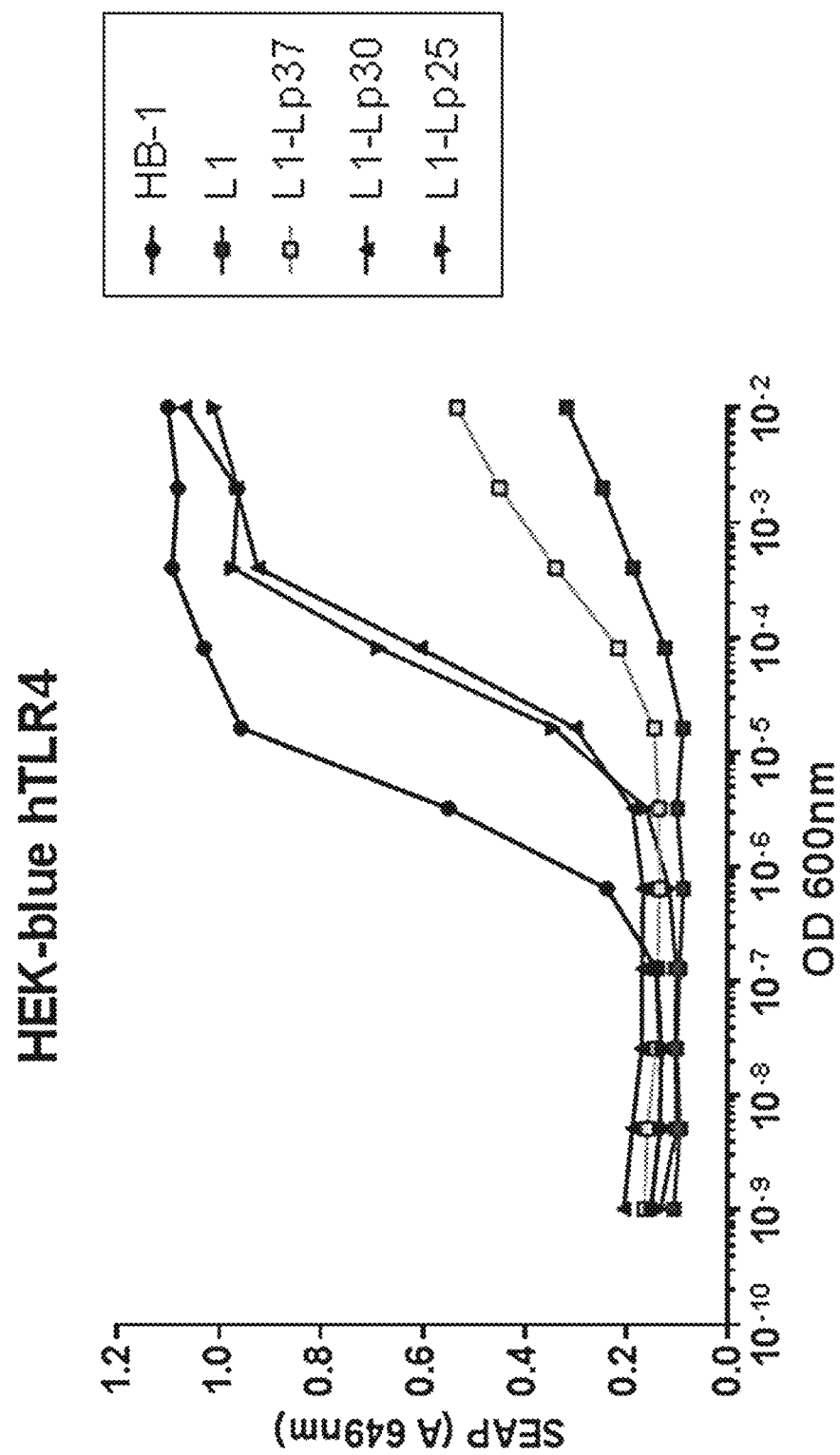

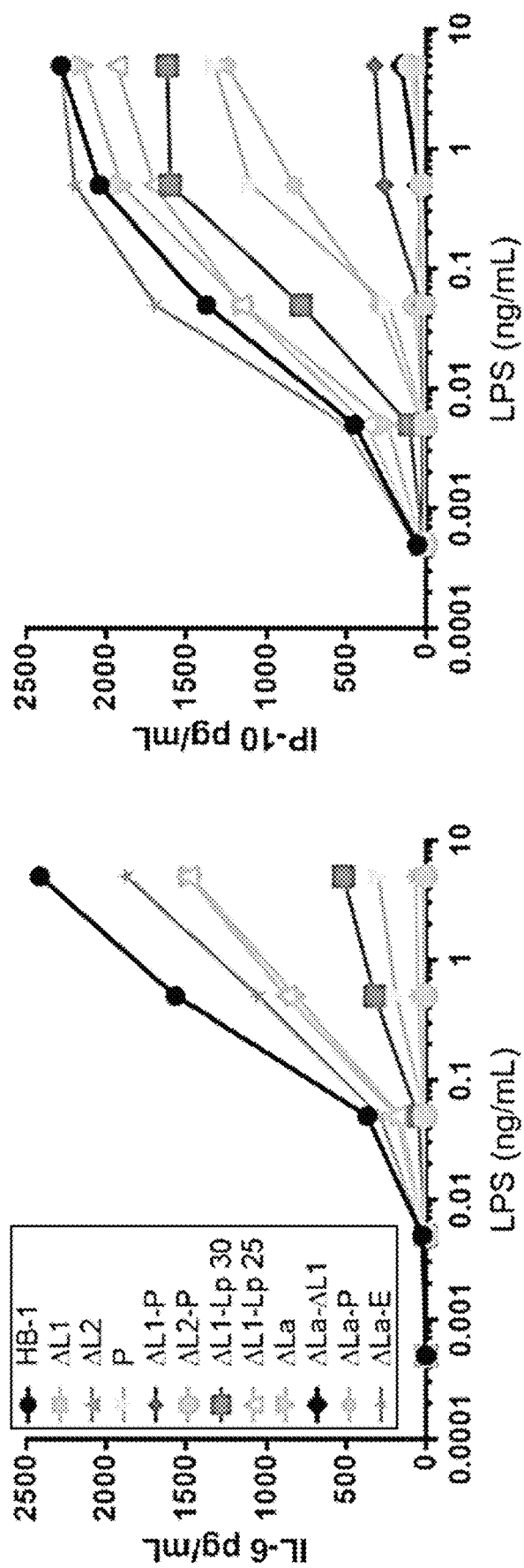

SEQUENCE LISTING

```
<160> NUMBER OF SEQ ID NOS: 22

<210> SEQ ID NO 1
<211> LENGTH: 299
<212> TYPE: PRT
<213> ORGANISM: Neisseria meningitidis

<400> SEQUENCE: 1

Met Pro Ser Glu Lys Lys Met Cys Ile Glu Met Lys Phe Ile Phe Phe
1               5                   10                  15

Val Leu Tyr Val Leu Gln Phe Leu Pro Phe Ala Leu Leu His Lys Ile
            20                  25                  30
```

```
Ala Asp Leu Thr Gly Leu Leu Ala Tyr Leu Leu Val Lys Pro Arg Arg
         35                  40                  45

Arg Ile Gly Glu Ile Asn Leu Ala Lys Cys Phe Ser Glu Trp Ser Glu
 50                  55                  60

Glu Lys Arg Lys Thr Val Leu Lys Gln His Phe Lys His Met Ala Lys
 65                  70                  75                  80

Leu Met Leu Glu Tyr Gly Leu Tyr Trp Tyr Ala Pro Ala Gly Arg Leu
                 85                  90                  95

Lys Ser Leu Val Arg Tyr Arg Asn Lys His Tyr Leu Asp Asp Ala Leu
                100                 105                 110

Ala Ala Gly Glu Lys Val Ile Ile Leu Tyr Pro His Phe Thr Ala Phe
            115                 120                 125

Glu Met Ala Val Tyr Ala Leu Asn Gln Asp Ile Pro Leu Ile Ser Met
130                 135                 140

Tyr Ser His Gln Lys Asn Lys Ile Leu Asp Glu Gln Ile Leu Lys Gly
145                 150                 155                 160

Arg Asn Arg Tyr His Asn Val Phe Leu Ile Gly Arg Thr Glu Gly Leu
                165                 170                 175

Arg Ala Leu Val Lys Gln Phe Arg Lys Ser Ser Ala Pro Phe Leu Tyr
            180                 185                 190

Leu Pro Asp Gln Asp Phe Gly Arg Asn Asp Ser Val Phe Val Asp Phe
        195                 200                 205

Phe Gly Ile Gln Thr Ala Thr Ile Thr Gly Leu Ser Arg Ile Ala Ala
210                 215                 220

Leu Ala Asn Ala Lys Val Ile Pro Ala Ile Pro Val Arg Glu Ala Asp
225                 230                 235                 240

Asn Thr Val Thr Leu His Phe Tyr Pro Ala Trp Lys Ser Phe Pro Gly
                245                 250                 255

Glu Asp Ala Lys Ala Asp Ala Gln Arg Met Asn Arg Phe Ile Glu Asp
            260                 265                 270

Arg Val Arg Glu His Pro Glu Gln Tyr Phe Trp Leu His Lys Arg Phe
        275                 280                 285

Lys Thr Arg Pro Glu Gly Ser Pro Asp Phe Tyr
        290                 295
```

<210> SEQ ID NO 2
<211> LENGTH: 293
<212> TYPE: PRT
<213> ORGANISM: Neisseria gonorrhoeae

<400> SEQUENCE: 2

```
Met Cys Thr Glu Met Lys Phe Ile Phe Phe Val Leu Tyr Val Leu Gln
 1               5                  10                  15

Phe Leu Pro Phe Ala Leu Leu His Lys Ile Ala Gly Leu Ile Gly Ser
                 20                  25                  30

Leu Ala Tyr Leu Leu Val Lys Pro Arg Arg Ile Gly Glu Ile Asn
         35                  40                  45

Leu Ala Lys Cys Phe Pro Glu Trp Asp Glu Glu Lys Arg Lys Thr Val
 50                  55                  60

Leu Lys Gln His Phe Lys His Met Ala Lys Leu Met Leu Glu Tyr Gly
 65                  70                  75                  80

Leu Tyr Trp Tyr Ala Pro Ala Lys Cys Leu Lys Ser Met Val Arg Tyr
                 85                  90                  95

Arg Asn Lys His Tyr Leu Asp Asp Ala Leu Ala Ala Gly Glu Lys Val
                100                 105                 110
```

```
Ile Ile Leu Tyr Pro His Phe Thr Ala Phe Glu Met Ala Val Tyr Ala
            115                 120                 125

Leu Asn Gln Asp Val Pro Leu Ile Ser Met Tyr Ser His Gln Lys Asn
    130                 135                 140

Lys Ile Leu Asp Glu Gln Ile Leu Lys Gly Arg Asn Arg Tyr His Asn
145                 150                 155                 160

Val Phe Leu Ile Gly Arg Thr Glu Gly Leu Arg Ala Leu Val Lys Gln
                165                 170                 175

Phe Arg Lys Ser Ser Ala Pro Phe Leu Tyr Leu Pro Asp Gln Asp Phe
                180                 185                 190

Gly Arg Asn Asn Ser Val Phe Val Asp Phe Gly Ile Gln Thr Ala
                195                 200                 205

Thr Ile Thr Gly Leu Ser Arg Ile Ala Ala Leu Ala Asn Ala Lys Val
    210                 215                 220

Ile Pro Ala Ile Pro Val Arg Glu Ala Asp Asn Thr Val Thr Leu Gln
225                 230                 235                 240

Phe Tyr Pro Ala Trp Lys Ser Phe Pro Ser Glu Asp Ala Gln Ala Asp
                245                 250                 255

Ala Gln Arg Met Asn Arg Phe Ile Glu Glu Arg Val Arg Glu His Pro
                260                 265                 270

Glu Gln Tyr Phe Trp Leu His Lys Arg Phe Lys Thr Arg Pro Glu Gly
            275                 280                 285

Ser Pro Asp Phe Tyr
            290

<210> SEQ ID NO 3
<211> LENGTH: 296
<212> TYPE: PRT
<213> ORGANISM: Neisseria lactamica

<400> SEQUENCE: 3

Met Lys Phe Ile Phe Phe Val Leu Tyr Val Gln Phe Leu Pro Phe
1               5                   10                  15

Ala Leu Leu His Lys Leu Ala Asp Leu Thr Gly Leu Leu Ala Tyr Leu
                20                  25                  30

Leu Val Lys Pro Arg Arg Ile Gly Glu Ile Asn Leu Ala Lys Cys
            35                  40                  45

Phe Pro Glu Trp Asp Gly Lys Lys Arg Glu Thr Val Leu Lys Gln His
    50                  55                  60

Phe Lys His Met Ala Lys Leu Met Leu Glu Tyr Gly Leu Tyr Trp Tyr
65                  70                  75                  80

Ala Pro Ala Gly Arg Leu Lys Ser Leu Val Arg Tyr Arg Asn Lys His
                85                  90                  95

Tyr Leu Asp Asp Ala Leu Ala Ala Gly Glu Lys Val Ile Ile Leu Tyr
            100                 105                 110

Pro His Phe Ile Ala Phe Glu Met Ala Val Tyr Ala Leu Asn Gln Asp
            115                 120                 125

Val Pro Leu Ile Ser Met Tyr Ser His Gln Lys Asn Lys Met Leu Asp
    130                 135                 140

Glu Gln Ile Leu Lys Gly Arg Asn Arg Tyr His Asn Val Phe Leu Ile
145                 150                 155                 160

Gly Arg Thr Glu Gly Leu Arg Ala Leu Val Lys Gln Phe Arg Lys Ser
                165                 170                 175

Ser Ala Pro Phe Leu Tyr Leu Pro Asp Gln Asp Phe Gly Arg Asn Asp
                180                 185                 190
```

Ser Val Phe Val Asp Phe Phe Gly Ile Arg Thr Ala Thr Ile Thr Gly
                195                 200                 205

Leu Ser Arg Ile Ala Ala Leu Ala Asn Ala Lys Val Ile Pro Ala Ile
    210                 215                 220

Pro Val Arg Glu Ala Asp Asn Thr Val Thr Leu His Phe Tyr Pro Ala
225                 230                 235                 240

Trp Glu Ser Phe Pro Ser Glu Asp Ala Lys Ala Asp Ala Gln Arg Met
                245                 250                 255

Asn Arg Phe Ile Glu Glu Arg Val Arg Glu His Pro Glu Gln Tyr Phe
                260                 265                 270

Trp Leu His Lys Arg Phe Lys Thr Arg Pro Glu Gly Ser Pro Asp Phe
            275                 280                 285

Tyr Gly Leu His Glu Val Thr Lys
            290                 295

<210> SEQ ID NO 4
<211> LENGTH: 306
<212> TYPE: PRT
<213> ORGANISM: Escherichia coli

<400> SEQUENCE: 4

Met Phe Pro Gln Cys Lys Phe Ser Arg Glu Phe Leu His Pro Arg Tyr
1               5                   10                  15

Trp Leu Thr Trp Phe Gly Leu Gly Val Leu Trp Leu Trp Val Gln Leu
                20                  25                  30

Pro Tyr Pro Val Leu Cys Phe Leu Gly Thr Arg Ile Gly Ala Met Ala
            35                  40                  45

Arg Pro Phe Leu Lys Arg Arg Glu Ser Ile Ala Arg Lys Asn Leu Glu
50                  55                  60

Leu Cys Phe Pro Gln His Ser Ala Glu Arg Glu Lys Met Ile Ala
65                  70                  75                  80

Glu Asn Phe Arg Ser Leu Gly Met Ala Leu Val Glu Thr Gly Met Ala
                85                  90                  95

Trp Phe Trp Pro Asp Ser Arg Val Arg Lys Trp Phe Asp Val Glu Gly
                100                 105                 110

Leu Asp Asn Leu Lys Arg Ala Gln Met Gln Asn Arg Gly Val Met Val
            115                 120                 125

Val Gly Val His Phe Met Ser Leu Glu Leu Gly Gly Arg Val Met Gly
            130                 135                 140

Leu Cys Gln Pro Met Met Ala Thr Tyr Arg Pro His Asn Asn Gln Leu
145                 150                 155                 160

Met Glu Trp Val Gln Thr Arg Gly Arg Met Arg Ser Asn Lys Ala Met
                165                 170                 175

Ile Gly Arg Asn Asn Leu Arg Gly Ile Val Gly Ala Leu Lys Lys Gly
            180                 185                 190

Glu Ala Val Trp Phe Ala Pro Asp Gln Asp Tyr Gly Arg Lys Gly Ser
            195                 200                 205

Ser Phe Ala Pro Phe Phe Ala Val Glu Asn Val Ala Thr Thr Asn Gly
    210                 215                 220

Thr Tyr Val Leu Ser Arg Leu Ser Gly Ala Ala Met Leu Thr Val Thr
225                 230                 235                 240

Met Val Arg Lys Ala Asp Tyr Ser Gly Tyr Arg Leu Phe Ile Thr Pro
                245                 250                 255

Glu Met Glu Gly Tyr Pro Thr Asp Glu Asn Gln Ala Ala Ala Tyr Met
                260                 265                 270

```
Asn Lys Ile Ile Glu Lys Glu Ile Met Arg Ala Pro Glu Gln Tyr Leu
            275                 280                 285

Trp Ile His Arg Arg Phe Lys Thr Arg Pro Val Gly Glu Ser Ser Leu
        290                 295                 300

Tyr Ile
305

<210> SEQ ID NO 5
<211> LENGTH: 306
<212> TYPE: PRT
<213> ORGANISM: Citrobacter youngae

<400> SEQUENCE: 5

Met Phe Pro Gln Cys Lys Phe Ser Arg Ala Phe Leu His Pro Arg Tyr
1               5                   10                  15

Trp Leu Thr Trp Phe Gly Val Gly Val Leu Trp Leu Leu Val Gln Leu
            20                  25                  30

Pro Tyr Pro Leu Leu Cys Phe Leu Gly Thr Arg Thr Gly Thr Leu Ala
        35                  40                  45

Arg Pro Phe Leu Lys Arg Glu Ser Ile Ala Arg Lys Asn Leu Glu
50                  55                  60

Leu Cys Phe Pro Asn Leu Ser Gln Glu Glu Arg Asp Lys Leu Val Asp
65                  70                  75                  80

Glu Asn Phe Arg Ser Leu Gly Met Gly Leu Leu Glu Thr Gly Met Ala
                85                  90                  95

Trp Phe Trp Pro Asp Arg Arg Val Arg Lys Trp Phe Asp Val Glu Gly
            100                 105                 110

Leu Asp Asn Leu Gln Arg Ala Gln Ile Glu Gly Arg Gly Val Met Val
        115                 120                 125

Val Gly Val His Phe Met Ser Leu Glu Leu Gly Gly Arg Val Met Gly
130                 135                 140

Leu Cys Gln Pro Thr Met Ala Thr Tyr Arg Pro His Asn Asn Lys Leu
145                 150                 155                 160

Met Glu Trp Ile Gln Thr Arg Gly Arg Met Arg Ser Asn Lys Ala Met
                165                 170                 175

Ile Gly Arg Asn Asn Leu Arg Gly Ile Val Gly Ala Leu Lys Lys Gly
            180                 185                 190

Glu Ala Val Trp Phe Ala Pro Asp Gln Asp Tyr Gly Arg Lys Gly Ser
        195                 200                 205

Ser Phe Ala Pro Phe Phe Ala Val Lys Asp Val Ala Thr Thr Asn Gly
210                 215                 220

Thr Tyr Val Leu Ser Arg Leu Ser Gly Ala Ala Met Leu Thr Val Thr
225                 230                 235                 240

Met Val Arg Lys Ala Asp Asn Ser Gly Tyr Arg Leu Phe Ile Thr Pro
                245                 250                 255

Gln Met Glu Gly Tyr Pro Ala Asp Glu Ser Gln Ala Ala Ala Tyr Met
            260                 265                 270

Asn Lys Ile Ile Glu Lys Glu Ile Met Arg Ala Pro Glu Gln Tyr Leu
        275                 280                 285

Trp Ile His Arg Arg Phe Lys Thr Arg Pro Met Gly Glu Ala Ser Leu
290                 295                 300

Tyr Ile
305
```

<210> SEQ ID NO 6
<211> LENGTH: 311
<212> TYPE: PRT
<213> ORGANISM: Haemophilus aegyptius

<400> SEQUENCE: 6

Met Lys Asn Glu Lys Leu Pro Gln Phe Gln Pro His Phe Leu Val Pro
1               5                   10                  15

Lys Tyr Trp Leu Phe Trp Leu Gly Val Ala Ile Trp Arg Ser Ile Leu
            20                  25                  30

Cys Leu Pro Tyr Pro Ile Leu Arg His Ile Gly His Gly Leu Gly Trp
        35                  40                  45

Leu Phe Ser His Leu Asn Glu Gly Lys Arg Arg Ala Ile Ala Arg
    50                  55                  60

Arg Asn Leu Glu Leu Cys Phe Pro Tyr Met Pro Glu Asn Glu Arg Glu
65                  70                  75                  80

Thr Ile Leu Gln Glu Asn Leu Arg Ser Val Gly Met Ala Ile Ile Glu
                85                  90                  95

Thr Gly Met Ala Trp Phe Trp Ser Asp Ser Arg Ile Lys Lys Trp Ser
            100                 105                 110

Lys Val Glu Gly Leu His Tyr Leu Lys Glu Asn Gln Lys Asp Gly Ile
        115                 120                 125

Val Leu Val Gly Val His Phe Leu Thr Leu Glu Leu Gly Ala Arg Ile
    130                 135                 140

Ile Gly Leu His His Pro Gly Ile Gly Val Tyr Arg Pro Asn Asp Asn
145                 150                 155                 160

Pro Leu Leu Asp Trp Leu Gln Thr Gln Gly Arg Leu Arg Ser Asn Lys
                165                 170                 175

Asp Met Phe Asp Arg Lys Asp Leu Arg Gly Met Ile Lys Ala Leu Arg
            180                 185                 190

His Glu Glu Thr Ile Trp Tyr Ala Pro Asp His Asp Tyr Gly Arg Lys
        195                 200                 205

Asn Ala Val Phe Ala Pro Phe Phe Ala Val Pro Asp Ala Cys Thr Thr
    210                 215                 220

Thr Gly Ser Tyr Tyr Leu Leu Lys Ser Ser Gln Asn Ser Lys Val Ile
225                 230                 235                 240

Pro Phe Ala Pro Leu Arg Asn Lys Asp Gly Ser Gly Tyr Thr Val Ser
                245                 250                 255

Ile Ser Ala Pro Val Asp Phe Thr Asp Leu Gln Asp Glu Thr Ala Ile
            260                 265                 270

Ala Thr Arg Met Asn Gln Ile Val Glu Lys Glu Ile Met Lys Gly Ile
        275                 280                 285

Ser Gln Tyr Met Trp Leu His Arg Arg Phe Lys Thr Arg Pro Asp Glu
    290                 295                 300

Lys Thr Pro Ser Leu Tyr Asp
305                 310

<210> SEQ ID NO 7
<211> LENGTH: 304
<212> TYPE: PRT
<213> ORGANISM: Klebsiella sp.

<400> SEQUENCE: 7

Met Ala Cys Val Phe Asn Lys Gln Leu Leu His Pro Arg Asn Trp Leu
1               5                   10                  15

Thr Trp Phe Gly Leu Gly Ile Leu Trp Leu Ile Val Gln Leu Pro Tyr
            20                  25                  30

Pro Leu Leu His Phe Ile Gly Thr Ser Ala Gly Arg Leu Ser Arg Arg
        35                  40                  45

Phe Leu Lys Arg Arg Glu His Ile Ala Arg Arg Asn Ile Glu Leu Cys
    50                  55                  60

Phe Pro Asp Met Ser Pro Ala Ala Arg Glu Thr Leu Ile Asp Gln Asn
65                  70                  75                  80

Phe Met Ser Leu Gly Met Gly Leu Ile Glu Thr Gly Met Ala Trp Phe
                85                  90                  95

Trp Ser Asp Glu Arg Val Lys Lys Trp Phe Asp Val Glu Gly Phe Ala
            100                 105                 110

Asn Leu Asn His Ala Leu Ser Gly Gly Lys Gly Val Met Val Val Gly
        115                 120                 125

Val His Phe Met Ser Leu Glu Leu Gly Gly Arg Ala Met Gly Leu Cys
    130                 135                 140

Arg Pro Met Met Ala Thr Tyr Arg Pro His Asn Ser Pro Leu Met Glu
145                 150                 155                 160

Trp Val Gln Thr Arg Gly Arg Leu Arg Ser Asn Lys Ala Met Ile Asp
                165                 170                 175

Arg Asn Asn Leu Thr Gly Leu Val His Ala Leu Lys Ser Gly Glu Ala
            180                 185                 190

Val Trp Phe Ala Pro Asp Gln Asp Tyr Gly Pro Lys Gly Ser Val Phe
        195                 200                 205

Ala Pro Phe Phe Ser Val Pro Gln Ala Ala Thr Thr Asn Gly Thr Tyr
    210                 215                 220

Val Leu Ser Arg Leu Ser Gly Ala Lys Met Leu Ser Ile Ser Met Val
225                 230                 235                 240

Arg Lys Leu Asp Arg Gln Gly Tyr Ser Leu His Ile Ser Glu Val Met
                245                 250                 255

Asn Asp Tyr Pro Gly Glu Asp Lys Gln Ile Ala Ala Gly Tyr Ile Asn
            260                 265                 270

Lys Val Ile Glu Arg Glu Ile Leu Arg Ala Pro Glu Gln Tyr Leu Trp
        275                 280                 285

Val His Arg Arg Phe Lys Thr Arg Pro Leu Gly Glu Pro Ser Val Tyr
    290                 295                 300

<210> SEQ ID NO 8
<211> LENGTH: 306
<212> TYPE: PRT
<213> ORGANISM: Salmonella enterica

<400> SEQUENCE: 8

Met Phe Pro Gln Ser Lys Phe Ser Arg Ala Phe Leu His Pro Arg Tyr
1               5                   10                  15

Trp Leu Thr Trp Phe Gly Val Gly Ile Leu Trp Leu Leu Val Gln Leu
            20                  25                  30

Pro Tyr Pro Val Leu Arg Phe Leu Gly Thr Arg Thr Gly Lys Leu Ala
        35                  40                  45

Arg Pro Phe Leu Lys Arg Arg Glu Ser Ile Ala Gln Lys Asn Ile Glu
    50                  55                  60

```
Leu Cys Phe Pro Thr Leu Ser Arg Glu Glu Arg Glu Lys Leu Ile Ala
 65                  70                  75                  80

Glu Asn Phe His Ser Leu Gly Met Ala Leu Leu Glu Thr Gly Met Ala
                 85                  90                  95

Trp Phe Trp Pro Asp Ser Arg Val Arg Lys Trp Phe Asp Val Asp Gly
            100                 105                 110

Leu Asp Asn Leu Thr Arg Ala Gln Ala Gln Asn Arg Gly Val Met Val
        115                 120                 125

Val Gly Val His Phe Met Ser Leu Glu Leu Gly Gly Arg Val Met Gly
130                 135                 140

Leu Cys Gln Pro Met Met Ala Thr Tyr Arg Pro His Asn Asn Pro Leu
145                 150                 155                 160

Met Glu Trp Val Gln Thr Arg Gly Arg Met Arg Ser Asn Lys Ala Met
                165                 170                 175

Ile Gly Arg Asn Asn Leu Arg Gly Ile Val Gly Ala Leu Lys Lys Gly
            180                 185                 190

Glu Ala Val Trp Phe Ala Pro Asp Gln Asp Tyr Gly Pro Lys Gly Ser
        195                 200                 205

Ser Phe Ala Pro Phe Phe Ala Val Glu Asn Val Ala Thr Thr Asn Gly
210                 215                 220

Thr Tyr Val Leu Ser Arg Leu Ser Gly Ala Ala Met Leu Thr Val Thr
225                 230                 235                 240

Met Val Arg Lys Ser Asp Asn Ser Gly Tyr Arg Leu Tyr Ile Thr Pro
                245                 250                 255

Glu Met Glu Gly Tyr Pro Ala Asp Glu Asn Gln Ala Ala Ala Tyr Met
            260                 265                 270

Asn Lys Ile Ile Glu Lys Glu Ile Met Arg Ala Pro Glu Gln Tyr Leu
        275                 280                 285

Trp Ile His Arg Arg Phe Lys Thr Arg Pro Leu Gly Glu Ala Ser Leu
290                 295                 300

Tyr Ile
305

<210> SEQ ID NO 9
<211> LENGTH: 306
<212> TYPE: PRT
<213> ORGANISM: Serratia plymuthica

<400> SEQUENCE: 9

Met Lys Arg Pro Gln Glu Phe Arg Ser Ala Leu Leu His Pro Arg Tyr
 1                   5                  10                  15

Trp Phe Thr Trp Phe Gly Leu Ala Ile Leu Phe Leu Leu Val Gln Leu
                 20                  25                  30

Pro Tyr Pro Leu Leu His Lys Leu Gly Val Trp Met Gly Arg Thr Ser
            35                  40                  45

Met Arg Phe Leu Lys Arg Val Ala Ile Thr Arg Arg Asn Leu Glu
        50                  55                  60

Leu Cys Phe Pro Asp Met Asp Glu Ala Gln Arg Glu Arg Lys Val Ile
 65                  70                  75                  80

Gly Asn Phe Glu Ser Leu Gly Met Gly Leu Leu Glu Thr Gly Met Ala
                 85                  90                  95

Trp Phe Trp Ser Asp Lys Arg Val Lys Arg Trp Phe Asn Val Ser Gly
            100                 105                 110

Ile Asn His Leu Lys Met Ala Gln Gln Asn Glu Arg Gly Val Leu Val
        115                 120                 125
```

```
Ile Gly Val His Phe Met Ser Leu Glu Leu Gly Gly Arg Ala Met Gly
    130                 135                 140

Leu Cys Gln Pro Met Met Ala Met Tyr Arg Pro His Asn Asn Lys Ala
145                 150                 155                 160

Met Glu Trp Ala Gln Thr Lys Gly Arg Met Arg Ser Asn Lys Ala Met
                165                 170                 175

Leu Asp Arg Lys Asp Leu Arg Gly Met Val His Ala Leu Lys Arg Gly
            180                 185                 190

Glu Ala Val Trp Phe Ala Pro Asp Gln Asp Tyr Gly Pro Arg Gly Ser
        195                 200                 205

Val Phe Ala Pro Leu Phe Ala Val Asp Gln Ala Thr Thr Ser Gly
    210                 215                 220

Thr Phe Met Leu Ala Arg Met Ala Lys Pro Ala Leu Val Pro Val Val
225                 230                 235                 240

Leu Ile Arg Arg Glu Lys Gly Arg Gly Tyr Asp Leu Leu Ile Gln Pro
                245                 250                 255

Ala Leu Glu Asp Tyr Pro Ile Gly Asp Glu Leu Ala Ala Ala Ala Tyr
            260                 265                 270

Met Asn Lys Val Val Lys Glu Ile Met Arg Ala Pro Glu Gln Tyr
        275                 280                 285

Met Trp Leu His Arg Arg Phe Lys Thr Arg Pro Ile Gly Ala Pro Ser
    290                 295                 300

Leu Tyr
305

<210> SEQ ID NO 10
<211> LENGTH: 306
<212> TYPE: PRT
<213> ORGANISM: Shigella flexneri

<400> SEQUENCE: 10

Met Phe Pro Gln Cys Lys Phe Ser Arg Glu Phe Leu His Pro Arg Tyr
1               5                   10                  15

Trp Leu Thr Trp Phe Gly Leu Gly Val Leu Trp Leu Trp Val Gln Leu
                20                  25                  30

Pro Tyr Pro Val Leu Cys Phe Leu Gly Thr Arg Ile Gly Ala Met Ala
            35                  40                  45

Arg Pro Phe Leu Lys Arg Glu Ser Ile Ala Arg Lys Asn Leu Glu
        50                  55                  60

Leu Cys Phe Pro Gln His Ser Ala Glu Arg Glu Lys Met Ile Ala
65                  70                  75                  80

Glu Asn Phe Arg Ser Leu Gly Met Ala Leu Val Glu Thr Gly Met Ala
                85                  90                  95

Trp Phe Trp Pro Asp Ser Arg Val Arg Lys Trp Phe Asp Val Glu Gly
            100                 105                 110

Leu Asp Asn Leu Lys Arg Ala Gln Met Gln Asn Arg Gly Val Met Val
        115                 120                 125

Val Gly Val His Phe Met Ser Leu Glu Leu Gly Gly Arg Val Met Gly
    130                 135                 140

Leu Cys Gln Pro Met Met Ala Thr Tyr Arg Pro His Asn Asn Gln Leu
145                 150                 155                 160

Met Glu Trp Val Gln Thr Arg Gly Arg Met Arg Ser Asn Lys Ala Met
                165                 170                 175

Ile Gly Arg Asn Asn Leu Arg Gly Ile Val Gly Ala Leu Lys Lys Gly
            180                 185                 190
```

-continued

Glu Ala Val Trp Phe Ala Pro Asp Gln Asp Tyr Gly Arg Lys Gly Ser
             195                 200                 205

Ser Phe Ala Pro Phe Phe Ala Val Glu Asn Val Ala Thr Thr Asn Gly
    210                 215                 220

Thr Tyr Val Leu Ser Arg Leu Ser Gly Ala Ala Met Leu Thr Val Thr
225                 230                 235                 240

Met Val Arg Lys Ala Asp Tyr Ser Gly Tyr Arg Leu Phe Ile Thr Pro
                245                 250                 255

Glu Met Glu Gly Tyr Pro Thr Asp Glu Asn Gln Ala Ala Tyr Met
            260                 265                 270

Asn Lys Ile Ile Glu Lys Glu Ile Met Arg Ala Pro Glu Gln Tyr Leu
        275                 280                 285

Trp Ile His Arg Arg Phe Lys Thr Arg Pro Val Gly Glu Ser Ser Leu
    290                 295                 300

Tyr Ile
305

<210> SEQ ID NO 11
<211> LENGTH: 20
<212> TYPE: DNA
<213> ORGANISM: Artificial
<220> FEATURE:
<223> OTHER INFORMATION: LptA Fw primer

<400> SEQUENCE: 11
gccttccttt ccctgtattc                                              20

<210> SEQ ID NO 12
<211> LENGTH: 19
<212> TYPE: DNA
<213> ORGANISM: Artificial
<220> FEATURE:
<223> OTHER INFORMATION: LptA Re primer

<400> SEQUENCE: 12
ggtgttcgga cacatatgc                                               19

<210> SEQ ID NO 13
<211> LENGTH: 18
<212> TYPE: DNA
<213> ORGANISM: Artificial
<220> FEATURE:
<223> OTHER INFORMATION: LpxL1 Fw primer

<400> SEQUENCE: 13
ctgatcgggc agatacag                                                18

<210> SEQ ID NO 14
<211> LENGTH: 18
<212> TYPE: DNA
<213> ORGANISM: Artificial
<220> FEATURE:
<223> OTHER INFORMATION: LpxL1 Re primer

<400> SEQUENCE: 14
gtgcgctacc gcaataag                                                18

<210> SEQ ID NO 15
<211> LENGTH: 20
<212> TYPE: DNA
<213> ORGANISM: Artificial
<220> FEATURE:
<223> OTHER INFORMATION: LpxL2 Fw primer

```
<400> SEQUENCE: 15
aaacagatac tgcgtcggaa                                               20

<210> SEQ ID NO 16
<211> LENGTH: 18
<212> TYPE: DNA
<213> ORGANISM: Artificial
<220> FEATURE:
<223> OTHER INFORMATION: LpxL2 Re primer

<400> SEQUENCE: 16
ccctttgcga accgccat                                                 18

<210> SEQ ID NO 17
<211> LENGTH: 15
<212> TYPE: DNA
<213> ORGANISM: Artificial
<220> FEATURE:
<223> OTHER INFORMATION: PagL Fw primer

<400> SEQUENCE: 17
atgcaatttc tcaag                                                    15

<210> SEQ ID NO 18
<211> LENGTH: 15
<212> TYPE: DNA
<213> ORGANISM: Artificial
<220> FEATURE:
<223> OTHER INFORMATION: PagL Re primer

<400> SEQUENCE: 18
tcagaactgg tacgt                                                    15

<210> SEQ ID NO 19
<211> LENGTH: 28
<212> TYPE: DNA
<213> ORGANISM: Artificial
<220> FEATURE:
<223> OTHER INFORMATION: LpxP Fw primer

<400> SEQUENCE: 19
catatggccg cttacgcaga caatacac                                      28

<210> SEQ ID NO 20
<211> LENGTH: 30
<212> TYPE: DNA
<213> ORGANISM: Artificial
<220> FEATURE:
<223> OTHER INFORMATION: LpxP Re primer

<400> SEQUENCE: 20
gacgtcacgc ctgaatgact tcattacacc                                    30

<210> SEQ ID NO 21
<211> LENGTH: 28
<212> TYPE: DNA
<213> ORGANISM: Artificial
<220> FEATURE:
<223> OTHER INFORMATION: LpxE Fw primer

<400> SEQUENCE: 21
catatgatcc ggccctcatc ccattccc                                      28
```

```
<210> SEQ ID NO 22
<211> LENGTH: 28
<212> TYPE: DNA
<213> ORGANISM: Artificial
<220> FEATURE:
<223> OTHER INFORMATION: LpxE Re primer

<400> SEQUENCE: 22
tcatgacccg aaaggcgctt cccttcag                                         28
```

MODIFIED HEXA-ACYLATED NEISSERIAL LPS

FIELD OF THE INVENTION

The present invention relates to the field of medicine, in particular to the fields of immunology, medical microbiology and vaccinology. The invention pertains to modified LPS molecules that can be obtained from bioengineered meningococcal LPS mutants and that are useful as part of a whole cell vaccine, OMV vaccine or as purified LPS or lipid A molecules.

BACKGROUND OF THE INVENTION

Lipopolysaccharides (LPS), also known as bacterial endotoxin, are an abundant component of the outer membrane of gram-negative bacteria. During infection with gram-negative bacteria, LPS or more precisely the lipid A part of LPS activates the host's innate immune system (1-3). This activation occurs through binding of LPS to the pattern recognition receptor Toll-like receptor 4/myeloid differentiation factor 2 (TLR4/MD-2) complex, which starts a signalling cascade leading to cytokine production necessary to clear the infection (3,4). However, overstimulation of this signalling cascade and overproduction of the inflammatory cytokines is detrimental to the host and can lead to life-threatening conditions such as septic shock (5, 6).

For complete activation of the TLR4/MD-2 complex, a lipid A structure with six acyl chains and two phosphate groups is critical (7). However, many bacterial species carry enzymes that can modify their lipid A structure either by changing the number of acyl chains or phosphate groups resulting in altered activation of the TLR4/MD-2 complex (8), even to the point of being an antagonist instead of an agonist as is observed for the tetra-acylated *E. coli* lipid IVa structure (7,9).

The TLR4/MD-2 complex is unique among the TLR family of receptors because it can signal through both the MyD88 as well as the TRIF pathway. Modified lipid A structures can induce select signalling by preferential recruitment of the MyD88 or TRIF adaptor molecules. Preferential signalling through the TRIF pathway, which triggers production of type I interferons, is thought to be important for vaccine adjuvants (10, 11). Monophosphoryl lipid A (MPLA) is an example of a modified lipid A that triggers a TRIF-biased signalling (11). MPLA is a heterogeneous lipid A mixture from *Salmonella minnesota*, which has been chemically detoxified and is approved for the use as adjuvant in some vaccines (12). The main component of MPLA consists of a hexa-acylated 4'-monophosphoryl lipid A. Use of MPLA has the disadvantage that for its production a chemical treatment is needed in addition to LPS isolation from the bacteria and it only consists of the lipid A portion of LPS, making it water insoluble.

*Neisseria meningitidis* typically produces hexa-acylated LPS with phosphate and phosphoethanolamine groups appended to the 1 and 4' position of the lipid A (13, 14). Heterologous expression of LPS modifying enzymes such as PagL or deletion of lipid A biosynthesis enzymes such as LpxL1 and LpxL2 has been used to detoxify the highly active meningococcal LPS (13, 15). Deletion of LpxL1 was shown to be an advantageous method for detoxifying meningococcal LPS when making meningococcal outer membrane vesicle vaccines, without the need to use a detergent to reduce excess LPS-related reactogenicity (16). However, the activity of this modified LPS has been reduced to the point that it barely induces any activation of the TLR4/MD-2 complex on human cells, making it less applicable as a stand-alone vaccine adjuvant (17). Heterologous expression of pagL in *N. meningitidis* results in a different attenuated penta-acylated LPS structure, which is still capable of inducing TLR4 activation and induces a TRIF-biased cytokine production on a human monocytic cell line (13).

*E. coli* LpxP (Genbank accession number: U49787.1) is a cold shock-induced enzyme known to add a secondary 9-hexadecenoic acid (C16:1; palmitoleate) to the 2' acyl chain of lipid A (27).

It is an object of the invention of providing modified LPS molecules useful as adjuvants, which have the optimal balance between retaining a sufficient amount of immune activation while limiting toxic side effects. The present invention addresses this problem by heterologous expression of LPS modifying enzymes in combination with targeted deletion of lipid A biosynthesis genes to provide a diverse set of meningococcal LPS structures with a broad range of TLR4/MD-2 activation capacities that are useful in a variety of prophylactic and therapeutic applications.

SUMMARY OF THE INVENTION

In a first aspect, the invention relates to a neisserial LPS having a hexa-acylated lipid A moiety, wherein the hexa-acylated lipid A moiety is modified as compared to the lipid A moiety of a wild-type neisserial LPS in that it has a palmitoleoyl (instead of a lauroyl) as secondary acyl chain bound to the primary acyl chain on the glucosamine at the non-reducing end of the lipid A moiety. Preferably, the LPS, except for the hexa-acylated lipid A moiety, has the structure of LPS of *Neisseria meningitidis, Neisseria gonorrhoeae* or *Neisseria lactamica*, whereby more preferably, the *Neisseria meningitidis, Neisseria gonorrhoeae* or *Neisseria lactamica* is at least one of lgtB$^-$ and galE$^-$ and whereby most preferably, the *Neisseria meningitidis* is at least one of serogroup B and immunotype L3.

In a preferred neisserial LPS according to the invention, the hexa-acylated lipid A moiety has the structure of formula (I) (see below), wherein $R_1$ and $R_2$, independently, are either —P(O)(OH)$_2$, —[P(O)(OH)—O]$_2$—H, —[P(O)(OH)—O]$_2$—CH$_2$CH$_2$NH$_2$, —[P(O)(OH)—O]$_3$—CH$_2$CH$_2$NH$_2$, —[P(O)(OH)—O]$_3$—H or —P(O)(OH)—O—CH$_2$CH$_2$NH$_2$, and wherein, preferably $R_1$ and $R_2$, independently, are either —P(O)(OH)$_2$, —[P(O)(OH)—O]$_2$—H, —[P(O)(OH)—O]$_2$—CH$_2$CH$_2$NH$_2$ or —[P(O)(OH)—O]$_3$—CH$_2$CH$_2$NH$_2$.

In a second aspect, the invention relates to a composition comprising a mixture of: i) a neisserial LPS with the above defined hexa-acylated lipid A moiety; and ii) a neisserial LPS with a penta-acylated lipid A moiety wherein the penta-acylated lipid A moiety is modified as compared to the lipid A moiety of a wild-type neisserial LPS in that it lacks the secondary acyl chain bound to the primary acyl chain on the glucosamine at the non-reducing end of the lipid A moiety. Preferably, the penta-acylated neisserial LPS, except for the penta-acylated lipid A moiety, has the structure of an LPS as defined above for the hexa-acylated LPS. More preferably, the penta-acylated lipid A moiety has the structure of formula (II) (see below), wherein $R_1$ and $R_2$, independently, are either —P(O)(OH)$_2$, —[P(O)(OH)—O]$_2$—H, —[P(O)(OH)—O]$_2$—CH$_2$CH$_2$NH$_2$, —[P(O)(OH)—O]$_3$-CH$_2$CH$_2$NH$_2$, —[P(O)(OH)—O]$_3$—H or —P(O)(OH)—O—CH$_2$CH$_2$NH$_2$, and wherein, preferably R1 and R2, independently, are either —P(O)(OH)$_2$, —[P(O)(OH)—O]$_2$—H, —[P(O)(OH)—O]$_2$—CH$_2$CH$_2$NH$_2$ or —[P(O)

(OH)—O]₃—CH₂CH₂NH₂. Preferably, the composition comprises the hexa-acylated neisserial LPS and the penta-acylated neisserial LPS in a molar ratio in the range of 1:400 to 1:1.25.

In a second aspect, the invention relates to a genetically modified bacterium of the genus *Neisseria*, wherein the bacterium comprises: a) a genetic modification that reduces or eliminates the activity of a lipid A biosynthesis lauroyl acyltransferase encoded by an endogenous lpxL1 gene; and, b) a genetic modification that confers to the bacterium lipid A biosynthesis palmitoleoyltransferase activity. Preferably, the bacterium is a genetically modified *Neisseria meningitidis, Neisseria gonorrhoeae* or *Neisseria lactamica*. Preferably, in the genetically modified bacterium, the endogenous lpxL1 gene is a gene encoding an LpxL1 protein having an amino acid sequence with at least 90% sequence identity with at least one of SEQ ID NO's: 1-3, and the genetic modification that confers to the bacterium lipid A biosynthesis palmitoleoyltransferase activity is a genetic modification that introduces the expression of a heterologous lpxP gene having a nucleotide sequence that encodes an LpxP lipid A palmitoleoyltransferase that has at least 89% amino acid sequence identity with at least one of SEQ ID NO's: 4-10. More preferably, the nucleotide sequence that encodes an LpxP lipid A palmitoleoyltransferase encodes a known cold shock-induced LpxP palmitoleoyl acyltransferase having an amino acid sequence selected from the group consisting of SEQ ID NO: 4-10.

The genetically modified bacterium of the invention, further preferably is genetically modified to express a heterologous antigen, whereby preferably, the heterologous antigen is expressed on the extracellular outer membrane surface of the bacterium. In a preferred embodiment, the genetically modified bacterium has a genetic modification that reduces or eliminates the expression of at least one of an endogenous lgtB gene and an endogenous galE gene.

Preferably a genetically modified bacterium according to the invention is a *Neisseria meningitidis* serogroup B, immunotype L3. More preferably, the bacterium is *Neisseria meningitidis* strain H44/76 or a derivative thereof.

In a fourth aspect the invention pertains to a neisserial LPS according to the invention, or a composition comprising a mixture of hexa-acylated neisserial LPS and penta-acylated neisserial LPS according to the invention, wherein the LPS is obtainable or obtained from a genetically modified bacterium according to the invention.

In a fifth aspect, the invention relates to an OMV comprising a neisserial LPS of the invention, or a mixture of a hexa-acylated neisserial LPS and a penta-acylated neisserial LPS according to the invention. The OMV preferably is obtainable or obtained from a genetically modified bacterium according to the invention.

In a sixth aspect, the invention pertains to a composition comprising at least one of a neisserial LPS of the invention, a mixture of the invention, a genetically modified bacterium of the invention and an OMV of the invention. Preferably, the composition is a pharmaceutical composition further comprising a pharmaceutically accepted excipient. A preferred composition is an acellular vaccine comprising a neisserial LPS of the invention, a mixture of the invention, or an OMV of the invention. Another preferred composition is a whole cell vaccine comprising a bacterium of the invention. Preferably the compositions of the invention further comprises at least one non-neisserial antigen.

In a seventh aspect, the invention relates to a process for producing a neisserial LPS or a mixture of neisserial LPSs according to the invention. The process preferably comprises the steps of: a) cultivating a bacterium of the invention; and, b) optionally, at least one of extraction and purification of the LPS or of the mixture of LPSs.

In an eighth aspect, the invention relates to a process for producing an OMV according to the invention. The process preferably comprises the steps of: a) cultivating a genetically modified bacterium of the invention, at a temperature in the range of 20-42° C.; b) optionally, extracting the OMV; and, c) recovering the OMV, wherein the recovery at least comprises removal of the bacteria from the OMV. A preferred process for producing OMV is a detergent-free process. In a further preferred process, the bacterium is cultured at a temperature lower than 37° C.

In an ninth aspect, the invention relates to a process for producing an acellular vaccine of the invention. The process preferably comprises the steps of: a) producing at least one of: i) a neisserial LPS a mixture of neisserial LPSs according to the invention, preferably in a process as defined hereinabove; and, ii) an OMV according to the invention, preferably in a process as defined hereinabove; and, b) formulating at least one of the neisserial LPS, the mixture of neisserial LPSs and the OMV, optionally with further vaccine components, into a vaccine formulation.

In a tenth aspect, the invention relates to a process for producing a whole cell vaccine of the invention, wherein the process comprises the steps of: i) cultivating a bacterium of the invention; and, ii) optionally, at least one of inactivation of the bacterium and formulation into a vaccine. In a preferred process, the bacterium is cultured at a temperature lower than 37° C.

In an eleventh aspect, the invention relates to a neisserial LPS of the invention, a composition comprising a mixture of neisserial LPSs of the invention, a bacterium of the invention, an OMV of the invention, or a composition of the invention, for use as a medicament.

In a twelfth aspect, the invention relates to a neisserial LPS of the invention or a composition comprising a mixture of neisserial LPSs of the invention, for use in a treatment comprising inducing or stimulating an immune response in a subject. Preferably, the neisserial LPS or the mixture is for a use as adjuvant.

In a preferred embodiment, the neisserial LPS or the mixture is used in a treatment further comprising the administration of an antigen together with the neisserial LPS and wherein the treatment is for preventing or treating an infectious disease or tumour associated with the antigen.

In another preferred embodiment, the neisserial LPS of the invention or a composition comprising a mixture of neisserial LPSs of the invention is for a use as a Toll-like receptor 4 (TLR4) agonist in an immunotherapy, wherein preferably, the immunotherapy is an immunotherapy of a cancer or of a neurodegenerative disease. In an alternative embodiment, the immunotherapy comprises a generalized immune stimulation for preventing and/or reducing the spread of diverse microbial infections and/or to suppress bacterial growth.

DESCRIPTION OF THE INVENTION

Definitions

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to oxidoreductase nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at www.ncbi.nlm.nih.gov/.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagines and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

As used herein, the term "selectively hybridizing", "hybridizes selectively" and similar terms are intended to describe conditions for hybridization and washing under which nucleotide sequences at least 66%, at least 70%, at least 75%, at least 80%, more preferably at least 85%, even more preferably at least 90%, preferably at least 95%, more preferably at least 98% or more preferably at least 99% homologous to each other typically remain hybridized to each other. That is to say, such hybridizing sequences may share at least 45%, at least 50%, at least 55%, at least 60%, at least 65, at least 70%, at least 75%, at least 80%, more preferably at least 85%, even more preferably at least 90%, more preferably at least 95%, more preferably at least 98% or more preferably at least 99% sequence identity.

A preferred, non-limiting example of such hybridization conditions is hybridization in 6×sodium chloride/sodium citrate (SSC) at about 45° C., followed by one or more washes in 1 X SSC, 0.1% SDS at about 50° C., preferably at about 55° C., preferably at about 60° C. and even more preferably at about 65° C.

Highly stringent conditions include, for example, hybridization at about 68° C. in 5×SSC/5×Denhardt's solution/ 1.0% SDS and washing in 0.2×SSC/0.1% SDS at room temperature. Alternatively, washing may be performed at 42° C.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), Sambrook and Russell (2001) "Molecular Cloning: A Laboratory Manual ($3^{rd}$ edition), Cold Spring Harbor Laboratory, Cold Spring Harbor Laboratory Press, New York 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) residues, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or "expression construct" refer to nucleotide sequences that are capable of effecting expression of a gene in host cells or host organisms compatible with such sequences. These expression vectors typically include at least suitable transcription regulatory sequences and optionally, 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

The term "selectable marker" is a term familiar to one of ordinary skill in the art and is used herein to describe any genetic entity which, when expressed, can be used to select for a cell or cells containing the selectable marker. The term "reporter" may be used interchangeably with marker, although it is mainly used to refer to visible markers, such as green fluorescent protein (GFP). Selectable markers may be dominant or recessive or bidirectional.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The term "peptide" as used herein is defined as a chain of amino acid residues, usually having a defined sequence. As used herein the term peptide is interchangeable with the terms "polypeptide" and "protein". In the context of the present invention, the term "peptide" is defined as being any peptide or protein comprising at least two amino acids linked by a modified or unmodified peptide bond. The term "peptide" refers to short-chain molecules such as oligopeptides or oligomers or to long-chain molecules such as proteins. A protein/peptide can be linear, branched or cyclic. The peptide can include D amino acids, L amino acids, or a combination thereof. A peptide according to the present invention can comprise modified amino acids. Thus, the peptide of the present invention can also be modified by natural processes such as post-transcriptional modifications or by a chemical process. Some examples of these modifications are: acetylation, acylation, ADP-ribosylation, amidation, covalent bonding with flavine, covalent bonding with a heme, covalent bonding with a nucleotide or a nucleotide derivative, covalent bonding to a modified or unmodified carbohydrate moiety, bonding with a lipid or a lipid derivative, covalent bonding with a phosphotidylinositol, cross-linking, cyclization, disulfide bond formation, demethylation, cysteine molecule formation, pyroglutamate formation, formylation, gamma-carboxylation, hydroxylation, iodination, methylation, oxidation, phosphorylation, racemization, hydroxylation, etc. Thus, any modification of the peptide which does not have the effect of eliminating the immunogenicity of the peptide, is covered within the scope of the present invention.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3'-nontranslated sequence (3'-end) comprising a polyadenylation site. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide. The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically (but not necessarily) be operably linked to another (heterologous) promoter sequence and, if applicable, another (heterologous) secretory signal sequence and/or terminator sequence than in its natural environment. It is understood that the regulatory sequences, signal sequences, terminator sequences, etc. may also be homologous to the host cell.

The terms "heterologous" and "exogenous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous and exogenous nucleic acids or proteins are not endogenous to the cell into which it is introduced, but have been obtained from another cell or synthetically or recombinantly produced. Generally, though not necessarily, such nucleic acids encode proteins, i.e. exogenous proteins, that are not normally produced by the cell in which the DNA is transcribed or expressed. Similarly exogenous RNA encodes for proteins not normally expressed in the cell in which the exogenous RNA is present. Heterologous/exogenous nucleic acids and proteins may also be referred to as foreign nucleic acids or proteins. Any nucleic acid or protein that one of skill in the art would recognize as foreign to the cell in which it is expressed is herein encompassed by the term heterologous or exogenous nucleic acid or protein. The terms heterologous and exogenous also apply to non-natural combinations of nucleic acid or amino acid sequences, i.e. combinations where at least two of the combined sequences are foreign with respect to each other.

The term "immune response" as used herein refers to the production of antibodies and/or cells (such as T lymphocytes) that are directed against, and/or assist in the decomposition and/or inhibition of, a particular antigenic entity, carrying and/or expressing or presenting antigens and/or antigenic epitopes at its surface. The phrases "an effective immunoprotective response", "immunoprotection", and like terms, for purposes of the present invention, mean an immune response that is directed against one or more antigenic epitopes of a pathogen, a pathogen-infected cell or a cancer cell so as to protect against infection by the pathogen or against cancer in a vaccinated subject. For purposes of the present invention, protection against infection by a pathogen or protection against cancer includes not only the absolute prevention of infection or cancer, but also any detectable reduction in the degree or rate of infection by a pathogen or of the cancer, or any detectable reduction in the severity of the disease or any symptom or condition resulting from infection by the pathogen or cancer in the vaccinated subject, for example as compared to an unvaccinated infected subject. An effective immunoprotective response in the case of cancer also includes clearing up the cancer cells, thereby reducing the size of cancer or even abolishing the cancer. Vaccination in order to achieve this is also called therapeutic vaccination. Alternatively, an effective immunoprotective response can be induced in subjects that have not previously been infected with the pathogen and/or are not infected with the pathogen or do not yet suffer from cancer at the time of vaccination, such vaccination can be referred to as prophylactic vaccination.

According to the present invention, the general use herein of the term "antigen" refers to any molecule that binds specifically to an antibody. The term also refers to any molecule or molecular fragment that can be bound by an MHC molecule and presented to a T-cell receptor. Antigens can be e.g. proteinaceous molecules, i.e. polyaminoacid sequences, optionally comprising non-protein groups such as carbohydrate moieties and/or lipid moieties or antigens can be e.g. molecules that are not proteinaceous such as carbohydrates. An antigen can be e.g. any portion of a protein (peptide, partial protein, full-length protein), wherein the protein is naturally occurring or synthetically derived, a cellular composition (whole cell, cell lysate or disrupted cells), an organism (whole organism, lysate or disrupted cells) or a carbohydrate or other molecule, or a portion thereof, that is able to elicit an antigen-specific immune response (humoral and/or cellular immune response) in a particular subject, which immune response preferably is measurable via an assay or method.

The term "antigen" is herein understood as a structural substance which serves as a target for the receptors of an adaptive immune response. An antigen thus serves as target for a TCR (T-cell receptor) or a BCR (B-cell receptor) or the secreted form of a BCR, i.e. an antibody. The antigen can thus be a protein, peptide, carbohydrate or other hapten that is usually part of a larger structure, such as e.g. a cell or a virion. The antigen may originate from within the body ("self") or from the external environment ("non-self"). The immune system is usually non-reactive against "self" antigens under normal conditions due to negative selection of T cells in the thymus and is supposed to identify and attack only "non-self" invaders from the outside world or modified/harmful substances present in the body under e.g. disease conditions. Antigens structures that are the target of a cellular immune response are presented by antigen presenting cells (APC) in the form of processed antigenic peptides to the T cells of the adaptive immune system via a histocompatibility molecule. Depending on the antigen presented and the type of the histocompatibility molecule, several types of T cells can become activated. For T-Cell Receptor (TCR) recognition, the antigen is processed into small peptide fragments inside the cell and presented to a T-cell receptor by major histocompatibility complex (MHC).

The term "immunogen" is used herein to describe an entity that comprises or encodes at least one epitope of an antigen such that when administered to a subject, preferably together with an appropriate adjuvant, elicits a specific humoral and/or cellular immune response in the subject against the epitope and antigen comprising the epitope. An immunogen can be identical to the antigen or at least comprises a part of the antigen, e.g. a part comprising an epitope of the antigen. Therefore, to vaccinate a subject against a particular antigen means, in one embodiment, that an immune response is elicited against the antigen or immunogenic portion thereof, as a result of administration of an immunogen comprising at least one epitope of the antigen. Vaccination preferably results in a protective or therapeutic effect, wherein subsequent exposure to the antigen (or a source of the antigen) elicits an immune response against the antigen (or source) that reduces or prevents a disease or condition in the subject. The concept of vaccination is well-known in the art. The immune response that is elicited by administration of a prophylactic or therapeutic composition of the present invention can be any detectable change in any facet of the immune status (e.g., cellular response, humoral response, cytokine production), as compared to in the absence of the administration of the vaccine.

An "epitope" is defined herein as a single immunogenic site within a given antigen that is sufficient to elicit an immune response in a subject. Those of skill in the art will recognize that T cell epitopes are different in size and composition from B cell epitopes, and that T cell epitopes presented through the Class I MHC pathway differ from epitopes presented through the Class II MHC pathway. Epitopes can be linear sequences or conformational epitopes (conserved binding regions) depending on the type of immune response. An antigen can be as small as a single epitope, or larger, and can include multiple epitopes. As such, the size of an antigen can be as small as about 5-12 amino acids (e.g., a peptide) and as large as: a full length protein, including multimeric proteins, protein complexes, virions, particles, whole cells, whole microorganisms, or portions thereof (e.g., lysates of whole cells or extracts of microorganisms).

An adjuvant is herein understood to be an entity, that, when administered in combination with an antigen to a human or an animal subject to raise an immune response against the antigen in the subject, stimulates the immune system, thereby provoking, enhancing or facilitating the immune response against the antigen, preferably without necessarily generating a specific immune response to the adjuvant itself. A preferred adjuvant enhances the immune response against a given antigen by at least a factor of 1.5, 2, 2.5, 5, 10 or 20, as compared to the immune response generated against the antigen under the same conditions but in the absence of the adjuvant. Tests for determining the statistical average enhancement of the immune response against a given antigen as produced by an adjuvant in a group of animal or human subjects over a corresponding control group are available in the art. The adjuvant preferably is capable of enhancing the immune response against at least two different antigens.

OMV (also referred to as "blebs") are bi-layered membrane structures, usually spherical, with a diameter in the range of 20-250 nm (sometimes 10-500 nm), that are pinched off from the outer membrane of Gram-negative bacteria. The OMV membrane contains phospholipids (PL) on the inside and lipopolysaccharides (LPS) and PL on the outside, mixed with membrane proteins in various positions, largely reflecting the structure of the bacterial outer membrane from which they pinched off. The lumen of the OMV may contain various compounds from the periplasm or cytoplasm, such as proteins, RNA/DNA, and peptidoglycan (PG), however, unlike bacterial cells, OMV lack the ability to self-replicate. In the context of the present invention three type of OMV can be distinguished depending on the method of their production. sOMV are spontaneous or natural OMV that are purified and concentrated from culture supernatant, by separating intact cells from the already formed OMVs. Detergent OMV, dOMV, are extracted from cells with detergent, such as deoxycholate, which also reduces the content of reactogenic LPS. After detergent extraction dOMV are separated from cells and cellular debris and further purified and concentrated. Finally, the term native nOMV is used herein for OMV that are generated from concentrated dead cells with non-detergent cell disruption techniques, or that are extracted from cells with other (non-disruptive) detergent-free methods, to be able to clearly distinguish them from the wild-type spontaneous OMVs and from the detergent-extracted dOMV.

Any reference to nucleotide or amino acid sequences accessible in public sequence databases herein refers to the version of the sequence entry as available on the filing date of this document.

DETAILED DESCRIPTION OF THE INVENTION

The present invention relates to a novel neisserial LPS having a hexa-acylated lipid A moiety and to mixtures thereof with the corresponding neisserial LPS having a penta-acylated lipid A moiety, which are useful in generating and/or stimulating immune responses. Penta-acylated LPS molecules obtained from lpxL1⁻ mutant neisserial strains have reduced TLR4 activity as compared to the corresponding hexa-acylated LPS from the parent strain (13, 15). Interestingly, the present inventors have found that introduction of heterologous expression of an LpxP lipid A biosynthesis palmitoleoylacyltransferase into an lpxL1⁻ mutant neisserial host stain conferred temperature-sensitive addition of a palmitoleoyl chain as sixth acyl chain to the lipid A. The addition this sixth acyl chain to the lipid A again increases the TLR4 activity of the LPS in a temperature sensitivity manner. The temperature sensitivity of the LpxP enzyme thus enables to prepare mixtures of penta- and hexa-acylated LPS of which the ratio between penta- and hexa-acylated molecules can be controlled. By selecting the time and/or temperature that the mutant strain is grown, it is feasible to increase or decrease the amount of hexa-acylated lipid A structure relative to the corresponding penta-acylated structure and thereby the TLR4 activity and cytokine profile. This provides a new approach of fine-tuning the immunological properties of neisserial LPS preparation, such as e.g. meningococcal OMV vaccines.

In a first aspect therefore, the invention pertains to a neisserial LPS having a hexa-acylated lipid A moiety, or to the hexa-acylated lipid A moiety itself. Preferably the hexa-acylated lipid A moiety is modified as compared to the lipid A moiety of a wild-type neisserial LPS in that it has a palmitoleoyl as secondary acyl chain bound to the primary acyl chain on the glucosamine at the non-reducing end of the lipid A moiety. Thus, compared to the hexa-acylated lipid A moiety of a wild-type neisserial LPS, the hexa-acylated lipid A moiety of the invention has palmitoleoyl instead of a lauroyl as secondary acyl chain bound to the primary acyl chain on the glucosamine at the non-reducing end of the lipid A moiety. Preferably, the neisserial LPS or the hexa-acylated lipid A moiety are isolated.

In a preferred neisserial LPS of the invention, the hexa-acylated lipid A moiety has the structure of formula (I):

(I)

wherein $R_1$ and $R_2$, independently, are either —P(O)(OH)$_2$, —[P(O)(OH)—O]$_2$—H, —[P(O)(OH)—O]$_2$—CH$_2$CH$_2$NH$_2$, —[P(O)(OH)—O]$_2$—CH$_2$CH$_2$NH$_2$, —[P(O)(OH)—O]$_3$—H or —P(O)(OH)—O-CH$_2$CH$_2$NH$_2$, and wherein, preferably R1 and R2, independently, are either —P(O)(OH)$_2$, —[P(O)(OH)—O]$_2$—H, —[P(O)(OH)—O]$_2$—CH$_2$CH$_2$NH$_2$ or —[P(O)(OH)—O]$_3$—CH$_2$CH$_2$NH$_2$.

In a second aspect, the invention relates to a composition comprising i) a neisserial LPS with a hexa-acylated lipid A moiety as defined herein above; and, ii) a neisserial LPS with a penta-acylated lipid A moiety wherein the penta-acylated lipid A moiety is modified as compared to the lipid A moiety of a wild-type neisserial LPS in that it lacks the secondary acyl chain bound to the primary acyl chain on the glucosamine at the non-reducing end of the lipid A moiety. Preferably, in the composition, the neisserial LPS with a penta-acylated lipid A moiety has a penta-acylated lipid A moiety with the structure of formula (II):

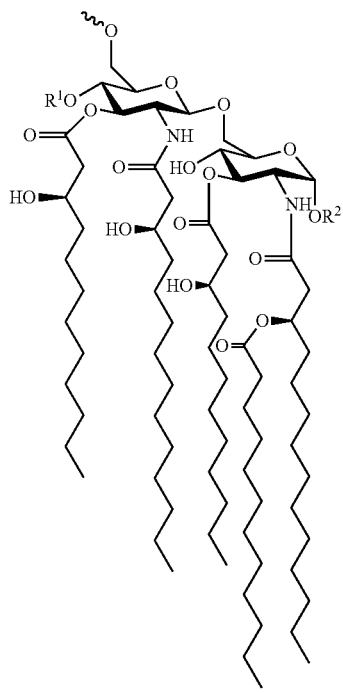

(II)

wherein $R_1$ and $R_2$, independently, are either —P(O)(OH)$_2$, —[P(O)(OH)—O]$_2$—H, —[P(O)(OH)—O]$_2$—CH$_2$CH$_2$NH$_2$, —[P(O)(OH)—O]$_3$—CH$_2$CH$_2$NH$_2$, —[P(O)(OH)—O]$_3$—H or —P(O)(OH)—O—CH$_2$CH$_2$NH$_2$, and wherein, preferably R1 and R2, independently, are either —P(O)(OH)$_2$, —[P(O)(OH)—O]$_2$—H, —[P(O)(OH)—O]$_2$—CH$_2$CH$_2$NH$_2$ or —[P(O)(OH)—O]$_3$—CH$_2$CH$_2$NH$_2$.

In a composition of the invention, the hexa-acylated neisserial LPS and the penta-acylated neisserial LPS are present in a molar ratio in the range of 1:400 to 1:1.25. The range of molar ratios of the hexa-acylated LPS to the penta-acylated LPS can have end points selected from 1:400, 1:200, 1:100, 1:50, 1:25, 1:10, 1:5, 1:2, 1:1.5 and 1:1.25. A molar ratio of hexa-acylated LPS to the penta-acylated LPS can suitably be determined by mass spectrometry. The composition can be any composition herein further described below and it can be produced in the desired ratio in methods further described herein below. It is further understood that when reference is made herein to a neisserial LPS of the invention, this neisserial LPS also includes any (composition comprising) mixture of the hexa-acylated neisserial LPS and the penta-acylated neisserial LPS described herein above. The higher the amount of the hexa-acylated LPS relative to the penta-acylated LPS, the higher the specific TLR4 agonist activity or the specific reactogenicity will be.

Except for their hexa-acylated or penta-acylated lipid A moieties described above, the neisserial LPS of the invention otherwise have the structure of a lipopolysaccharide that is obtained or obtainable from a bacterium of the genus *Neisseria*. Neisserial LPS are sometimes also referred to as lipooligosaccharides (LOS) due to the fact that they differ from the LPS of the Enterobacteriaceae by lacking the O side chains. In the context of the invention the terms "LPS" and "LOS" are however interchangeable. For reasons of consistency we shall further refer to LPS. The bacterium of the genus *Neisseria* from which the LPS of the invention are obtained or obtainable can be a wild type *Neisseria*, or a *Neisseria* having one or more of the genetic modifications described herein below. The bacterium of the genus *Neisseria* preferably is of a species selected from *Neisseria meningitidis*, *Neisseria gonorrhoeae* and *Neisseria lactamica*, whereby more preferably the *Neisseria meningitidis* is at least one of serogroup B and immunotype L3.

Preferably therefore, except for hexa-acylated or penta-acylated lipid A moieties, the remainder of the neisserial LPS of the invention have the structure of LPS of *Neisseria meningitidis*, *Neisseria gonorrhoeae* or *Neisseria lactamica* or a strain of these species having a genetic modification as described herein below. More preferably, except for hexa-acylated or penta-acylated lipid A moieties, the remainder of the neisserial LPS of the invention have the structure of LPS of *Neisseria meningitidis* that is at least one of serogroup B and immunotype L3 or a strain of this serogroup and/or immunotype having a genetic modification as described herein below.

In a preferred embodiment the neisserial LPS of the invention have a modified oligosaccharide structure so as to remove possible epitopes that are suspected to provoke autoimmune responses, and/or to increase binding to dendritic cells and adjuvant activity. Preferably therefore, the neisserial LPS of the invention are obtained or obtainable from a bacterium of the genus *Neisseria* that has a genetic modification that reduces or eliminates the expression of at least one of an endogenous lgtB gene and an endogenous galE gene. Neisserial lgtB genes encode enzymes having lacto-N-neotetraose biosynthesis glycosyl transferase activity and are described e.g. by Jennings et al. (Mol Microbiol, 1995, 18:729-740) and by Arkin et al. (J Bacteriol. 2001, 183: 934-941). LPS from neisserial strains with lgtB disruptions has been shown to target the DC-SIGN lectin receptor on dendritic cells (DC), thereby skewing T-cell responses driven by DC towards T helper type 1 activity (Steeghs et al. Cell Microbiol. 2006, 8:316-25). Neisserial galE genes encode enzymes having UDP-glucose 4-epimerase activity and are described by Jennings et al. (Mol Microbiol, 1993, 10:361-369) and by Lee et al. (Infect Immun. 1995, 63: 2508-2515).

In a third aspect, the invention relates to a genetically modified bacterium of the genus *Neisseria*. The bacterium preferably is a bacterium comprising a neisserial LPS having a hexa-acylated lipid A moiety according to the first aspect of the invention. The bacterium is preferably genetically modified in that it comprises: a) a genetic modification that reduces or eliminates the activity of a lipid A biosynthesis lauroyl acyltransferase encoded by an endogenous lpxL1 gene; and, b) a genetic modification that confers to the bacterium a lipid A biosynthesis palmitoleoyl acyltransferase. A genetic modification that reduces or eliminates the activity of the lauroyl acyltransferase can e.g. be a missense mutation such as described in Fransen et al. (2009, PLoS Pathogens 5(4): e1000396). Preferably, the genetic modification that reduces or eliminates the activity of the lipid A biosynthesis lauroyl acyltransferase is a modification that reduces or eliminates the expression of an endogenous lpxL1 gene. The genetically modified bacterium preferably is bacterium of a species selected from *Neisseria meningiti-* dis, *Neisseria gonorrhoeae* and *Neisseria lactamica*. More preferably, the genetically modified *Neisseria meningitidis* is at least one of serogroup B and immunotype L3, most preferably, the genetically modified *Neisseria meningitidis* is the *Neisseria meningitidis* H44/76 strain or a derivative thereof.

The endogenous lpxL1 gene to be modified preferably is a gene that encodes a lipid A biosynthesis lauroyl acyltransferase. lpxL1 genes have also been referred to as htrBI or msbB genes. The lpxL1 gene of which the expression is to be reduced or eliminated in the bacterium of the invention, preferably is a gene that encodes a LpxL1 (lipid A biosynthesis lauroyl acyltransferase) comprising an amino acid sequence with at least 90, 91, 92, 93, 94, 95, 96, 97, 98, 99 or 100% sequence identity with at least one of SEQ ID NO: 1 (LpxL1 of *Neisseria meningitidis* H44/76), SEQ ID NO: 2 (LpxL1 of *Neisseria gonorrhoeae*, Genbank WP_050158792) and SEQ ID NO: 3 (LpxL1 of *Neisseria lactamica*, Genbank CBN86767). In a preferred embodiment, the expression of the lpxL1 gene is eliminated by inactivation of the gene, e.g. by disruption or deletion of the gene by methods known in the art per se.

The genetic modification that confers to the bacterium lipid A biosynthesis palmitoleoyl acyltransferase activity preferably is a genetic modification that introduces the expression of a heterologous lpxP gene having a nucleotide sequence that encodes a lipid A biosynthesis palmitoleoyl acyltransferase. The LpxP lipid A biosynthesis palmitoleoyl acyltransferase is an enzyme that catalyses the transfer of a palmitoleoyl chain from palmitoleoyl-acyl carrier protein to the lipid A precursor Kdo$_2$-lipid IV$_A$ (27).

Specifically, LpxP acylates the 2' (R)-3-hydroxymyristoyl chain. In *E.coli*, LpxP activity is cold shock induced within 15 min following a shift of exponentially growing cells from 37 to 12° C. and peaks after 2 h and appearance of palmitoleoyltransferase activity is correlated with massive accumulation of lpxP mRNA at 12° C. (27). A preferred heterologous lpxP gene to be expressed in the bacterium of the invention is a gene that expresses a thermosensitive LpxP. A thermosensitive LpxP is herein understood as an LpxP of which the activity at 37° C. is less than 10, 5, 2, 1, 0.5, 0.2 or 0.1% of the activity at 12° C., as may e.g. be tested upon expression in *E.coli*.

The overall sequence conservation between the various LpxP homologs is rather high, with e.g. 90% sequence identity between the LpxP amino acid sequences of *E.coli* and *Citrobacter*. A large number of LpxP amino acid sequences is available in public databases such as Genbank, including e.g. LpxP amino acid sequences from genera such as *Escherichia, Citrobacter, Haemophilus, Klebsiella, Salmonella, Serratia* and *Shigella*. A preferred nucleotide sequence for expression of LpxP lipid A biosynthesis palmitoleoyl acyltransferase activity in a genetically modified bacterium of the invention is a nucleotide sequence that encodes a LpxP palmitoleoyl acyltransferase comprising an amino acid sequence with at least 89, 90, 91, 92, 93, 94, 95, 96, 97, 98, 99 or 100% sequence identity with at least one of SEQ ID NO: 4 (*Escherichia coli*, Genbank AAB66658), SEQ ID NO: 5 (*Citrobacter youngae*, Genbank EFE09970) SEQ ID NO: 6 (*Haemophilus aegyptius*, Genbank EGF15820), SEQ ID NO: 7 (*Klebsiella* sp., Genbank EFD82732), SEQ ID NO: 8 (*Salmonella enterica* subsp. *enterica* serovar Typhimurium, Genbank CBW18471), SEQ ID NO: 9 (*Serratia plymuthica*, Genbank EKF62147) and SEQ ID NO: 10 (*Shigella flexneri*, Genbank ADA74790). Preferably, the nucleotide sequence encodes a known thermosensitive or cold shock-induced LpxP palmitoleoyl acyltransferase e.g. having an amino acid sequence as set forth in any one of SEQ ID NO: 4-10.

In one embodiment the nucleotide sequence encodes a polypeptide with LpxP palmitoleoyl acyltransferase activity as it occurs in nature, e.g. as it can be isolated from a wild type source bacterium. Alternatively, the nucleotide sequence can encode engineered forms of any of the LpxP palmitoleoyl acyltransferases defined above and that comprise one or more amino acid substitutions, insertions and/or deletions as compared to the corresponding naturally occurring LpxP palmitoleoyl acyltransferase but that are within the ranges of identity or similarity as defined herein.

Preferably, a nucleotide sequence for expression of LpxP palmitoleoyl acyltransferase activity in a genetically modified bacterium of the invention is a nucleotide sequence that encodes a LpxP palmitoleoyl acyltransferase comprising in each of the invariable positions (that are indicated with a "*", i.e. an asteriks in the sequence alignment of Table 4), the amino acid present in that invariable position. More preferably, the LpxP palmitoleoyl acyltransferase amino acid sequence also comprises in the strongly conserved positions (that are indicated with a ":", i.e. a colon in the sequence alignment of Table 4) one of the amino acids that is present in the respective strongly conserved positions. Most preferably, the amino acid sequence further also comprises in the weakly conserved positions (that are indicated in the sequence alignment of Table 4 with a ".", i.e. a dot) one of the amino acids that is present in the respective weakly conserved positions. Amino acid substitutions outside of these invariable and conserved positions are less likely to have a negative effect on the LpxP palmitoleoyl acyltransferase enzymatic activity.

The genetically modified bacterium of the invention further preferably has one or more genetic modifications selected from the group consisting of: (i) a genetic modification that alters the LPS biosynthesis pathway, preferably in order to further modify the endotoxicity and/or reactogenicity of the LPS; (ii) a genetic modification that causes outer membrane retention of normally secreted antigens; (iii) a genetic modification that increases OMV production by removing outer membrane anchor proteins; (iv) a genetic modification that removes immune-modulating components which may trigger an undesired type of immune response; and, (v) a genetic modification that introduces expression of heterologous antigens.

An LPS that is modified to have reduced endotoxicity is herein understood as an LPS that is modified to have less toxicity than the toxicity of a corresponding wild-type LPS. Preferably, the modified LPS has less than about 90, 80, 60, 40, 20, 10, 5, 2, 1, 0.5, or 0.2% of the toxicity of the corresponding wild-type LPS. The toxicities of wild-type and various modified LPS's with reduced toxicity may be determined in any suitable assay known in the art. A preferred assay for determining the toxicity, i.e. the biological activity of the LPS is IL-6 induction in the MM6 macrophage cell line (see par. 1.4 below).

A preferred genetic modification that alters the LPS biosynthesis pathway is a genetic modification that is selected from the group consisting of: a) a genetic modification that reduces or eliminates expression of at least one of an lptA gene, an lpxK gene and homologues of these genes; and b) a genetic modification that introduces or increases the expression of at least one of an lpxE gene, an lpxF gene and homologues of these genes.

A preferred genetic modification that increases OMV production is a genetic modification that reduces or eliminates expression of a gene encoding an anchor protein between outer membrane and peptidoglycan in order to increase vesicle formation and thereby increase OMV yield. A suitable genetic modification for this purpose e.g. reduces or eliminates expression of an OmpA homologue, which are commonly found in Gram-negative bacteria, e.g. the RmpM protein in *Neisseria* (Steeghs et al., 2002 Cell Microbiol, 4:599-611; van de Waterbeemd et al., 2010 Vaccine, 28: 4810 - 4816). Thus, preferably, the genetically modified bacterium has a genetic modification reduces or eliminates expression of an rmpM gene or a homologue thereof.

Preferred genetic modifications that removes immune-modulating components which may trigger an undesired type of immune response are genetic modifications that reduces or eliminates the expression of at least one of an endogenous lgtB gene and an endogenous galE gene as described above.

Further preferred genetic modifications reduce or eliminate the expression of at least one gene selected from the group consisting of cps, ctrA, ctrB, ctrC, ctrD, exbB, exbD, frpB, lpbB, nmb0033, opA, opC, phoP, pilC, pmrE, pmrF, porA, porB, siaA, siaB, siaC, siaD, synA, synB, synC, tbpA, tbpB, and homologues of any of these genes. Many of these mutations are reviewed in WO02/09746.

In a further embodiment, the genetically modified bacterium of the invention, is further genetically modified to express a heterologous antigen. Preferably, the heterologous antigen is expressed on the extracellular outer membrane surface of the bacterium. The heterologous antigen can e.g. be an outer membrane protein from another bacterium, preferably from another Gram negative bacterium. Alternatively, the heterologous antigen can be fused to a protein that is expressed on the extracellular outer membrane surface of the bacterium, e.g. a neisserial outer membrane protein as are well known in the art per se.

Preferably, the heterologous antigen expressed by the genetically modified bacterium of the invention, comprises at least one epitope for inducing and/or enhancing an immune response against an antigen comprising the epitope. Preferably, a B-cell, humoral or antibody response is elicited by the epitope in the heterologous antigen. Preferably the epitope in the heterologous antigen elicits a protective and/or neutralizing antibody response. Alternatively and/or additionally, the heterologous antigen comprises epitopes that elicit a T cell response. A preferred T-cell response induced and/or enhanced by an immunogenic peptide comprises at least one of an HLA class I restricted CTL response and an HLA class II restricted Th response. More preferably the T-cell response consists of both an HLA class I restricted CTL response and simultaneously an HLA class II restricted Th response, and may be advantageously accompanied by a B-cell response.

The heterologous antigen can comprise one or more epitopes from a wide range of antigens of pathogens (infectious agents) and/or tumours. For example, the heterologous antigen may comprise one or more epitopes from antigens from pathogens and infectious agents such as viruses, bacteria, fungi and protozoa. Some examples of pathogenic viruses causing infections or tumours from which epitopes from antigens may be derived include: hepatitis (A, B, or C), herpes virus (e.g., VZV, HSV-I, HAV-6, HSV-II, and CMV, Epstein Barr virus), adenovirus, SV40 virus (causing mesothelioma), influenza virus, flaviviruses, ebola virus, echovirus, rhinovirus, coxsackie virus, coronavirus, respiratory syncytial virus (RSV), mumps virus, rotavirus, measles virus, rubella virus, parvovirus, vaccinia virus, HTLV virus, dengue virus, molluscum virus, poliovirus, rabies virus, JC virus, arboviral encephalitis virus, and human immunodeficiency virus (HIV virus; e.g., type I and II), human papilloma virus (HPV). Some examples of pathogenic bacteria causing infections from which epitopes from antigens may be derived include: *Borrelia, Listeria, Escherichia, Chlamydia, Coxiella, Rickettsial bacteria, Mycobacteria, Staphylococci, Streptocci, Pneumonococci, Meningococci, Gonococci, Klebsiella, Proteus, Serratia, Pseudomonas, Legionella, Diphtheria, Salmonella, Bacilli, Bordetella*, bacteria causing Cholera, Tetanus, Botulism, Anthrax, Plague, Leptospirosis, Whooping cough and Lymes disease. Some examples of pathogenic fungi causing infections from which epitopes from antigens may be derived include: *Candida* (e.g., *albicans, krusei, glabrata* and *tropicalis*), *Cryptococcus neoformans, Aspergillus* (e.g., *fumigatus, niger*), fungi of the genus *Mucorales* (*Mucor, Absidia* and *Rhizopus*), *Sporothrix schenkii, Blastomyces dermatitidis, Paracoccidioides brasiliensis, Coccidioides immitis* and *Histoplasma capsulatum*. Some examples of pathogenic parasites causing infections from which epitopes from antigens may be derived include: *Entamoeba histolytica, Balantidium coli, Naegleria, Fowleri, Acanthamoeba* sp., *Giardia Zambia, Cryptosporidium* sp., *Pneumocystis carinii, Plasmodium vivax, Babesia microti, Trypanosoma brucei, Trypanosoma cruzi, Leishmania donovani, Toxoplasma gondii* and *Plasmodium falciparis*.

In addition, the C-terminal fusion can comprise one or more epitopes from a wide range of tumour antigens, including e.g. MAGE, BAGE, RAGE, GAGE, SSX-2, NY-ESO-1, CT-antigen, CEA, PSA, p53, XAGE and PRAME but also virally induced malignancies, comprising Human papilloma virus (HPV), Kaposi sarcoma herpes virus (KSHV), Epstein Bar virus induced lymphoma's (EBV). Other examples of tumour antigens from which epitopes for use in the present invention may be derived are various ubiquitously expressed self-antigens that are known to be associated with cancer, which include e.g. p53, MDM-2, HDM2 and other proteins playing a role in p53 pathway, molecules such as surviving, telomerase, cytochrome P450 isoform 1B1, Her-2/neu, and CD19 and all so-called house hold proteins. Cancers that may be treated in accordance with the present invention are selected among the following list: lung, colon, esophagus, ovary, pancreas, skin, gastric, head and neck, bladder, sarcoma, prostate, hepatocellular, brain, adrenal, breast, endometrial, mesothelioma, renal, thyroid, hematological, carcinoid, melanoma, parathyroid, cervix, neuroblastoma, Wilms, testes, pituitary and pheochromocytoma cancers. In one embodiment, the heterologous antigen comprises or consists of one or more surface exposed epitopes from a proteinaceous antigen of an infectious agent or tumour. The heterologous antigen can e.g. comprises or consists of an extracellular and/or surface exposed domain of the proteinaceous antigen of an infectious agent or tumour.

In a fourth aspect, the invention relates to a hexa-acylated neisserial LPS as herein defined above or to (a composition comprising) a mixture of hexa- and penta-acylated neisserial LPS as herein defined above, wherein the LPS is obtained or obtainable from a genetically modified bacterium as herein defined above.

In a fifth aspect, the invention pertains to an OMV comprising the neisserial LPS as herein defined above. OMV (also known as "blebs") for use in vaccines have traditionally been prepared by detergent extraction (a dOMV purification process), wherein detergents such deoxycholate are used to remove LPS and increase vesicle release. The LPS of most Gram-negative bacteria, such as *N. meningitidis* is highly toxic, yet residual amounts (approx. 1%) are needed in OMV to maintain vesicle structure and for adjuvant activity. However, the neisserial LPS of the invention combines reduced toxicity with useful adjuvant activity and therefore preferably remain present in the OMV to a much larger degree than the toxic wild type LPS. The detergent extraction process is therefore less suitable for producing OMV comprising the neisserial LPS of the present invention. An OMV comprising a neisserial LPS according to the invention therefore preferably is not a detergent-extracted OMV. It is understood however, that a process for preparing an OMV that is not a detergent-extracted OMV does not exclude the use of any detergents. The use of low concentration of detergent and/or the use of mild detergents are not excluded as long as most of the neisserial LPS according to the invention, i.e. at least 5, 10, 20, 50, 60, 70, 80, 90, 95 or 99% of the neisserial LPS, is maintained, e.g. as compared the amount of neisserial LPS present in spontaneous or supernatant OMV from an equal amount of the same culture.

A preferred OMV comprising the neisserial LPS of the invention is a supernatant or spontaneous OMV, i.e. sOMV as herein defined above, or a native OMV, i.e. nOMV as herein defined above. Methods for preparing nOMV are e.g. described in Saunders et al. (1999, Infect Immun, 67, 113-119), van de Waterbeemd et al. (2012, Vaccine, 30: 3683-3690) and in WO2013/006055 and methods for preparing sOMV are e.g. described in van de Waterbeemd et al. (2013, PLoS ONE, 8(1): e54314. doi:10.1371/journal. pone.0054314) and in Lee et al. (2007, Proteomics, 7:3143-3153), all of which are incorporated herein by reference. The OMV comprising a neisserial LPS of the invention are preferably obtained or obtainable from a genetically modified neisserial bacterium as herein defined above.

In a sixth aspect, the invention relates to a composition comprising at least one of the neisserial LPS, a genetically modified bacterium and an OMV as herein defined above. Preferably, the composition is a pharmaceutical composition further comprises a pharmaceutically acceptable excipient, carrier, medium or delivery vehicle as are conventionally known in the art (see e.g. "Handbook of Pharmaceutical Excipients", Rowe et al eds. $7^{th}$ edition, 2012, www.pharmpress.com). Pharmaceutically acceptable stabilizing agents, osmotic agents, buffering agents, dispersing agents, and the like may also be incorporated into the pharmaceutical compositions. The preferred form depends on the intended mode of administration and therapeutic application. The pharmaceutical carrier can be any compatible, non-toxic substance suitable to deliver to the patient. The "active ingredients of the invention" are herein understood to be one or more of a neisserial LPS, a genetically modified bacterium or an OMV as defined herein above.

Pharmaceutically acceptable carriers for parenteral delivery are exemplified by sterile buffered 0.9% NaCl or 5% glucose optionally supplemented with a 20% albumin. Alternatively, the active ingredients of the invention can be suspended in Phosphate buffer saline (PBS). Preparations for parental administration must be sterile. The parental route for administration of the active ingredients of the invention is in accord with known methods, e.g. injection or infusion by intravenous, intraperitoneal, intramuscular, and intraarterial or intralesional routes. A typical pharmaceutical composition for intramuscular injection would be made up to contain, for example, 1-10 ml of phosphate buffered saline comprising the effective dosages of the active ingredients of the invention. Methods for preparing parenterally administrable compositions are well known in the art and described in more detail in various sources, including, for example, "Remington: The Science and Practice of Pharmacy" (Ed. Allen, L. V. 22nd edition, 2012, www.pharmpress.com).

In a preferred embodiment, the pharmaceutical composition of the invention is a vaccine. The vaccine can be an acellular vaccine preferably comprising at least one a neisserial LPS and an OMV as defined herein above. Alternatively, the vaccine can be a whole cell vaccine comprising at least a bacterium as herein defined above, wherein preferably the bacterium is inactivated or killed using means known in the art per se.

In a seventh aspect, the invention pertains to a process for producing a neisserial LPS of the invention. The process preferably comprises the steps of a) cultivating a genetically modified bacterium as herein defined above, preferably under condition conducive to the production of the LPS; and b) optionally, at least one of extraction and purification of the LPS. Methods for extraction of LPS are well known in the art (see e.g. 19). Methods for purification of LPS are described in the Examples herein and can e.g. include solid phase extraction (SPE) on reverse phase cartridges.

In the process, preferably, in step a), the temperature at which the genetically modified bacterium is cultured determines or is used to determine the molar ratio of the hexa-acylated neisserial LPS to the penta-acylated neisserial LPS of the invention. The optimal growth temperature for $Neisseria$ is in the range of 35-37° C., at which temperature the temperature-sensitive LpxP enzyme has almost no activity. However, at temperatures below 25° C., when LpxP enzyme is most active, $Neisseria$ will stop growing. Depending on the desired TLR4 agonist activity, and the corresponding desired molar ratio of hexa- to penta-acylated neisserial LPS to be produced, the genetically modified bacterium is preferably cultured in step a) of the process at a temperature in a range limited at the lower end by 20, 21, 22, 23, 24 or 25° C. and limited at the higher end by 37, 38, 39, 40, 41 or 42° C. In step a) of the process, the genetically modified bacterium can thus be cultured at any temperature selected from 20, 21, 22, 23, 24, 25, 26, 27, 28, 30, 31, 32, 33, 34, 35, 36, 37, 38, 39, 40, 41 and 42° C. to produce a desired molar ratio of hexa- to penta-acylated neisserial LPS. For example, the inventors have found that when an lpxL1$^-$ mutant $N. meningitidis$ expressing the $E. coli$ LpxP enzyme as used in the Examples, is grown at 25° C., a relative abundance of approximately 50% hexa-acyl lipid A is produced (i.e. a molar ratio of hexa- to penta-acylated neisserial LPS of about 1:2), whereas when grown at 37° C., extremely low amounts of hexa-acyl lipid A were produced, estimated to be about 0.5% (i.e. a molar ratio of hexa- to penta-acylated neisserial LPS of about 1:200). Therefore, in one preferred embodiment of the process of the invention, in step a) the bacterium is cultured at a temperature lower than 37, 36.5, 36, 35.5, 35, 34.5, or 34° C. This ensures that at least some hexa-acylated neisserial LPS is produced, composition comprising only the penta-acylated LPS already being obtainable from single mutant lpxL1$^-$ $Neisseria$. It is further envisaged that other ratio's than those obtained in the Examples herein can be obtained at 25° C. and 37° C., when using other neisserial host strain and/or in combination with heterologous expression of other LpxP enzymes. In further embodiments of the process of the invention, step a) can comprises at least two phases wherein the bacterium is cultivated at different temperatures. Step a) in the process can e.g. comprise one or more phases at a temperature allowing more rapid accumulation of biomass (e.g. at least 32, 33, 34, 35, 36, or 37 ° C.), followed by one or more phases at a temperature allowing for palmitoylation of the penta-acylated neisserial LPS (e.g.

not higher than 31, 30, 29, 28, 26, 25, 24, 23, 22, 21 or 20 ° C.). Alternatively, step a) in the process can start with a phase at a temperature allowing more rapid accumulation of biomass, followed by a phase during which the culture is cooled down to a temperature allowing for palmitoylation, whereby preferably the temperature is reduced along a predefined trajectory as a function of time or accumulated biomass.

In an eighth aspect, the invention relates to a process for producing an OMV of the invention. The process preferably comprises the steps of a) cultivating a genetically modified bacterium as herein defined above, preferably under condition conducive to the production of the OMV; b) optionally, extracting the OMV; and recovering the OMV, wherein the recovery at least comprises removal of the bacteria from the OMV. In the process, preferably, in step a), the temperature at which the genetically modified bacterium is cultured determines or is used to determine the molar ratio of the hexa-acylated neisserial LPS to the penta-acylated neisserial LPS of the invention as described above. Methods for preparing OMV, preferably detergent-free methods for preparing OMV, are described herein above. A preferred process for preparing OMV of the invention is thus a detergent-free process, e.g. a process for preparing nOMV or sOMV.

In a ninth aspect, the invention pertains to a process for producing an acellular vaccine as herein defined above. The process preferably comprises the steps of: a) producing at least one of: i) a neisserial LPS as herein defined above, preferably in a process for producing a neisserial LPS as herein defined above; and, ii) an OMV as herein defined above, preferably, in a process for producing an OMV as herein defined above; and, b) formulating at least one of the neisserial LPS and the OMV, optionally with further vaccine components, into a vaccine formulation.

In a tenth aspect, the invention relates to a process for producing a whole cell vaccine as herein defined above. The process preferably comprises the steps of: i) cultivating a genetically modified bacterium as herein defined; and, ii) optionally, at least one of inactivation of the bacterium and formulation into a vaccine.

In an eleventh aspect, the invention pertains to the use as medicament of at least one of a neisserial LPS of the invention, a genetically modified bacterium of the invention, an OMV of the invention, and a pharmaceutical composition of the invention.

In a twelfth aspect, the invention relates to a neisserial LPS of the invention for use in a treatment comprising inducing or stimulating an immune response in a subject.

Preferably, in the treatment, the neisserial LPS is used as adjuvant. A neisserial LPS of the invention can e.g. be included as adjuvant in a vaccine composition, preferably together with an antigen against which it is desirable to induce or stimulate an immune response. Preferably therefore, a neisserial LPS of the invention is used in a treatment comprising inducing or stimulating an immune response in a subject, wherein the treatment further comprises the administration of an antigen together with the neisserial LPS and wherein the treatment is for preventing or treating an infectious disease or tumour associated with the antigen, wherein the antigen preferably is an antigen as herein defined above.

In this aspect, the invention thus relates to a method for vaccination against, or for prophylaxis or therapy of an infectious disease or tumour, or for inducing or stimulating an immune response against an infectious disease or tumour. The method preferably at least comprises the step of administration of a therapeutically or prophylactically effective amount of an neisserial LPS of the invention or a pharmaceutical composition comprising said LPS, to a subject in need of said prophylaxis, therapy or immune response. The pharmaceutical composition comprising preferably also an antigen associated with the infectious disease or tumour, wherein the antigen preferably is an antigen as herein defined above.

In a thirteenth aspect, the invention relates to a neisserial LPS of the invention for use as a Toll-like receptor 4 (TLR4) agonist. Preferably, the neisserial LPS is used as TLR4 agonist in an immunotherapy. Preferably, the immunotherapy is an immunotherapy of a cancer (see e.g. 37) or of a neurodegenerative disease (see e.g. 35), including e.g. Alzheimer's disease or Parkinson's disease. Alternatively, the neisserial LPS is used as TLR4 agonist in a generalized immune stimulation for preventing and/or reducing the spread of (diverse) microbial infections and/or to suppress bacterial growth (see e.g. 36).

The advantage of the present invention is thus that the temperature sensitivity of the LpxP enzyme enables to prepare mixtures of penta- and hexa-acylated LPS of which the ratio between penta- and hexa-acylated molecules can be precisely controlled. By selecting the time and/or temperature that the mutant strain is grown, it is feasible to increase or decrease the amount of hexa-acylated lipid A structure relative to the corresponding penta-acylated structure and thereby modulate the TLR4 agonist activity of the neisserial LPS of the invention to the exact level of activity, and profile of subsequently released cytokines, required for a particular immunotherapeutic approach. Such controlled release of pro-inflammatory cytokines is important for using the neisserial LPS as an adjuvant, antigen and/or immunostimulatory molecule, since it is desirable to be able to induce or stimulate immunity without toxic effects. Often immune activation is correlated with more side effects due to unwanted inflammatory responses. In general, for vaccine application side effect levels are preferably kept as low as possible or more preferably be absent. However, for some specific immunotherapeutic applications such as those described above, the potential healing effects may outweigh considerable side effects. Therefore, even the high activity of ΔlpxL1-lpxP LPS grown at 25° C. could still be useful in such therapeutic approaches.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

DESCRIPTION OF THE FIGURES

FIG. 1. Charge deconvoluted ESI-FT mass spectra of LPS. The charge deconvoluted ESI-FT mass spectra of the LPS isolated from twelve different strains of *Neisseria meningitidis* are shown as follows: parent HB-1 strain (A), ΔlpxL1 (B), ΔlpxL2 (C), pagL (D), ΔlpxL1-pagL (E), ΔlpxL2-pagL (F), ΔlpxL1-lpxP cultured at 30° C. for 5 h (G)

or at 25° C. overnight (H), ΔlptA (I), ΔlptA-ΔlpxL1 (J), ΔlptA-pagL (K) and ΔlptA-lpxE (L). A simplified representation of the LPS structure assigned to the ion of 3408.507 u is included in mass spectrum (A). The vertical line at a mass of 3408.514 u, which corresponds to the calculated molecular mass of this latter LPS species, is used as a reference to indicate LPS composition assigned to other ion signals. See Supplemental Table 1 for detailed LPS composition proposals. All annotations refer to monoisotopic masses of the neutral molecules.

Figure 2B:
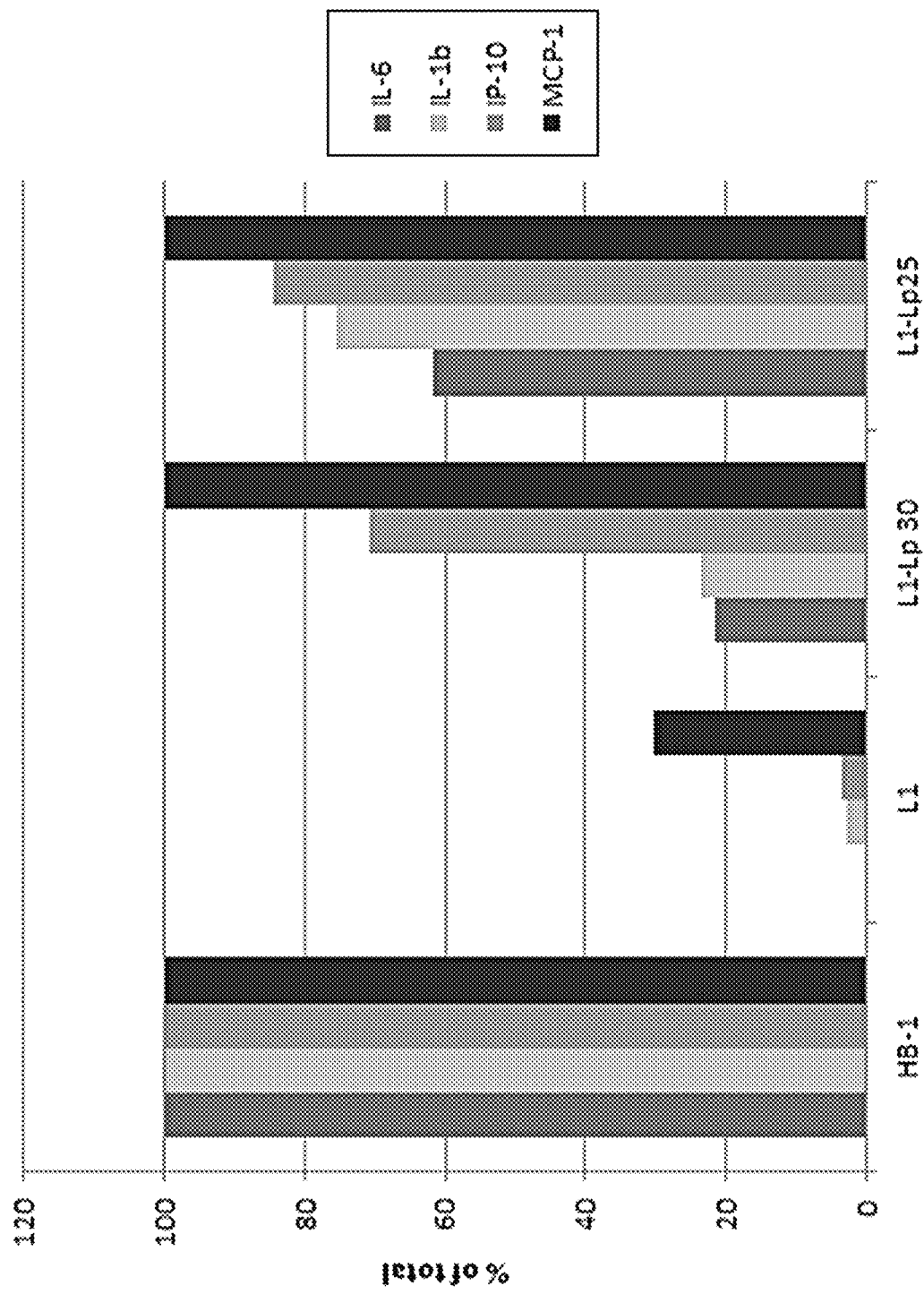

FIG. 2. TLR4 activation by N. meningitidis strains as indicated. HEK-blue hTLR4 cells were stimulated with 5-fold serial dilutions of heat-inactivated N. meningitidis for 20 h. TLR4 activation was measured by detection of secreted alkaline phosphatase. Results of serial dilutions are depicted in a line graph (A) and for a single $OD_{600nm}$ of 0.0004 in a bar graph (B). Data are expressed as mean values or mean±SD of three independent experiments. Statistical significance was determined with an ANOVA test comparing against HB-1. *, p<0.05; ****, p<0.0001. Data are also presented in Table 5.

Figure 3:
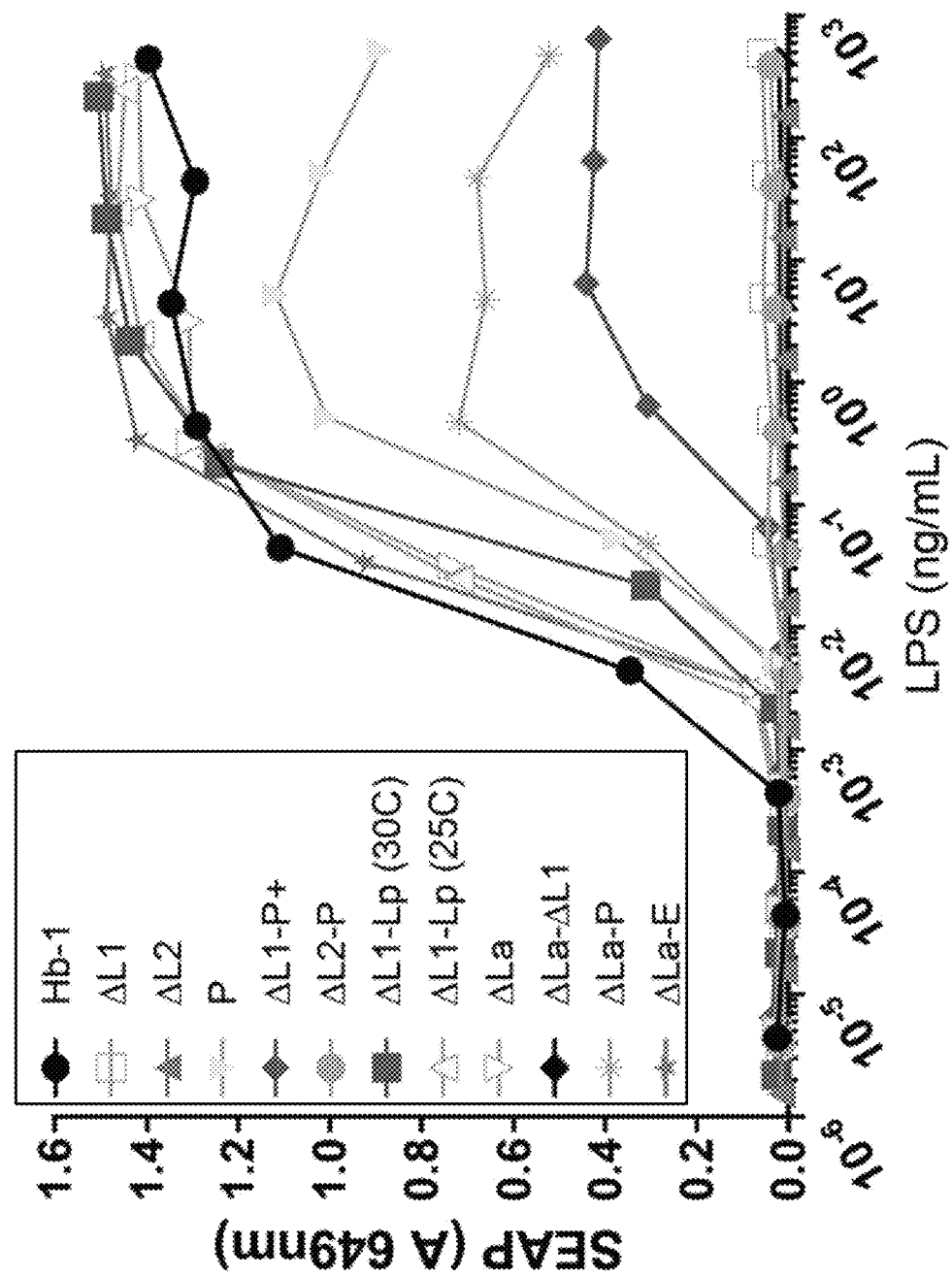

FIG. 3. TLR4 activation by purified LPS structures. HEK-blue hTLR4 cells were stimulated with 10-fold serial dilutions of 12 different LPS structures. TLR4 activation was measured by detection of secreted alkaline phosphatase. Data are representative results from three independent experiments and are depicted as the mean values of triplicates.

FIG. 4. Cytokine release of MM6 cells stimulated with purified LPS structures. MM6 cells were incubated with 10-fold serial dilution of different LPS structures for 20 h. IL-6 (A), IP-10 (B), IL-10 (C), MCP-1 (D) production was measured by ELISA. IL-6 and IL-10 are considered MyD88 dependent cytokines and IP-10 and MCP-1 are more TRIF dependent. Cytokine levels of MM6 cells stimulated with 5 ng/ml LPS are also presented as percentages of the HB-1 strain (E) and cytokine ratios in concentration (F) and percentages (G). For the cytokine ratios (F+G) the background without LPS stimulation was subtracted. Data shown are depicted as the mean values of two independent experiments. Statistical significance was determined with a 2-way ANOVA test comparing against HB-1. *, p<0.05. Data are also presented in Tables 6 and 7.

EXAMPLES

1. Methods and Materials
1.1 Bacterial Strains and Plasmids

All mutants were created in a N. meningitidis H44/76 strain (HB-1) strain using plasmid pMF121, resulting in deletion of the capsular biosynthesis locus including the galE gene. N. meningitidis strains were grown on GC medium base (Difco) plates supplemented with IsoVitaleX, in a humid atmosphere containing 5% $CO_2$ at 37° C. For liquid culture, strains were grown in 36 mg/mL tryptic soy broth medium (Difco) in a conical flask at 37° C., shaken at 140 RPM. Required antibiotics were added to plate and liquid cultures (kanamycine 100 µg/ml, chlooramphenicol 3 µg/ml). The lpxL1 and lpxL2 mutants were obtained by transformation with a linearized PCRII plasmid (Invitrogen) carrying the genes with a kanamycine resistance cassette described by van der Ley et al. (15) or a pGem T easy plasmid (Promega) with the lpxL1 gene that has a deleted section replaced with a chloramphenicol (CAM) cassette. For the lptA mutant the gene was amplified by PCR from the H44/76 strain, cloned into a pGem T easy plasmid (Promega) and a kanamycine cassette was placed in the gene at the MunI restriction site. The plasmid was linearized by digestion with a restriction enzyme cleaving outside the gene and transformed into the N. meningitidis H44/76 (HB-1) strain. N. meningitidis derivatives carrying the genes pagL, lpxP and lpxE were created using a pEN11 plasmid previously described for the expression of the Bordetella bronchiseptica pagL gene (13, 18). To obtain lpxP and lpxE derivatives the pagL gene in the pEN11 plasmid was replaced with the lpxP or lpxE gene amplified by PCR from E. coli and B. bronchiseptica, respectively. Expression of the genes on the pen 11 plasmid was induced by addition of 1 mM isopropyl-β-D-thioglactopyranoside (IPTG) and CAM (3 µg/ml) to the liquid culture medium. Primers are listed in Table 1.

TABLE 1

PCR primers used in the construction of the mutant strains

| Primer | Sequence (5'-3') | Source | SEQ ID NO |
|---|---|---|---|
| LptA Fw | GCCTTCCTTTCCCTGTATTC | N. meningitidis | 11 |
| LptA Re | GGTGTTCGGACACATATGC | N. meningitidis | 12 |
| LpxL1 Fw | CTGATCGGGCAGATACAG | N. meningitidis | 13 |
| LpxL1 Re | GTGCGCTACCGCAATAAG | N. meningitidis | 14 |
| LpxL2 Fw | AAACAGATACTGCGTCGGAA | N. meningitidis | 15 |
| LpxL2 Re | CCCTTTGCGAACCGCCAT | N. meningitidis | 16 |
| PagL Fw | ATGCAATTTCTCAAG | B. bronchiseptica | 17 |
| PagL Re | TCAGAACTGGTACGT | B. bronchiseptica | 18 |
| LpxP Fw | CATATGGCCGCTTACGCAGACAATACAC | E. coli | 19 |
| LpxP Re | GACGTCACGCCTGAATGACTTCATTACACC | E. coil | 20 |
| LpxE Fw | CATATGATCCGGCCCTCATCCCATTCCC | B. bronchiseptica | 21 |
| LpxE Re | TCATGACCCGAAAGGCGCTTCCCTTCAG | B. bronchiseptica | 22 |

1.2 LPS Isolation

LPS from bacterial mutants was extracted with hot phenol-water (19) and purified further by solid phase extraction (SPE) on reverse phase cartridges. In short, cells from 50 ml of bacterial culture with an $OD_{600nm}$ of 1.4 (or 100 ml of the ΔlpxL1-lpxP mutant grown at 30° C.) were collected by centrifugation at 2,739×g for 1 h at 20° C. Then, bacteria were suspended in 20 ml of water and centrifuged at 2,739×g for 25 min at 20° C. For hot phenol-water extraction, bacterial pellets were suspended with 4 ml of water, heated to 70° C., mixed with 3.2 ml of phenol at the same temperature and kept under agitation for 10 min at 70° C. The aqueous phase was separated from the phenolic phase by centrifugation at 2,739×g for 15 min at 20° C. After transferring the aqueous phase to a new vial, the phenolic phase was extracted again by adding 3 ml of water at 70° C. and repeating the extraction procedure. The aqueous phases from two consecutive extractions were pooled (~6.5 ml) and prepared for SPE by adding 5 ml of 0.356 M triethylammonium acetate (TEAA) pH 7 (solvent A) and 3.8 ml of 2-propanol:water:triethylamine:acetic acid (70:30:0.03:0.01, v/v) pH 8.7 (solvent B). In total, ten LPS extracts each from a different bacterial mutant could be purified simultaneously by SPE on reverse phase Sep-Pak C18 cartridges (1 ml syringe-barrel-type Vac cartridge, 50 mg of C18 resin, Waters) using a 20-position vacuum manifold (Waters). Cartridges were conditioned for SPE by applying consecutively 1 ml of 2-propanol:water:triethylamine:acetic acid (85:15:0.015:0.005, v/v) pH 8.7 (solvent C), 0.07 mM TEAA pH 7 (solvent D) and solvent A under vacuum. Then, samples were split into two aliquots of equal volume and each aliquot was applied into a different cartridge. Next, cartridges were washed once with 1 ml of solvent A and twice with 1 ml of 20% (v/v) solvent B in solvent D. LPS was eluted from the columns by applying 0.6 ml of solvent C. Eluates from the same sample were combined (1.2 ml per sample in total) and dried in a centrifugal vacuum concentrator (Concentrator plus, Eppendorf) at room temperature. LPS concentration in isolated samples was determined by the 3-deoxy-D-manno-oct-2-ulosonic acid (Kdo) assay (20). In addition, the purity and integrity of purified samples were judged by Tricine-SDS-PAGE using 1 mm-thick, 16% pre-cast Novex® mini-gels (Thermo Fisher Scientific Inc.), LPS silver staining (21) and protein visualization with Imperial™ Protein Stain (Thermo Scientific).

1.3 Mass Spectrometry

Electrospray ionization Fourier transform mass spectrometry (ESI-FT-MS) was performed on an LTQ Orbitrap XL instrument (Thermo Scientific) in negative ion mode. LPS samples were dissolved in a mixture of water, 2-propanol and triethylamine (50:50:0.001, by volume) pH 8.5 and infused into the mass spectrometer by static nano-ESI (22, 23). The MS instrument was calibrated with a Pierce Negative Ion Calibration Solution (Thermo Scientific) and internally with taurocholic acid following standard procedures provided by the manufacturer (Thermo Scientific). Fragmentation analysis of intact LPS was carried out by in-source collision-induced fragmentation (SID). Y- and B-type fragment ions, corresponding to the lipid A and oligosaccharide moieties of LPS, respectively, were generated by SID at a potential difference of 100 V. Fragment ions are annotated according to the nomenclature of Domon and Costello (24). Mass spectra were charge-deconvoluted using the Xtract tool of Thermo Xcalibur 3.0 software (Thermo Scientific). All mass values given refer to monoisotopic molecular masses. Proposed LPS compositions are based on the general chemical structure of the L3 immunotype LPS from *N. meningitidis* reported previously (25, 26).

1.4 Cell Stimulation

Mono Mac 6 cells were seeded at $1\times10^5$ cells per well in 96 well microtiter plates in 100 μl Iscove's modified Dulbecco's medium (IMDM) (Invitrogen) medium supplemented with 100 units/ml penicillin, 100 μg/ml streptomycin, 292 μg/ml l-glutamine (Invitrogen), and 10% fetal calf serum (Invitrogen). Hek blue-hTLR4 cells (Invivogen), a HEK293 cell line stably expressing human TLR4, MD-2 and CD14, were seeded at $3.5\times10^4$ cells per well in 96-well microtiter plates in 100 μl DMEM (Invitrogen) medium supplemented with 100 units/ml penicillin, 100 μg/ml streptomycin, 292 μg/ml l-glutamine (Invitrogen), and 10% fetal calf serum (Invitrogen). Cells were stimulated with 10-fold serial dilutions of LPS in IMDM (MM6 cells) or DMEM (HEK blue-hTLR4 cells) for 18-20 h at 37° C. in a humid atmosphere containing 5% $CO_2$. HEK-blue-hTLR4 cells were also stimulated with serial dilution of whole bacterial cells. Cytokine concentration in the supernatants of MM6 cells was determined by enzyme-linked immunosorbent assay (ELISA). All cytokine (IL-6, IL-1β, IP-10, MCP-1) concentrations were determined using a DUOset ELISA development kit (R&D systems) following the manufacturer's instructions. To quantify alkaline phosphatase secreted by HEK-blue-hTLR4 cells, 20 μl of the supernatant from each well was added to 200 μl Quanti-blue (Invivogen) and incubated at 37° C. for 2-3 hours. Read out was done on a spectrophotometer at 649 nm. Statistically significant differences were determined by the one-way (alkaline phosphatase secretion) or two-way (Cyokine release) ANOVA test by using GraphPad Prism 6.04 statistical software (GraphPad Software, Inc.).

2. Results

2.1 Bioengineering of Modified LPS Structures

LPS mutants in *N. meningitidis* were constructed in the HB-1 derivative of strain H44/76.The HB-1 strain is capsule deficient and has a galE deletion that results in truncation of the LPS oligosaccharide. Mass spectrometric analysis demonstrated that the HB-1 strain expresses a hexa-acylated, tri-phosphate, bis-phosphoethanolamine lipid A structure (see below). To construct a diverse set of LPS mutants in strain HB-1, we inactivated the autologous genes encoding for the LPS enzymes LptA, LpxL1 and LpxL2 and heterologously expressed the LpxE, LpxP and PagL LPS enzymes (see Table 2) by cloning the genes on the pen 11 plasmid behind a lac promotor.

TABLE 2

Overview of the inactivated the autologous genes encoding for the LPS enzymes LptA, LpxL1 and LpxL2 and heterologously expressed the LpxE, LpxP and PagL LPS enzymes.

| Enzyme | Abbr. | Activity | Source organism |
|---|---|---|---|
| LpxL1 | L1 | Adds $C_{12}$ to the primary linked acyl chain at 2'-position | *Neisseria meningitidis* |
| LpxL2 | L2 | Adds $C_{12}$ to the primary linked acyl chain at 2-position | *Neisseria meningitidis* |
| LpxE | E | Removes 1 phosphate group | *Bordetella bronchiseptica* |
| LpxP | Lp | Adds palmitoleate to the primary linked acyl-chain at 2'-position. | *Escherichia coli* |
| PagL | P | Removes acyl-chain from 3-position | *Bordetella bronchiseptica* |

TABLE 2-continued

Overview of the inactivated the autologous genes encoding for the LPS enzymes LptA, LpxL1 and LpxL2 and heterologously expressed the LpxE, LpxP and PagL LPS enzymes.

| Enzyme | Abbr. | Activity | Source organism |
|---|---|---|---|
| LptA | La | Adds phosphoethonalamine groups at 1 or/and 4'-position | *Neisseria meningitidis* |

In addition, combinations of deletion of autologous genes and expression of heterologous enzymes were constructed. This approach resulted in 11 LPS mutant strains as listed in Table 3.

For the expression of LpxE (Protein ID: CAE41138.1) we initially cloned an lpxE homologue from *Bordetella pertussis*. However, expression of the gene in HB-1 or its lptA mutant derivative did not result in any LPS structural changes as determined by mass spectrometry. As an alternative the lpxE (Genbank accession number: WP_003809405.1) homologue from *Bordetella bronchiseptica*, which exists as a pseudogene in *B. pertussis*, was cloned and expressed in a ΔlptA mutant strain. This resulted in the loss of a phosphate group in the lipid A and was included in our panel of LPS mutant strains (FIG. 1L).

LpxP (Genbank accession number: U49787.1), an enzyme known to add a secondary 9-hexadecenoic acid (C16:1) to the 2' acyl chain in *E.coli* (27), was expressed in the *N. meningitidis* ΔlpxL1 mutant strain, because the LpxL1 enzyme also adds a secondary acyl chain on the same position. This modification was done to create a hexa-acylated lipid A structure different from the original by carrying a longer C16 secondary acyl chain in the 2' position instead of C12. When LpxP was expressed in the ΔlpxL1 mutant strain at 37° C. this resulted in a very faint addition of C16:1. However, the C16:1 is added onto *E.coli* LPS only at 12° C., so for this reason we grew the bacteria at lower temperatures. Cultivation of meningococci below 25° C. is, unlike in *E. coli*, not possible, but at 25° C. and 30° C. we already found a much higher relative abundance of the LpxP hexa-acylated lipid A structure carrying the additional C16:1, with 25° C. resulting in the highest efficiency (at least 50% relative abundance) (FIG. 1H).

TABLE 3

Overview of the constructed LPS mutants in the *N. meningitidis* HB-1 strain

| Strain | Abbr. | Acylation | Phosphorylation | Phosphoethanolamine |
|---|---|---|---|---|
| HB-1 parent strain | | Hexa | Tris | Bis |
| ΔlpxL1 | ΔL1 | Penta | Tris | Bis |
| ΔlpxL2 | ΔL2 | Penta | Bis | Mono |
| pagL | P | Penta | Tris | Bis |
| ΔlpxL1-pagL | ΔL1-P | Tetra | Tris | Bis |
| ΔlpxL2-pagL | ΔL2-P | Tetra | Bis | Mono |
| ΔlpxL1-lpxP 37° C. | ΔL1-Lp37 | Hexa | Tris | Bis |
| ΔlpxL1-lpxP 30° C. | ΔL1-Lp30 | Hexa | Tris | Bis |
| ΔlpxL1-lpxP 25° C. | ΔL1-Lp25 | Hexa | Tris | Bis |
| ΔlptA | ΔLa | Hexa | Tris | None |
| ΔlptA-ΔlpxL1 | ΔLa-ΔL1 | Penta | Tris | None |
| ΔlptA-pagL | ΔLa-P | Penta | Tris | None |
| ΔlptA-lpxE | ΔLa-E | Hexa | Tris | None |

2.2 Mass Spectrometric Characterization of Modified LPS

The charge-deconvoluted ESI-FT mass spectra of intact LPS isolated from the constructed *N. meningitidis* mutants are shown in FIG. 1. The mass spectrum of LPS of the HB-1 (galE) parent strain (FIG. 1A), displayed an ion signal of 3408.507 u consistent with LPS comprised of wild-type hexa-acyl lipid A carrying three phosphate (P) and two phosphoethanolamine (PEA) groups and an L3-immunotype oligosaccharide structure substituted with a glycine (Gly) residue and truncated at the proximal galactose (Gal) of its alpha chain due to inactivation of the galE gene (Mcalc.=3408.514 u, see Supplemental Table 1 for LPS composition proposals). Accompanying ion peaks of 3351.488, 3285.501 and 3228.480 u (FIG. 1A) corresponded to LPS species which lack Gly (Δmeas.=−57.019 u), carry one less PEA group in the lipid A (Δmeas.=−123.006 u) or both (Δmeas.=−180.027 u), respectively. This chemical heterogeneity of the LPS from HB-1 (galE−) strain is likely caused by variation in lipid A phosphorylation and oligosaccharide non-stoichiometric substitution with glycine. Composition proposals based on mass spectra of intact LPS were additionally supported by FT-MS analysis of LPS fragment ions corresponding to lipid A and oligosaccharide moieties, which were generated by in-source collision induced dissociation (SID) of intact LPS. For instance, SID FT mass spectra of LPS from HB-1 (galE−) strain displayed fragment ions of 1916.098 and 2039.106 u corresponding to hexa-acyl lipid A species with 2 and 3 PEA groups (Mcalc.=1916.100 and 2039.109 u, respectively) and a fragment ion of 1369.404 u corresponding to the dehydrated derivative of the oligosaccharide moiety described above (Mcalc.=1369.406 u). Fragmentation analyses of LPS derived from other strains of *N. meningitidis* described here showed that different types of LPS carry the same oligosaccharide moieties ($PEA_1 \cdot Hex_1 \cdot Hep_2 \cdot HexNAc_1 \cdot Kdo_2 \cdot Gly_1$), with the exception of some LPS species, which lack a glycine or carry a second hexose residue (Hex) (Supplemental Table 2). Consequently, other differences observed between the LPS species, such as in the number of PEA and P groups, may be attributed to changes in the composition of the lipid A (Supplemental Table 2).

Analysis of the intact LPS from the ΔlpxL1 mutant revealed that he main ion peaks of the mass spectrum (3046.315, 3103.336, 3169.324 and 3226.342 u, FIG. 1B) had shifted compared to the 4 main ion signals of the LPS from the parent HB-1 (galE−) strain (FIG. 1A) by −182.165 u. This is in agreement with the lack of a dodecanoic acid (C12) (Δcalc.=−182.167 u) in the lipid A after deletion of the Δlpxl1 gene.

Comparative analysis of the mass spectrum of the LPS from the ΔlpxL2 mutant displayed ion peaks of 3023.367, 2966.348, 3185.419 and 3128.398 u (FIG. 1C), which are consistent with the loss of a C12 fatty acyl chain together with PPEA from the lipid A (Δcalc.=−385.142 u) in combination with non-stoichiometric substitution of the oligosaccharide with Gly (Δcalc.=−57.021 u) or a second hexose (Δcalc.=−162.053 u). This is in agreement with effective deletion of the lpxL2 gene. It is worthy to note that deletion of the lpxL2 gene not only led to the loss a C12 fatty acyl chain, as observed earlier upon deletion of the lpxL1 gene, but also resulted in the loss of a P and a PEA group from the lipid A.

The ion peaks in the mass spectrum of the LPS from the pagL mutant (3210.345, 3153.325, 3087.338 and 3030.318 u, FIG. 1D) were found to be shifted by −198.163 u from the 4 main ion peaks of the LPS from the parent HB-1 strain. This is in agreement with efficient removal of a 3-hydroxy-dodecanoic acid (C12OH) (Δcalc.=−198.162 u) from the lipid A by the PagL enzyme. Nonetheless, display of minor ion peaks of 3408.505 and 3351.485 u (FIG. 1D) corresponding to unmodified hexa-acyl LPS species indicated that LPS 3-O-deacylation activity of the PagL enzyme could not fully exhaust the hexa-acyl lipid A substrate.

The 4 main ion signals in the mass spectrum of the LPS from the ΔlpxL1-pagL mutant (3028.180, 2971.160, 2905.173 and 2848.152 u, FIG. 1E) differed by -380.328 u from the 4 main ion signals of the LPS from the HB-1 strain, which is accordance with lack of a C12 and a C12OH in the lipid A of the ΔlpxL1-pagL mutant (Δcalc.=-380.329 u). The absence of ion signals corresponding to LPS carrying two C12 acyl chains indicates that the deletion of the lpxL1 gene resulted in complete removal of a single C12 from the lipid A (see Supplemental Table 1 for detailed LPS composition proposals). In contrast, minor ion signals of 3226.339 and 3169.319 u were present in the mass spectrum of the LPS from the ΔlpxL1-pagL mutant, which correspond to penta-acyl LPS species carrying two C12OH acyl chains. This indicates that a low level of LPS molecules was not 3-O-deacylated by the PagL enzyme.

The mass spectrum of the LPS from the ΔlpxL2-pagL mutant showed an ion peak of 2825.206 u (FIG. 1F) that was shifted by -583.301 u from the ion signal of 3408.507 u of the mass spectrum of the LPS from the parent HB-1 strain (FIG. 1A). This fits the expected loss of a C12OH, a C12 and PPEA from the lipid A (Δcalc.=-583.304 u). Other ion signals of 2768.187, 2930.236 and 2987.257 u (FIG. 1F) are consistent with non-stoichiometric substitution of the oligosaccharide with Gly or a second Hex.

Comparison of the mass spectrum of the LPS from the ΔlpxL1-lpxP mutant grown at 30° C. (FIG. 1G) with that of the LPS from the ΔlpxL1 mutant (FIG. 1B) revealed that the LPS from the ΔlpxL1-lpxP mutant contained not only the main LPS species that were present in the LPS from the ΔlpxL1 mutant (3046.315, 3103.333, 3169.322 and 3226.340 u, FIG. 1G), corresponding to penta-acyl LPS lacking a C12, but also LPS species (3282.524, 3339.543, 3405.533 and 3462.553 u, FIG. 1G) that shifted in the spectrum to higher mass values by 236.211 u. This is in agreement with incorporation of a 9-hexadecenoic acid (C16:1) to the lipid A. Therefore, this preparation comprised a mixture of penta-acyl LPS that lacks a C12 and hexa-acyl LPS that lacks a C12 and additionally carry a C16:1.

The mass spectrum of the LPS from the ΔlpxL1-lpxP mutant cultured at 25° C. (FIG. 1H) showed ion signals corresponding to hexa-acyl LPS lacking a C12 and carrying additionally a C16:1 (3282.526, 3339.546, 3405.535 and 3462.554, FIG. 1H), which were of a higher relative abundance as compared to the same signals in the spectrum of the LPS from the ΔlpxL1-lpxP mutant grown at 30° C. Furthermore, other ion peaks corresponding to hexa-acyl LPS carrying a C16:1 were displayed which arose from elongation of the oligosaccharide with a second Hex (3624.608 u) or the latter in combination with the loss of Gly substitution (3567.586 u) and the loss of a PEA group from the lipid A (3501.596 u) (FIG. 1H).

The ion peak of 3162.489 u in the mass spectrum of the LPS from the ΔlptA mutant (FIG. 1I) differed by -246.018 u from the ion signal of 3408.507 u of the mass spectrum of the LPS from the parent HB-1 strain (FIG. 1A). This points to the loss of two PEA groups from the lipid A (Δcalc.=-246.017u). Other ion signals corresponded to LPS species that in addition to lacking PEA in the lipid A either lacked Gly in the oligosaccharide (3105.471), contained a second Hex in the oligosaccharide (3324.541) or contained a second Hex and lacked Gly in the oligosaccharide (3267.521 u) (FIG. 1I).

The mass spectrum of the LPS from the ΔlptA-ΔlpxL1 mutant displayed ion peaks of 2980.324, 2923.307, 3142.375 and 3085.354 u indicating the loss of 2PEA and a C12 from the lipid A (Δcalc.=-428.184 u) combined with non-stoichiometric substitution of the oligosaccharide with Gly or a second Hex (FIG. 1J). In addition, MS/MS spectra of the main lipid A fragment ion produced by in-source collision-induced dissociation of LPS were consistent with the presence of a P group at both the 1 and 4'positions of the lipid A (data not shown). Therefore, the activity of the LpxE enzyme consisted in removal of one of the three P groups present in lipid A producing bisphosphorylated lipid A species with a P group on each side of the diglucosamine backbone.

The main ion signals of the mass spectrum of the LPS from the ΔlptA-pagL mutant (2964.328 and 2907.311 u, FIG. 1K) are consistent with the loss of 2PEA and a C12OH from the lipid A (Δcalc.=-444.179 u) together with non-stoichiometric substitution of the oligosaccharide with Gly (Δcalc.=57.021 u). Minor ion peaks of 3105.468 and 3162.488 u were observed corresponding to hexa-acyl LPS species which lost only 2PEA from the lipid A, indicating a low level of incomplete LPS 3-O-deacylation by the PagL enzyme.

Finally, the mass spectrum of the LPS from the ΔlptA-lpxE mutant showed 2 main ion peaks of 3082.525 and 3025.508 u consistent with loss of 2PEA and P from the lipid A (Δcalc.=-325.983 u) in combination with non-stoichiometric substitution of the oligosaccharide with Gly (FIG. 1L).

2.3 TLR4 Stimulation by the LPS Mutant Strains

To determine the scope of TLR4 activation by the entire set of lipid A mutant structures, an initial screening was done using HEK-Blue humanTLR4 cells. These cells express human TLR4, MD-2, and CD14 and contain a nuclear factor kappa-light-chain-enhancer of activated B cells (NF-κB) and activator protein 1 (AP-1) dependent secreted embryonic alkaline phosphatase (SEAP) reporter gene. Stimulation of cells with serial dilutions of the different LPS mutants yielded a wide range of TLR4 activities (FIG. 2 and Table 5), with HB-1 inducing strongest TLR4 activation and ΔLpxL2 bacteria yielding lowest levels of activation. The other LPS mutants showed intermediate TLR4 stimulating activity (FIG. 2). A particularly notable result was that the absence of phosphoethanolamine in the ΔlptA strain resulted in reduced TLR4 activation both in the hexa-acylated wild type strain and the penta-acylated ΔlpxL1 and pagL backgrounds. Induction of LpxE in the ΔlptA strain showed similar TLR4 activation as ΔlptA strain, which was slightly less than the HB-1 wild type strain. This indicates that the reduction of three phosphates to two in the lipid A structure with one phosphate on each side of the diglucosamine backbone did not affect TLR4 signalling.

Expression of LpxP at 25° C. in combination with deletion of LpxL1 resulted in a heterogeneous hexa- and penta-acylated structure-LPS expressing strain with a slightly reduced TLR4 activating potential compared to the wild type bacteria. Cultivation of this strain at 30° C. resulted in less hexa-acylated lipid A and even slightly less TLR4 activity.

Surprisingly, when the ΔlpxL1 strain was combined with expression of PagL, reducing the penta-acylated lipid A structure to a tetra-acylated lipid A structure, an increase of TLR4 activity was obtained. This was unexpected as tetra-acylated lipid A structures typically acts as a TLR4 antagonists as reported for *E. coli* lipid Iva (7, 9, 28).

2.4 Human TLR4 Stimulation using Purified Mutant LPS

We also purified LPS from all strains and used them to stimulate HEK-Blue TLR4 cells to confirm our initial findings with whole bacteria. Purified LPS generally yielded similar results as those obtained with intact bacteria although purified LPS, ΔlpxL1, ΔlptA-ΔlpxL1, ΔlpxL2 and ΔlpxL2-pagL showed almost no induction of TLR4 activity and were barely distinguishable from each other (FIG. 3), whereas the bacteria these variants displayed low but distinct TLR4 activities above the background. In addition, a higher concentration of purified penta-acylated pagL LPS was needed for activation of TLR4 than with all the hexa-acylated LPS derivatives, but with whole bacteria stimulation, a lower absorption density was necessary for the pagL strain to induce TLR4 activity than the other hexa-acylated mutant strain (FIGS. 2+3). However, the maximum amount of alkaline phosphatase secretion was still lower for the pagL mutant strain compared to the hexa-acylated mutant strains. Of note, the three LPS mutants ΔlpxL1-pagL, pagL and ΔlptA-pagL had substantially reduced activating capabilities when compared to the wild type LPS, but still induced activation above the background level of unstimulated cells (FIG. 3).

2.5 Cytokine Induction by the Purified Mutant LPS

Figure 4C:
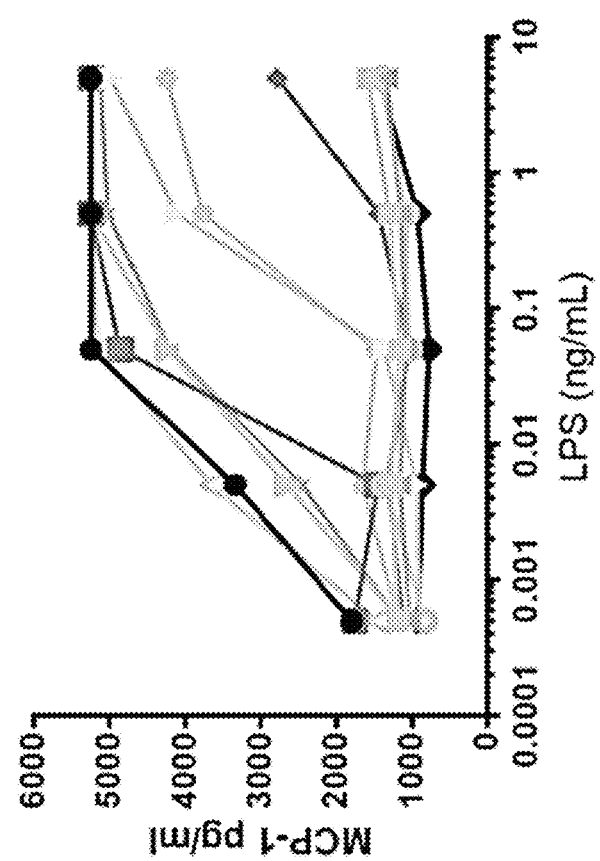
Figure 4D:
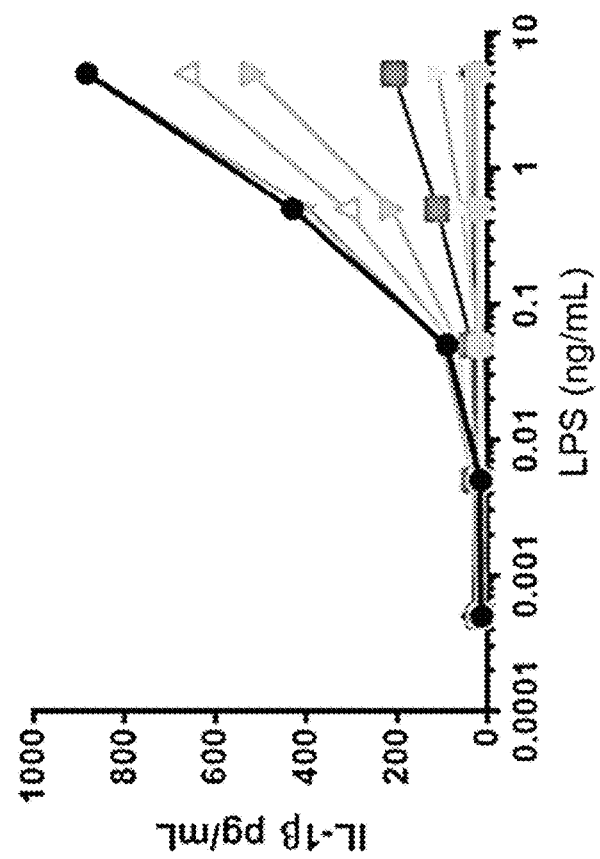
Figure 4E:
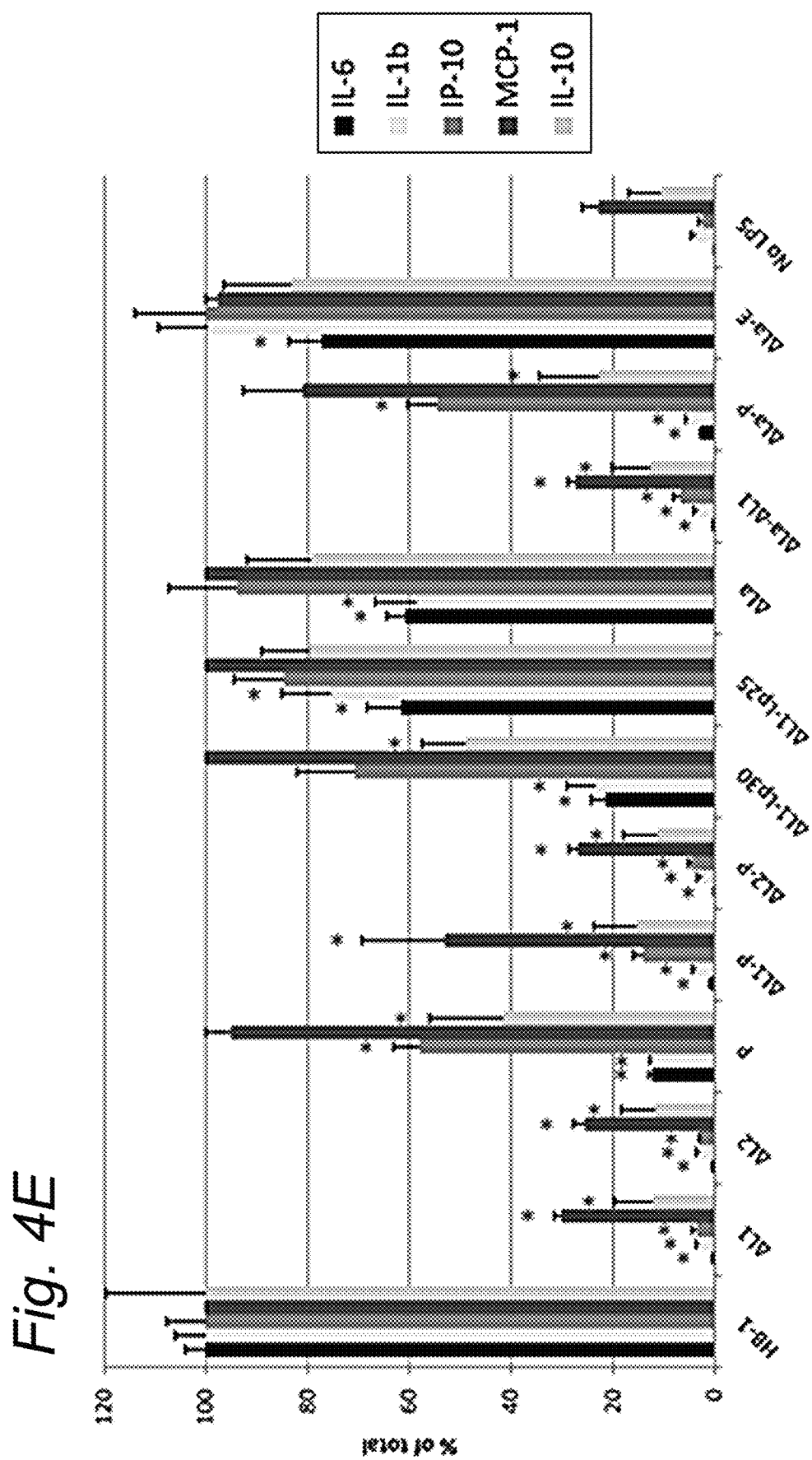
Figure 4F:
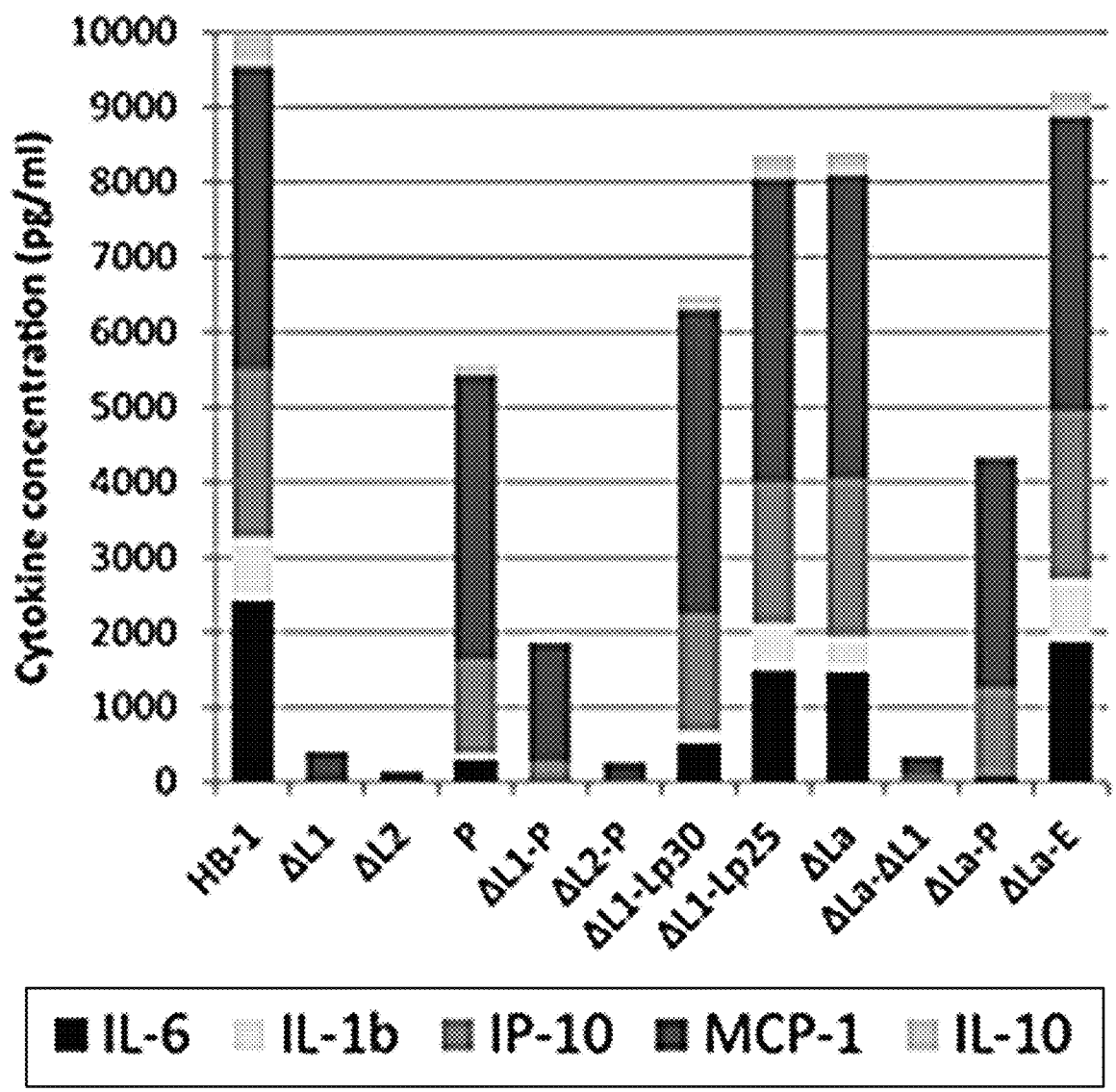
Figure 4G:
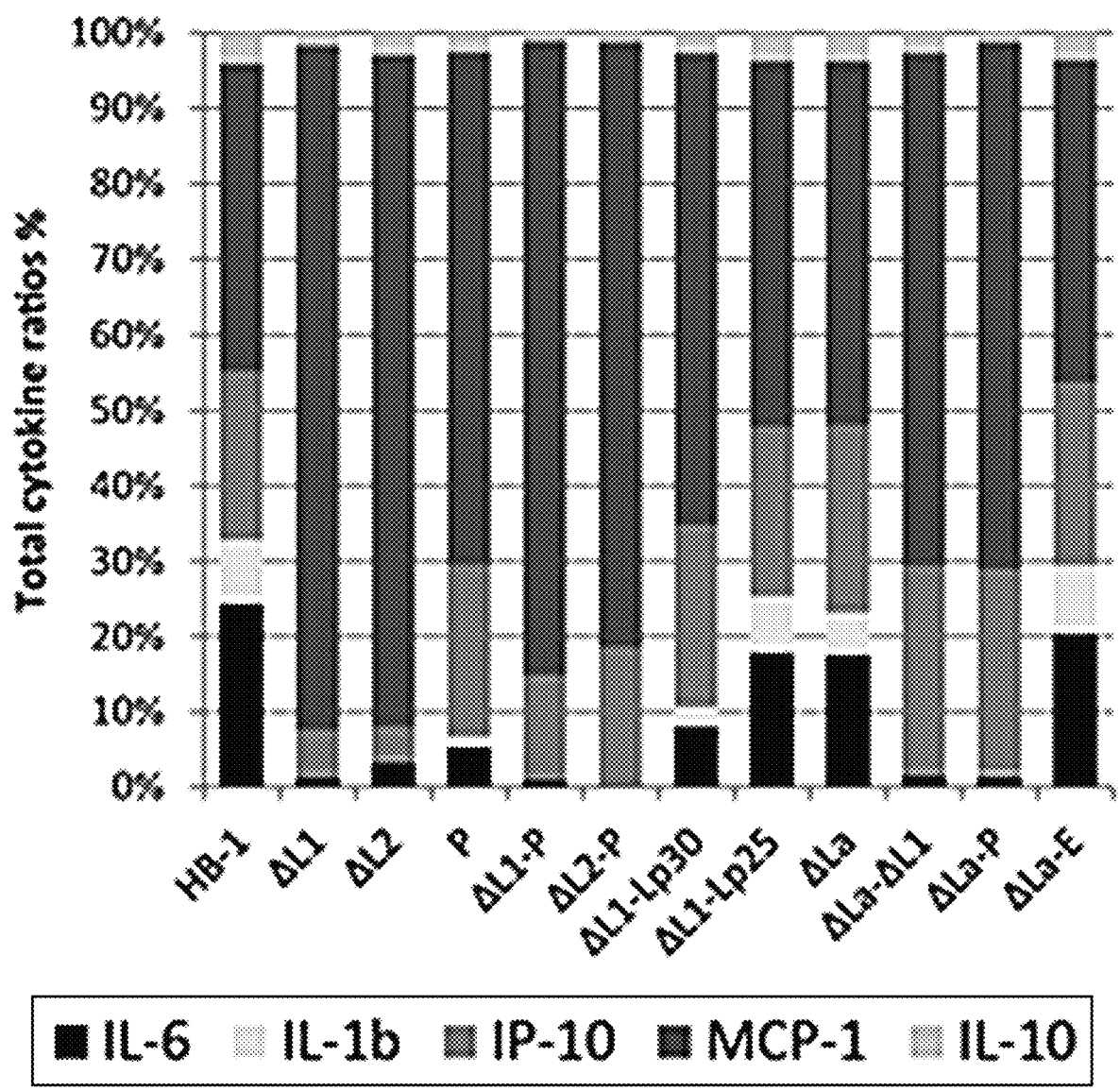

The cytokine induction profile of the modified LPS structures was investigated in the human monocytic cell line Mono Mac 6 (MM6). The concentration of secreted MyD88 dependent cytokines IL-6 (FIG. 4A and Table 6A) and IL-1β (FIG. 4BA and Table 6B) and TRIF dependent cytokines interferon gamma-induced protein 10 (IP-10) (FIG. 4C and Table 6C) and monocyte chemotactic protein-1 (MCP-1) (FIG. 4D and Table 6D) were determined after 20 h of stimulation with purified LPS (FIG. 4E, F and G, and Table 7). The possible contribution of minor protein contamination in LPS samples to the observed responses was excluded as activation of a HEK-hTLR2 cell line by the LPS samples was negligible in the range of LPS concentrations tested (data not shown).

A wide variety of cytokine levels was determined from the different LPS structures, with the highest levels being produced by the HB-1 wild type hexa-acylated LPS and all other LPS ranging from close to wild type until virtually zero cytokine induction as seen for ΔlpxL2 LPS. Besides quantitative differences in cytokine induction, we also observed qualitative differences with LPS structures causing reduced levels of certain cytokines, but still capable of producing others. Some examples are pagL and ΔlptA-pagL LPS, which displayed a reduced capacity to induce the production of MyD88 dependent pro-inflammatory cytokines IL-6 and IL-1β only inducing 10% and 25% of the levels induced by wild-type LPS, respectively, but retained most of the ability to induce the secretion of TRIF dependent IP-10 (50%) and MCP-1 (90%). Interestingly, differences were observed between ΔlpxL1-lpxP grown at 30° C. and 25° C., with ΔlpxL1-lpxP grown at 30° C. producing 30-40% IL-6 and IL-1β and 60-85% of those cytokines at 25° C., whereas IP-10 and MCP-1 induction were similar. These results emphasize how LPS bioengineering can provide a wide range of agonists to fine-tune cytokine release.

3. Discussion

Although LPS has great potential as an adjuvant, adverse effects keep being a concern. Finding the optimal balance between adjuvant activity and minimal toxic effects requires the development of new LPS derivatives. Here we report a collection of novel meningococcal LPS structures inducing a broad range of TLR4 responses and differential cytokine patterns. These combinatorial bioengineered LPS mutants can be used as part of a whole cell vaccine, OMV vaccine or as purified LPS or lipid A molecule. OMVs of N. meningitidis are being actively investigated as potential vaccines and have been already approved for use in humans as a component of the Bexsero vaccine against serogroup B meningococcal disease (29,30). Attenuated ΔlpxL1 LPS is under investigation as constituent of meningococcal OMV vaccines and is a safe method to detoxify OMVs (16,31). In addition, in an immunization study purified ΔlpxL1 LPS retained similar adjuvant activity compared to wild type meningococcal LPS, but with reduced toxicity (15).

The modified LPS molecules LpxL1, LpxL2 and PagL all result in a reduced TLR4 activity compared to the parent strain (13,15). This was expected because they reduce the number of acyl chains in LPS from hexa to penta. Surprisingly, the expectation that tetra-acylated LPS is always less active than penta-acylated LPS is challenged by our results. Tetra-acylated lipid IVa of E. coli is a known antagonist of the human TLR4/MD-2 complex (7, 9, 28). Yet, we show that meningococcal tetra-acylated ΔlpxL1-pagL LPS is more active than the penta-acylated ΔlpxL1 LPS, whereas tetra-acylated ΔlpxL1-ΔlpxL2 LPS did not yield detectable activity (data not shown). Stimulation with ΔlpxL2-pagL whole bacteria that also carry a tetra-acylated LPS again increased TLR4/MD-2 activity compared to its penta-acylated ΔlpxL2 parent strain, although purified LPS from both the ΔlpxL2-pagL and ΔlpxL2 were inactive. Together these findings indicate that removal of C12OH from the 3'position by PagL in combination with deletion of a secondary acyl chain resulting in tetra-acylated lipid A yields a higher TLR4 activity compared to sole removal of the secondary acyl chain or both secondary acyl chains.

Interestingly, introduction of LpxP from E. coli into N. meningitidis conferred temperature-sensitive lipid A modification to N. meningitidis. Since conservation of temperature-sensitive gene expression signals is unlikely, this means that the enzyme itself is most active at lower temperatures. Selection of a temperature of 25 or 30° C. for culture of the ΔlpxL1-lpxP strain influenced the amount of hexa-acylated LPS species present in the mixture of penta- and hexa-acylated LPS produced by this mutant, with the lower temperature leading to the highest degree of substitution. The temperature sensitivity of the LpxP enzyme thus enables to prepare penta- and hexa-acylated LPS mixtures in a controlled manner. By selecting the time and/or temperature that the mutant strain is grown, it is feasible to increase or decrease the amount of hexa-acylated lipid A structure and thereby the TLR4 activity and cytokine profile. This provides a new approach of fine-tuning the immunological properties of meningococcal OMV vaccines.

In addition, we have obtained new insight in the specificity of the LpxE enzyme. Previously, the lpxE gene from Francisella tularensis or Francisella novicida expressed in E. coli was shown to be specific for the removal of the P group in the 1'position (32, 33). We have found that the lpxE homologue from B. bronchiseptica removed only one P group from the total of three present in the lipid A of N. meningitidis. MS/MS spectra of the lipid A from ΔlptA-lpxE mutants were consistent with the presence of a P group at both the 1 and 4'positions of the lipid A. In addition, removal of the P group was only seen in double ΔlptA-lpxE mutants, therefore only in the absence of PEA substitution of the lipid A. Thus, it is likely that the presence of PEA prevents lpxE from removing the P group. Most likely, the newly described LpxE enzyme is a pyrophosphatase, only catalysing hydrolysis between two phosphate groups. The absence of PEA in the lipid A through deletion of the lptA gene resulted in a reduced TLR4/MD-2 activity. This concurs with earlier observations by John et al. (34) that show a significant reduction of TNFα release by THP-1 cells upon stimulation with LptA lacking strains. Here we showed that reduction of the activity is even more apparent when stimulated with penta-acylated ΔlptA-pagL LPS or whole bacteria.

Interestingly, our results indicate that the absence of 2' C12 fatty acyl chain by deletion of LpxL2 is accompanied by removal of a single P group and PEA group. This was previously not observed due to isolation of lipid A by an acid hydrolysis method before mass spectrometric analysis, which can result in the loss of P groups from the lipid A (15). In the present study, we used complete LPS molecules without introducing any deleterious chemical modifications for mass spectrometric analysis, giving us the possibility to observe new phosphorylation changes of the lipid A.

Several of the constructed attenuated LPS structures did not only need a higher concentration to induce TLR4 stimulation, but also did not yield the level of activation observed for the parent strain. This was most apparent for pagL LPS. The reason for this phenomenon is unclear, but could be due to instable dimerization of the LPS-TLR4-MD2 receptor complex at the cell surface but stable dimerization inside the cell, and/or to a less stable dimerization with high concentrations of the particular LPS. In addition, certain LPS species showed no activation at all and could potentially have antagonistic features, and might therefore serve as a TLR4 blocking drug. Indeed, meningococcal ΔlpxL1 and pagL penta-acylated LPS can block the TLR4 response when administered together with hexa-acylated wild type meningococcal LPS (13).

In the present study, we have used combinatorial bioengineering in meningococci to produce a range of LPS species with a broad array of TLR4 activity and cytokine profile. The application of these structures can be very broad, from inclusion into vaccines as adjuvants to their use in various forms of immunotherapy which have been described or suggested for LPS, such as cancer therapy, Alzheimer's disease or generalized immune stimulation to prevent diverse infections (3, 35-37).

TABLE 4

Multiple sequence alignment of the LpxP proteins. Sequences were aligned using ClustalW (2.1) (clustalw.ddbj.nig.ac.jp/) using default settings and the Gonnet protein weight matrix. Hyphens indicate gaps introduced for optimal alignment. Absolutely conserved residues are marked with asterisks. Colons and dots indicate strongly and weakly conserved residues, respectively. Sequences are from Escherichia coli (Genbank AAB66658), Citrobacter youngae (Genbank EFE09970), Haemophilus aegyptius (Genbank EGF15820), Klebsiella sp. (Genbank EFD82732), Salmonella enterica subsp. enterica serovar Typhimurium (Genbank CBW18471), Serratia plymuthica (Genbank EKF62147) and Shigella flexneri (Genbank ADA74790).

```
AAB66658    MFPQ--CKFSREFLHPRYWLTWFGLGVLWLWVQLPYPVLCFLGTRIGAMARPFLK--RRE   56
ADA74790    MFPQ--CKFSREFLHPRYWLTWFGLGVLWLWVQLPYPVLCFLGTRIGAMARPFLK--RRE   56
CBW18471    MFPQ--SKFSRAFLHPRYWLTWFGVGILWLLVQLPYPVLRFLGTRTGKLARPFLK--RRE   56
EFE09970    MFPQ--CKFSRAFLHPRYWLTWFGVGVLWLLVQLPYPLLCFLGTRTGTLARPFLK--RRE   56
EFD82732    --MA--CVFNKQLLHPRNWLTWFGLGILWLIVQLPYPLLHFIGTSAGRLSRRFLK--RRE   54
EKF62147    MKRP--QEFRSALLHPRYWFTWFGLAILFLLVQLPYPLLHKLGVWMGRTSMRFLK--RRV   56
EGF15820    MKNEKLPQFQPHFLVPKYWLFWLGVAIWRSILCLPYPILRHIGHGLGWLFSHLNEGKRRA   60
                 :*  *: *: *:*:..  : ****:*  :*   *    :  :  **

AAB66658    SIARKNLELCFPQHSAEEREKMIAENFRSLGMALVETGMAWFWPDSRVRKWFDVEGLDNL   116
ADA74790    SIARKNLELCFPQHSAEEREKMIAENFRSLGMALVETGMAWFWPDSRVRKWFDVEGLDNL   116
CBW18471    SIAQKNIELCFPTLSREEREKLIAENFHSLGMALLETGMAWFWPDSRVRKWFDVDGLDNL   116
EFE09970    SIARKNLELCFPNLSQEERDKLVDENFRSLGMGLLETGMAWFWPDRRVRKWFDVEGLDNL   116
EFD82732    HIARRNIELCFPDMSPAARETLIDQNFMSLGMGLIETGMAWFWSDERVKKWFDVEGFANL   114
EKF62147    AITRRNLELCFPDMDEAQRERKVIGNFESLGMGLLETGMAWFWSDKRVKRWFNVSGINHL   116
EGF15820    AIARRNLELCFPYMPENERETILQENLRSVGMAIIETGMAWFWSDSRIKKWSKVEGLHYL   120
             *::*:*****        *:   :  *: *:**.::********.* *:::* .*.*:  *

AAB66658    KRAQMQNRGVMVVGVHFMSLELGGRVMGLCQPMMATYRPHNNQLMEWVQTRGRMRSNKAM   176
ADA74790    KRAQMQNRGVMVVGVHFMSLELGGRVMGLCQPMMATYRPHNNQLMEWVQTRGRMRSNKAM   176
CBW18471    TRAQAQNRGVMVVGVHFMSLELGGRVMGLCQPMMATYRPHNNPLMEWVQTRGRMRSNKAM   176
EFE09970    QRAQIEGRGVMVVGVHFMSLELGGRVMGLCQPTMATYRPHNNKLMEWIQTRGRMRSNKAM   176
EFD82732    NHALSGGKGVMVVGVHFMSLELGGRAMGLCRPMMATYRPHNSPLMEWVQTRGRLRSNKAM   174
EKF62147    KMAQQNERGVLVIGVHFMSLELGGRAMGLCQPMMAMYRPHNNKAMEWAQTKGRMRSNKAM   176
EGF15820    KENQKD--GIVLVGVHFLTLELGARIIGLHHPGIGVYRPNDNPLLDWLQTQGRLRSNKDM   178
             *::::*****::****.*  :**  :*  :.  ***::.    ::* **:**:**** *

AAB66658    IGRNNLRGIVGALKKGEAVWFAPDQDYGRKGSSFAPFFAVENVATTNGTYVLSRLSG-AA   235
ADA74790    IGRNNLRGIVGALKKGEAVWFAPDQDYGRKGSSFAPFFAVENVATTNGTYVLSRLSG-AA   235
CBW18471    IGRNNLRGIVGALKKGEAVWFAPDQDYGRKGSSFAPFFAVENVATTNGTYVLSRLSG-AA   235
EFE09970    IGRNNLRGIVGALKKGEAVWFAPDQDYGRKGSSFAPFFAVKDVATTNGTYVLSRLSG-AA   235
EFD82732    IDRNNLTGLVHALKSGEAVWFAPDQDYGPKGSVFAPFFSVPQAATTNGTYVLSRLSG-AK   233
EKF62147    LDRKDLRGMVHALKRGEAVWFAPDQDYGPRGSVFAPLFAVDQAATTSGTFMLARMAK-PA   235
EGF15820    FDRKDLRGMIKALRHEETIWYAPDHDYGRKNAVFAPFFAVPDACTTTGSYYLLKSSQNSK   238
             :.*::*  *::  **:   *::*:***:***  :.: ***:*:*  :..**.*::  *   :   .

AAB66658    MLTVTMVRKADYSGYRLFITPEMEGYPTDENQAAA-YMNKIIEKEIMRAPEQYLWIHRRF   294
ADA74790    MLTVTMVRKADYSGYRLFITPEMEGYPTDENQAAA-YMNKIIEKEIMRAPEQYLWIHRRF   294
CBW18471    MLTVTMVRKSDNSGYRLYITPEMEGYPADENQAAA-YMNKIIEKEIMRAPEQYLWIHRRF   294
EFE09970    MLTVTMVRKADNSGYRLFITPQMEGYPADESQAAA-YMNKIIEKEIMRAPEQYLWIHRRF   294
EFD82732    MLSISMVRKLDRQGYSLHISEVMNDYPGEDKQIAAGYINKVIEREILRAPEQYLWVHRRF   293
EKF62147    LVPVVLIRREKGRGYDLLIQPALEDYPIGDELAAAAYMNKVVEKEIMRAPEQYMWLHRRF   295
EGF15820    VIPFAPLRNKDGSGYTVSISAPVDFTDLQDETAIATRMNQIVEKEIMKGISQYMWLHRRF   298
             ::..   :*.  . **  : *   ::      :.   *   :*::*:**::. .**:*:****
```

TABLE 4-continued

Multiple sequence alignment of the LpxP proteins. Sequences were aligned using ClustalW (2.1) (clustalw.ddbj.nig.ac.jp/) using default settings and the Gonnet protein weight matrix. Hyphens indicate gaps introduced for optimal alignment. Absolutely conserved residues are marked with asterisks. Colons and dots indicate strongly and weakly conserved residues, respectively. Sequences are from *Escherichia coli* (Genbank AAB66658), *Citrobacter youngae* (Genbank EFE09970), *Haemophilus aegyptius* (Genbank EGF15820), *Klebsiella* sp. (Genbank EFD82732), *Salmonella enterica* subsp. *enterica* serovar Typhimurium (Genbank CBW18471), *Serratia plymuthica* (Genbank EKF62147) and *Shigella flexneri* (Genbank ADA74790).

| | | | |
|---|---|---|---|
| AAB66658 | KTRP-VGESSLYI | 306 | (SEQ ID NO: 4) |
| ADA74790 | KTRP-VGESSLYI | 306 | (SEQ ID NO: 10) |
| CBW18471 | KTRP-LGEASLYI | 306 | (SEQ ID NO: 8) |
| EFE09970 | KTRP-MGEASLYI | 306 | (SEQ ID NO: 5) |
| EFD82732 | KTRP-LGEPSVY- | 304 | (SEQ ID NO: 7) |
| EKF62147 | KTRP-IGAPSLY- | 306 | (SEQ ID NO: 9) |
| EGF15820 | KTRPDEKTPSLYD | 311 | (SEQ ID NO: 6) |
| | ****    .*:* | | |

TABLE 5

TLR4 activation by *N. meningitidis* strains (the same data are graphically presented in FIG. 2A). HEK-blue hTLR4 cells were stimulated with 5-fold serial dilutions at A600 nm (y-axis) of heat-inactivated *N. meningitidis* for 20 h. TLR4 activation was measured by detection of secreted alkaline phosphatase at A649 nm. Data are expressed as mean values of three independent experiments.

| A600 nm | HB-1 | ΔL1 | ΔL2 | P | ΔL1-P | ΔL2-P | ΔL1-Lp37 | ΔL1-Lp30 | ΔL1-Lp25 | ΔLa | ΔLa-ΔL1 | ΔLa-P | ΔLa-E |
|---|---|---|---|---|---|---|---|---|---|---|---|---|---|
| 0.01 | 1.102 | 0.318 | 0.124 | 0.715 | 0.596 | 0.277 | 0.534 | 1.070 | 1.011 | 0.874 | 0.157 | 0.501 | 0.911 |
| 0.002 | 1.083 | 0.247 | 0.092 | 0.692 | 0.569 | 0.199 | 0.450 | 0.967 | 0.964 | 0.855 | 0.098 | 0.469 | 0.872 |
| 0.0004 | 1.093 | 0.187 | 0.096 | 0.703 | 0.536 | 0.172 | 0.340 | 0.925 | 0.974 | 0.856 | 0.090 | 0.431 | 0.915 |
| 0.00008 | 1.031 | 0.124 | 0.100 | 0.723 | 0.387 | 0.115 | 0.217 | 0.607 | 0.687 | 0.836 | 0.087 | 0.354 | 0.840 |
| 1.6E−05 | 0.959 | 0.089 | 0.094 | 0.669 | 0.164 | 0.111 | 0.146 | 0.301 | 0.344 | 0.553 | 0.088 | 0.156 | 0.466 |
| 3.2E−06 | 0.551 | 0.101 | 0.092 | 0.377 | 0.100 | 0.094 | 0.137 | 0.189 | 0.162 | 0.219 | 0.083 | 0.107 | 0.174 |
| 6.4E−07 | 0.239 | 0.089 | 0.100 | 0.164 | 0.104 | 0.108 | 0.135 | 0.167 | 0.116 | 0.098 | 0.079 | 0.081 | 0.106 |
| 1.3E−07 | 0.141 | 0.095 | 0.116 | 0.125 | 0.101 | 0.110 | 0.138 | 0.169 | 0.102 | 0.087 | 0.094 | 0.089 | 0.090 |
| 2.6E−08 | 0.131 | 0.101 | 0.097 | 0.115 | 0.099 | 0.104 | 0.141 | 0.171 | 0.103 | 0.089 | 0.087 | 0.091 | 0.092 |
| 5.1E−09 | 0.134 | 0.095 | 0.108 | 0.108 | 0.098 | 0.114 | 0.158 | 0.188 | 0.101 | 0.088 | 0.085 | 0.095 | 0.094 |
| 1E−09 | 0.151 | 0.107 | 0.119 | 0.120 | 0.104 | 0.120 | 0.165 | 0.205 | 0.133 | 0.098 | 0.090 | 0.111 | 0.112 |

TABLE 6

Cytokine release of MM6 cells stimulated with purified LPS (the same data are graphically presented in FIG. 4). MM6 cells were incubated with 10-fold serial dilution of different LPS mutants for 20 h. IL-6, IP-10, IL-1β, MCP-1 production was measured by ELISA. Data shown are depicted as the mean values in pg/mL of two independent experiments.

| LPS (ng/mL) | HB-1 | ΔL1 | ΔL2 | P | ΔL1-P | ΔL2-P | ΔL1-Lp30 | ΔL1-Lp25 | ΔLa | ΔLa-ΔL1 | ΔLa-P | ΔLa-E |
|---|---|---|---|---|---|---|---|---|---|---|---|---|
| A: IL-6 (pg/mL) | | | | | | | | | | | | |
| 5 | 2418.74 | 8.19 | 7.85 | 298.35 | 16.78 | 3.40 | 519.86 | 1490.81 | 1471.22 | 7.96 | 64.14 | 1868.77 |
| 0.5 | 1563.59 | 1.01 | 3.02 | 185.57 | 8.53 | 1.13 | 320.98 | 877.57 | 819.39 | 3.90 | 50.82 | 1054.23 |
| 0.05 | 368.77 | 0.00 | 1.51 | 7.54 | 0.28 | 2.59 | 51.98 | 185.12 | 159.19 | 2.52 | 11.49 | 287.74 |
| 0.005 | 23.15 | 0.00 | 1.88 | 0.00 | 0.00 | 0.00 | 2.35 | 15.92 | 8.49 | 3.29 | 0.39 | 18.04 |
| 0.0005 | 0.00 | 0.00 | 0.73 | 1.45 | 0.00 | 0.28 | 0.01 | 1.49 | 1.71 | 4.15 | 0.08 | 1.35 |
| B: IP-10 (pg/mL) | | | | | | | | | | | | |
| 5 | 2285.04 | 82.21 | 62.66 | 1325.52 | 322.33 | 104.11 | 1615.79 | 1933.60 | 2146.18 | 153.76 | 1247.00 | 2286.09 |
| 0.5 | 2039.96 | 32.05 | 40.90 | 1100.20 | 260.54 | 35.18 | 1594.91 | 1696.40 | 1904.13 | 49.04 | 827.49 | 2196.92 |
| 0.05 | 1378.14 | 2.32 | 12.51 | 231.93 | 30.34 | 75.39 | 784.55 | 1162.30 | 1142.07 | 12.36 | 296.77 | 1688.99 |
| 0.005 | 449.26 | 0.00 | 0.00 | 4.43 | 17.83 | 0.00 | 104.71 | 373.72 | 239.53 | 19.44 | 24.38 | 511.23 |
| 0.0005 | 55.89 | 0.00 | 0.00 | 0.00 | 0.00 | 0.00 | 20.82 | 42.53 | 34.85 | 12.55 | 17.63 | 64.73 |
| C: IL-1β (pg/mL) | | | | | | | | | | | | |
| 5 | 883.53 | 26.80 | 26.06 | 109.46 | 31.74 | 21.90 | 207.76 | 666.32 | 516.85 | 28.80 | 46.79 | 880.08 |
| 0.5 | 430.02 | 19.36 | 26.28 | 58.08 | 23.39 | 21.29 | 111.23 | 312.46 | 213.05 | 27.70 | 40.54 | 394.26 |
| 0.05 | 90.35 | 17.73 | 18.01 | 18.87 | 13.16 | 14.47 | 34.21 | 73.87 | 63.95 | 23.69 | 22.59 | 100.26 |
| 0.005 | 15.50 | 10.94 | 10.45 | 14.46 | 9.82 | 14.37 | 26.28 | 28.38 | 31.30 | 27.03 | 22.73 | 30.80 |
| 0.0005 | 13.46 | 11.31 | 11.18 | 15.06 | 6.98 | 11.68 | 17.93 | 22.72 | 20.74 | 28.69 | 23.05 | 27.98 |
| D: MCP-1 (pg/mL) | | | | | | | | | | | | |
| 5 | 5248.05 | 1587.37 | 1340.99 | 4983.60 | 2780.68 | 1416.04 | 5248.05 | 5248.05 | 5248.05 | 1442.22 | 4251.98 | 5127.77 |
| 0.5 | 5248.05 | 1309.56 | 1156.87 | 4127.69 | 1449.70 | 1085.53 | 5248.05 | 5248.05 | 5248.05 | 934.29 | 3771.32 | 5020.45 |

TABLE 6-continued

Cytokine release of MM6 cells stimulated with purified LPS (the same data are graphically presented in FIG. 4). MM6 cells were incubated with 10-fold serial dilution of different LPS mutants for 20 h. IL-6, IP-10, IL-1β, MCP-1production was measured by ELISA. Data shown are depicted as the mean values in pg/mL of two independent experiments.

| LPS (ng/mL) | HB-1 | ΔL1 | ΔL2 | P | ΔL1-P | ΔL2-P | ΔL1-Lp30 | ΔL1-Lp25 | ΔLa | ΔLa-ΔL1 | ΔLa-P | ΔLa-E |
|---|---|---|---|---|---|---|---|---|---|---|---|---|
| 0.05 | 5248.05 | 1172.01 | 1085.39 | 1370.45 | 1053.58 | 1046.54 | 4864.54 | 5158.56 | 4237.64 | 777.19 | 1470.83 | 4211.41 |
| 0.005 | 3338.36 | 1287.71 | 1166.78 | 942.49 | 1323.53 | 1357.65 | 1459.20 | 3657.48 | 2654.60 | 869.76 | 1651.58 | 2457.90 |
| 0.0005 | 1807.16 | 1201.89 | 1038.39 | 901.63 | 1122.21 | 833.56 | 1763.86 | 1466.27 | 1172.02 | 923.73 | 1191.91 | 1176.04 |

TABLE 7

Cytokine release in percentages of MM6 cells stimulated with purified LPS (the same data are graphically presented in FIG. 4) MM6 cells were stimulated with 5 ng/ml LPS. Data are expressed as mean values of two independent experiments.

|  | IL-6 (%) | SEM | IL-1b (%) | SEM | IP-10 (%) | SEM | MCP-1 (%) | SEM | IL-10 (%) | SEM |
|---|---|---|---|---|---|---|---|---|---|---|
| HB-1 | 100.00 | 4.07 | 100.00 | 6.08 | 100.00 | 7.68 | 100.0 | 0.00 | 100.00 | 19.63 |
| ΔL1 | 0.34 | 0.20 | 3.03 | 0.72 | 3.60 | 0.88 | 30.25 | 1.38 | 12.26 | 7.49 |
| ΔL2 | 0.32 | 0.20 | 2.95 | 0.69 | 2.74 | 0.35 | 25.55 | 2.30 | 11.69 | 6.77 |
| P | 12.33 | 0.75 | 12.39 | 0.40 | 58.01 | 5.08 | 94.96 | 5.04 | 41.61 | 14.45 |
| ΔL1-P | 0.69 | 0.34 | 3.59 | 0.86 | 14.11 | 1.89 | 52.99 | 16.31 | 15.41 | 8.41 |
| ΔL2-P | 0.14 | 0.08 | 2.48 | 0.96 | 4.56 | 0.60 | 26.98 | 1.83 | 11.39 | 6.58 |
| ΔL1-Lp30 | 21.49 | 2.86 | 23.51 | 5.58 | 70.71 | 11.46 | 100.00 | 0.00 | 48.97 | 8.55 |
| ΔL1-Lp25 | 61.64 | 6.63 | 75.42 | 9.59 | 84.62 | 9.85 | 100.00 | 0.00 | 79.72 | 9.28 |
| ΔLa | 60.83 | 3.58 | 58.50 | 8.23 | 93.92 | 13.41 | 100.00 | 0.00 | 79.33 | 12.54 |
| ΔLa-ΔL1 | 0.33 | 0.09 | 3.26 | 0.92 | 6.73 | 1.41 | 27.48 | 1.41 | 12.74 | 7.48 |
| ΔLa-P | 2.65 | 0.28 | 5.30 | 0.46 | 54.57 | 5.77 | 81.02 | 11.52 | 22.94 | 11.66 |
| ΔLa-E | 77.26 | 6.43 | 99.61 | 9.70 | 100.05 | 13.99 | 97.71 | 2.29 | 83.23 | 13.21 |
| No LPS | 0.12 | 0.05 | 3.62 | 1.01 | 2.41 | 0.82 | 22.94 | 3.23 | 10.69 | 6.27 |

SUPPLEMENTAL TABLE 1

Composition of the main ion peaks observed in charge-deconvoluted ESI-FT mass spectra of intact LOS from twelve mutants of *N. meningitidis* (see FIG. 1).

| Bacteria | Measured mass (u) | Proposed LOS composition Oligosaccharide | Lipid A | Calculated mass (u) | Deviation (ppm) |
|---|---|---|---|---|---|
| HB-1 | 3408.507 | PEA$_1$•Hex$_1$•Hep$_2$•HexNAc$_1$•Kdo$_2$•Gly$_1$ | P$_3$•PEA$_2$•HexN$_2$•C12$_2$•C12OH$_2$•C14OH$_2$ | 3408.514 | 2.2 |
|  | 3351.488 | PEA$_1$•Hex$_1$•Hep$_2$•HexNAc$_1$•Kdo$_2$ | P$_3$•PEA$_2$•HexN$_2$•C12$_2$•C12OH$_2$•C14OH$_2$ | 3351.493 | 1.5 |
|  | 3285.501 | PEA$_1$•Hex$_1$•Hep$_2$•HexNAc$_1$•Kdo$_2$•Gly$_1$ | P$_3$•PEA$_1$•HexN$_2$•C12$_2$•C12OH$_2$•C14OH$_2$ | 3285.506 | 1.5 |
|  | 3228.480 | PEA$_1$•Hex$_1$•Hep$_2$•HexNAc$_1$•Kdo$_2$ | P$_3$•PEA$_1$•HexN$_2$•C12$_2$•C12OH$_2$•C14OH$_2$ | 3228.484 | 1.4 |
| ΔlpxL1 | 3226.342 | PEA$_1$•Hex$_1$•Hep$_2$•HexNAc$_1$•Kdo$_2$•Gly$_1$ | P$_3$•PEA$_2$•HexN$_2$•C12$_1$•C12OH$_2$•C14OH$_2$ | 3226.347 | 1.7 |
|  | 3169.324 | PEA$_1$•Hex$_1$•Hep$_2$•HexNAc$_1$•Kdo$_2$ | P$_3$•PEA$_2$•HexN$_2$•C12$_1$•C12OH$_2$•C14OH$_2$ | 3169.326 | 0.6 |
|  | 3103.336 | PEA$_1$•Hex$_1$•Hep$_2$•HexNAc$_1$•Kdo$_2$•Gly$_1$ | P$_3$•PEA$_1$•HexN$_2$•C12$_1$•C12OH$_2$•C14OH$_2$ | 3103.339 | 0.9 |
|  | 3046.315 | PEA$_1$•Hex$_1$•Hep$_2$•HexNAc$_1$•Kdo$_2$ | P$_3$•PEA$_1$•HexN$_2$•C12$_1$•C12OH$_2$•C14OH$_2$ | 3046.317 | 0.8 |
|  | 3388.394 | PEA$_1$•Hex$_2$•Hep$_2$•HexNAc$_1$•Kdo$_2$•Gly$_1$ | P$_3$•PEA$_1$•HexN$_2$•C12$_1$•C12OH$_2$•C14OH$_2$ | 3388.400 | 1.8 |
|  | 3331.373 | PEA$_1$•Hex$_2$•Hep$_2$•HexNAc$_1$•Kdo$_2$ | P$_3$•PEA$_1$•HexN$_2$•C12$_1$•C12OH$_2$•C14OH$_2$ | 3331.379 | 1.7 |
| ΔlpxL2 | 3023.367 | PEA$_1$•Hex$_1$•Hep$_2$•HexNAc$_1$•Kdo$_2$•Gly$_1$ | P$_2$•PEA$_1$•HexN$_2$•C12$_1$•C12OH$_2$•C14OH$_2$ | 3023.373 | 1.8 |
|  | 2966.348 | PEA$_1$•Hex$_1$•Hep$_2$•HexNAc$_1$•Kdo$_2$ | P$_2$•PEA$_1$•HexN$_2$•C12$_1$•C12OH$_2$•C14OH$_2$ | 2966.351 | 1.0 |
|  | 3185.419 | PEA$_1$•Hex$_2$•Hep$_2$•HexNAc$_1$•Kdo$_2$•Gly$_1$ | P$_2$•PEA$_1$•HexN$_2$•C12$_1$•C12OH$_2$•C14OH$_2$ | 3185.425 | 2.0 |
|  | 3128.398 | PEA$_1$•Hex$_2$•Hep$_2$•HexNAc$_1$•Kdo$_2$ | P$_2$•PEA$_1$•HexN$_2$•C12$_1$•C12OH$_2$•C14OH$_2$ | 3128.404 | 1.9 |
|  | 2843.340 | PEA$_1$•Hex$_1$•Hep$_2$•HexNAc$_1$•Kdo$_2$ | P$_2$•HexN$_2$•C12$_1$•C12OH$_2$•C14OH$_2$ | 2843.343 | 0.9 |
|  | 2720.331 | Hex$_1$•Hep$_2$•HexNAc$_1$•Kdo2 | P$_2$•HexN$_2$•C12$_1$•C12OH$_2$•C14OH$_2$ | 2720.334 | 1.1 |
| pagL | 3210.345 | PEA$_1$•Hex$_1$•Hep$_2$•HexNAc$_1$•Kdo$_2$•Gly$_1$ | P$_3$•PEA$_2$•HexN$_2$•C12$_2$•C12OH$_1$C14OH$_2$ | 3210.352 | 2.3 |
|  | 3232.326* | PEA$_1$•Hex$_1$•Hep$_2$•HexNAc$_1$•Kdo$_2$•Gly$_1$ | P$_3$•PEA$_2$•HexN$_2$•C12$_2$•C12OH$_1$C14OH$_2$ | 3232.335 | 2.8 |
|  | 3153.325 | PEA$_1$•Hex$_1$•Hep$_2$•HexNAc$_1$•Kdo$_2$ | P$_3$•PEA$_2$•HexN$_2$•C12$_2$•C12OH$_1$C14OH$_2$ | 3153.331 | 1.9 |
|  | 3175.306* | PEA$_1$•Hex$_1$•Hep$_2$•HexNAc$_1$•Kdo$_2$ | P$_3$•PEA$_2$•HexN$_2$•C12$_2$•C12OH$_1$C14OH$_2$ | 3175.313 | 2.4 |
|  | 3087.338 | PEA$_1$•Hex$_1$•Hep$_2$•HexNAc$_1$•Kdo$_2$•Gly$_1$ | P$_3$•PEA$_1$•HexN$_2$•C12$_2$•C12OH$_1$C14OH$_2$ | 3087.344 | 1.9 |
|  | 3109.320* | PEA$_1$•Hex$_1$•Hep$_2$•HexNAc$_1$•Kdo$_2$•Gly$_1$ | P$_3$•PEA$_1$•HexN$_2$•C12$_2$•C12OH$_1$C14OH$_2$ | 3109.326 | 2.1 |
|  | 3030.318 | PEA$_1$•Hex$_1$•Hep$_2$•HexNAc$_1$•Kdo$_2$ | P$_3$•PEA$_1$•HexN$_2$•C12$_2$•C12OH$_1$C14OH$_2$ | 3030.322 | 1.5 |
|  | 3052.298* | PEA$_1$•Hex$_1$•Hep$_2$•HexNAc$_1$•Kdo$_2$ | P$_3$•PEA$_1$•HexN$_2$•C12$_2$•C12OH$_1$C14OH$_2$ | 3052.305 | 2.3 |
|  | 2971.161 | PEA$_1$•Hex$_1$•Hep$_2$•HexNAc$_1$•Kdo$_2$ | P$_3$•PEA$_1$•HexN$_2$•C12$_2$•C12OH$_1$•C14OH$_2$ | 2971.164 | 1.0 |
|  | 2950.352 | PEA$_1$•Hex$_1$•Hep$_2$•HexNAc$_1$•Kdo$_2$ | P$_2$•PEA$_1$•HexN$_2$•C12$_2$•C12OH$_1$•C14OH$_2$ | 2950.356 | 1.4 |
|  | 2848.152 | PEA$_1$•Hex$_1$•Hep$_2$•HexNAc$_1$•Kdo$_2$ | P$_3$•PEA$_2$•HexN$_2$•C12$_2$•C12OH$_1$C14OH$_2$ | 2848.155 | 1.2 |
|  | 3408.505 | PEA$_1$•Hex$_1$•Hep$_2$•HexNAc$_1$•Kdo$_2$•Gly$_1$ | P$_3$•PEA$_2$•HexN$_2$•C12$_2$•C12OH$_2$•C14OH$_2$ | 3408.514 | 2.8 |
|  | 3351.485 | PEA$_1$•Hex$_1$•Hep$_2$•HexNAc$_1$•Kdo$_2$ | P$_3$•PEA$_2$•HexN$_2$•C12$_2$•C12OH$_2$•C14OH$_2$ | 3351.493 | 2.4 |
|  | 3372.396 | PEA$_1$•Hex$_2$•Hep$_2$•HexNAc$_1$•Kdo$_2$•Gly$_1$ | P$_3$•PEA$_2$•HexN$_2$•C12$_2$•C12OH$_1$C14OH$_2$ | 3372.405 | 2.8 |
|  | 3315.376 | PEA$_1$•Hex$_2$•Hep$_2$•HexNAc$_1$•Kdo$_2$ | P$_3$•PEA$_2$•HexN$_2$•C12$_2$•C12OH$_1$C14OH$_2$ | 3315.384 | 2.4 |

SUPPLEMENTAL TABLE 1-continued

Composition of the main ion peaks observed in charge-deconvoluted ESI-FT mass spectra of intact LOS from twelve mutants of N. meningitidis (see FIG. 1).

| Bacteria | Measured mass (u) | Oligosaccharide | Lipid A | Calculated mass (u) | Deviation (ppm) |
|---|---|---|---|---|---|
| ΔlpxL1-pagL | 3028.180 | $PEA_1•Hex_1•Hep_2•HexNAc_1•Kdo_2•Gly_1$ | $P_3•PEA_2•HexN_2•C12_1•C12OH_1•C14OH_2$ | 3028.185 | 1.8 |
| | 2971.160 | $PEA_1•Hex_1•Hep_2•HexNAc_1•Kdo_2$ | $P_3•PEA_2•HexN_2•C12_1•C12OH_1•C14OH_2$ | 2971.164 | 1.3 |
| | 2905.173 | $PEA_1•Hex_1•Hep_2•HexNAc_1•Kdo_2•Gly_1$ | $P_3•PEA_1•HexN_2•C12_1•C12OH_1•C14OH_2$ | 2905.177 | 1.3 |
| | 2848.152 | $PEA_1•Hex_1•Hep_2•HexNAc_1•Kdo_2$ | $P_3•PEA_1•HexN_2•C12_1•C12OH_1•C14OH_2$ | 2848.155 | 1.2 |
| | 3226.339 | $PEA_1•Hex_1•Hep_2•HexNAc_1•Kdo_2•Gly_1$ | $P_3•PEA_2•HexN_2•C12_1•C12OH_2•C14OH_2$ | 3226.347 | 2.6 |
| | 3169.319 | $PEA_1•Hex_1•Hep_2•HexNAc_1•Kdo_2$ | $P_3•PEA_2•HexN_2•C12_1•C12OH_2•C14OH_2$ | 3169.326 | 2.2 |
| | 3190.232 | $PEA_1•Hex_2•Hep_2•HexNAc_1•Kdo_2•Gly_1$ | $P_3•PEA_2•HexN_2•C12_1•C12OH_1•C14OH_2$ | 3190.238 | 2.0 |
| | 3133.210 | $PEA_1•Hex_2•Hep_2•HexNAc_1•Kdo_2$ | $P_3•PEA_2•HexN_2•C12_1•C12OH_1•C14OH_2$ | 3133.217 | 2.2 |
| | 3103.331 | $PEA_1•Hex_1•Hep_2•HexNAc_1•Kdo_2•Gly_1$ | $P_3•PEA_1•HexN_2•C12_1•C12OH_2•C14OH_2$ | 3103.339 | 2.5 |
| ΔlpxL2-pagL | 2825.206 | $PEA_1•Hex_1•Hep_2•HexNAc_1•Kdo_2•Gly_1$ | $P_2•PEA_1•HexN_2•C12_1•C12OH_1•C14OH_2$ | 2825.211 | 1.6 |
| | 2768.187 | $PEA_1•Hex_1•Hep_2•HexNAc_1•Kdo_2$ | $P_2•PEA_1•HexN_2•C12_1•C12OH_1•C14OH_2$ | 2768.189 | 0.8 |
| | 2987.257 | $PEA_1•Hex_2•Hep_2•HexNAc_1•Kdo_2•Gly_1$ | $P_2•PEA_1•HexN_2•C12_1•C12OH_1•C14OH_2$ | 2987.263 | 2.1 |
| | 2930.236 | $PEA_1•Hex_2•Hep_2•HexNAc_1•Kdo_2$ | $P_2•PEA_1•HexN_2•C12_1•C12OH_1•C14OH_2$ | 2930.242 | 2.0 |
| | 2966.344 | $PEA_1•Hex_1•Hep_2•HexNAc_1•Kdo_2$ | $P_2•PEA_1•HexN_2•C12_1•C12OH_2•C14OH_2$ | 2966.351 | 2.4 |
| | 2548.127 | $PEA_1•Hex_1•Hep_2•HexNAc_1•Kdo_1$ | $P_2•PEA_1•HexN_2•C12_1•C12OH_1•C14OH_2$ | 2548.131 | 1.5 |
| | 2645.178 | $PEA_1•Hex_1•Hep_2•HexNAc_1•Kdo_2$ | $P_2•HexN_2•C12_1•C12OH_1•C14OH_2$ | 2645.181 | 1.0 |
| | 2720.331 | $Hex_1•Hep_2•HexNAc_1•Kdo_2$ | $P_2•HexN_2•C12_1•C12OH_2•C14OH_2$ | 2720.334 | 1.1 |
| ΔlpxL1-lpxP 30° C. | 3046.315 | $PEA_1•Hex_1•Hep_2•HexNAc_1•Kdo_2$ | $P_3•PEA_1•HexN_2•C12_1•C12OH_2•C14OH_2$ | 3046.317 | 0.8 |
| | 3103.333 | $PEA_1•Hex_1•Hep_2•HexNAc_1•Kdo_2Gly_1$ | $P_3•PEA_1•HexN_2•C12_1•C12OH_2•C14OH_2$ | 3103.339 | 1.9 |
| | 3169.322 | $PEA_1•Hex_1•Hep_2•HexNAc_1•Kdo_2$ | $P_3•PEA_2•HexN_2•C12_1•C12OH_2•C14OH_2$ | 3169.326 | 1.2 |
| | 3226.340 | $PEA_1•Hex_1•Hep_2•HexNAc_1•Kdo_2Gly_1$ | $P_3•PEA_2•HexN_2•C12_1•C12OH_2•C14OH_2$ | 3226.347 | 2.3 |
| | 3208.364 | $PEA_1•Hex_2•Hep_2•HexNAc_1•Kdo_2$ | $P_3•PEA_1•HexN_2•C12_1•C12OH_2•C14OH_2$ | 3208.370 | 1.9 |
| | 3265.382 | $PEA_1•Hex_2•Hep_2•HexNAc_1•Kdo_2Gly_1$ | $P_3•PEA_1•HexN_2•C12_1•C12OH_2•C14OH_2$ | 3265.392 | 3.0 |
| | 3331.372 | $PEA_1•Hex_2•Hep_2•HexNAc_1•Kdo_2$ | $P_3•PEA_2•HexN_2•C12_1•C12OH_2•C14OH_2$ | 3331.379 | 2.0 |
| | 3388.391 | $PEA_1•Hex_2•Hep_2•HexNAc_1•Kdo_2Gly_1$ | $P_3•PEA_2•HexN_2•C12_1•C12OH_2•C14OH_2$ | 3388.400 | 2.7 |
| | 3282.524 | $PEA_1•Hex_1•Hep_2•HexNAc_1•Kdo_2$ | $P_3•PEA_1•HexN_2•C12_1•C12OH_2•C14OH_2•C16:1_1$ | 3282.531 | 2.3 |
| | 3339.543 | $PEA_1•Hex_1•Hep_2•HexNAc_1•Kdo_2Gly_1$ | $P_3•PEA_1•HexN_2•C12_1•C12OH_2•C14OH_2•C16:1_1$ | 3339.553 | 3.0 |
| | 3405.533 | $PEA_1•Hex_1•Hep_2•HexNAc_1•Kdo_2$ | $P_3•PEA_2•HexN_2•C12_1•C12OH_2•C14OH_2•C16:1_1$ | 3405.540 | 2.0 |
| | 3462.553 | $PEA_1•Hex_1•Hep_2•HexNAc_1•Kdo_2Gly_1$ | $P_3•PEA_2•HexN_2•C12_1•C12OH_2•C14OH_2•C16:1_1$ | 3462.561 | 2.4 |
| | 3444.574 | $PEA_1•Hex_2•Hep_2•HexNAc_1•Kdo_2$ | $P_3•PEA_1•HexN_2•C12_1•C12OH_2•C14OH_2•C16:1_1$ | 3444.584 | 3.0 |
| | 3567.585 | $PEA_1•Hex_2•Hep_2•HexNAc_1•Kdo_2$ | $P_3•PEA_2•HexN_2•C12_1•C12OH_2•C14OH_2•C16:1_1$ | 3567.593 | 2.2 |
| | 3624.606 | $PEA_1•Hex_2•Hep_2•HexNAc_1•Kdo_2•Gly_1$ | $P_3•PEA_2•HexN_2•C12_1•C12OH_2•C14OH_2•C16:1_1$ | 3624.614 | 2.3 |
| ΔlpxL1-lpxP 25° C. | 3046.314 | $PEA_1•Hex_1•Hep_2•HexNAc_1•Kdo_2$ | $P_3•PEA_1•HexN_2•C12_1•C12OH_2•C14OH_2$ | 3046.317 | 1.1 |
| | 3103.333 | $PEA_1•Hex_1•Hep_2•HexNAc_1•Kdo_2Gly_1$ | $P_3•PEA_1•HexN_2•C12_1•C12OH_2•C14OH_2$ | 3103.339 | 1.9 |
| | 3169.321 | $PEA_1•Hex_1•Hep_2•HexNAc_1•Kdo_2$ | $P_3•PEA_2•HexN_2•C12_1•C12OH_2•C14OH_2$ | 3169.326 | 1.6 |
| | 3226.341 | $PEA_1•Hex_1•Hep_2•HexNAc_1•Kdo_2•Gly_1$ | $P_3•PEA_2•HexN_2•C12_1•C12OH_2•C14OH_2$ | 3226.347 | 2.0 |
| | 3208.366 | $PEA_1•Hex_2•Hep_2•HexNAc_1•Kdo_2$ | $P_3•PEA_1•HexN_2•C12_1•C12OH_2•C14OH_2$ | 3208.370 | 1.3 |
| | 3265.386 | $PEA_1•Hex_2•Hep_2•HexNAc_1•Kdo_2•Gly_1$ | $P_3•PEA_1•HexN_2•C12_1•C12OH_2•C14OH_2$ | 3265.392 | 1.7 |
| | 3331.373 | $PEA_1•Hex_2•Hep_2•HexNAc_1•Kdo_2$ | $P_3•PEA_2•HexN_2•C12_1•C12OH_2•C14OH_2$ | 3331.379 | 1.7 |
| | 3388.393 | $PEA_1•Hex_2•Hep_2•HexNAc_1•Kdo_2•Gly_1$ | $P_3•PEA_2•HexN_2•C12_1•C12OH_2•C14OH_2$ | 3388.400 | 2.1 |
| | 3254.494 | $PEA_1•Hex_1•Hep_2•HexNAc_1•Kdo_2$ | $P_3•PEA_1•HexN_2•C12_1•C12OH_2•C14OH_2•C16:1_1$—C2H4 | 3254.500 | 1.9 |
| | 3282.526 | $PEA_1•Hex_1•Hep_2•HexNAc_1•Kdo_2$ | $P_3•PEA_1•HexN_2•C12_1•C12OH_2•C14OH_2•C16:1_1$ | 3282.531 | 1.6 |
| | 3311.516 | $PEA_1•Hex_1•Hep_2•HexNAc_1•Kdo_2Gly_1$ | $P_3•PEA_1•HexN_2•C12_1•C12OH_2•C14OH_2•C16:1_1$—C2H4 | 3311.522 | 1.7 |
| | 3339.546 | $PEA_1•Hex_1•Hep_2•HexNAc_1•Kdo_2•Gly_1$ | $P_3•PEA_1•HexN_2•C12_1•C12OH_2•C14OH_2•C16:1_1$ | 3339.553 | 2.1 |
| | 3377.502 | $PEA_1•Hex_1•Hep_2•HexNAc_1•Kdo_2$ | $P_3•PEA_2•HexN_2•C12_1•C12OH_2•C14OH_2•C16:1_1$—C2H4 | 3377.509 | 2.0 |
| | 3405.535 | $PEA_1•Hex_1•Hep_2•HexNAc_1•Kdo_2$ | $P_3•PEA_2•HexN_2•C12_1•C12OH_2•C14OH_2•C16:1_1$ | 3405.540 | 1.4 |
| | 3434.522 | $PEA_1•Hex_1•Hep_2•HexNAc_1•Kdo_2•Gly_1$ | $P_3•PEA_2•HexN_2•C12_1•C12OH_2•C14OH_2•C16:1_1$—C2H4 | 3434.530 | 2.4 |
| | 3462.554 | $PEA_1•Hex_1•Hep_2•HexNAc_1•Kdo_2•Gly_1$ | $P_3•PEA_2•HexN_2•C12_1•C12OH_2•C14OH_2•C16:1_1$ | 3462.561 | 2.1 |
| | 3444.575 | $PEA_1•Hex_2•Hep_2•HexNAc_1•Kdo_2$ | $P_3•PEA_1•HexN_2•C12_1•C12OH_2•C14OH_2•C16:1_1$ | 3444.584 | 2.7 |
| | 3501.596 | $PEA_1•Hex_2•Hep_2•HexNAc_1•Kdo_2•Gly_1$ | $P_3•PEA_1•HexN_2•C12_1•C12OH_2•C14OH_2•C16:1_1$ | 3501.606 | 2.8 |
| | 3567.586 | $PEA_1•Hex_2•Hep_2•HexNAc_1•Kdo_2$ | $P_3•PEA_2•HexN_2•C12_1•C12OH_2•C14OH_2•C16:1_1$ | 3567.593 | 1.9 |
| | 3624.608 | $PEA_1•Hex_2•Hep_2•HexNAc_1•Kdo_2•Gly_1$ | $P_3•PEA_2•HexN_2•C12_1•C12OH_2•C14OH_2•C16:1_1$ | 3624.614 | 1.7 |
| ΔlptA | 3162.489 | $PEA_1•Hex_1•Hep_2•HexNAc_1•Kdo_2•Gly_1$ | $P_3•HexN_2•C12_2•C12OH_2•C14OH_2$ | 3162.497 | 2.7 |
| | 3184.471* | $PEA_1•Hex_1•Hep_2•HexNAc_1•Kdo_2•Gly_1$ | $P_3•HexN_2•C12_2•C12OH_2•C14OH_2$ | 3184.480 | 2.8 |
| | 3105.471 | $PEA_1•Hex_1•Hep_2•HexNAc_1•Kdo_2$ | $P_3•HexN_2•C12_2•C12OH_2•C14OH_2$ | 3105.476 | 1.6 |
| | 3127.452* | $PEA_1•Hex_1•Hep_2•HexNAc_1•Kdo_2$ | $P_3•HexN_2•C12_2•C12OH_2•C14OH_2$ | 3127.458 | 2.0 |
| | 3025.506 | $PEA_1•Hex_1•Hep_2•HexNAc_1•Kdo_2$ | $P_2•HexN_2•C12_2•C12OH_2•C14OH_2$ | 3025.510 | 1.2 |
| | 3324.541 | $PEA_1•Hex_2•Hep_2•HexNAc_1•Kdo_2•Gly$ | $P_3•HexN_2•C12_2•C12OH_2•C14OH_2$ | 3324.550 | 2.8 |
| | 3267.521 | $PEA_1•Hex_2•Hep_2•HexNAc_1•Kdo_2$ | $P_3•HexN_2•C12_2•C12OH_2•C14OH_2$ | 3267.529 | 2.4 |
| ΔlptA-ΔlpxL1 | 2980.324 | $PEA_1•Hex_1•Hep_2•HexNAc_1•Kdo_2•Gly_1$ | $P_3•HexN_2•C12_1•C12OH_2•C14OH_2$ | 2980.330 | 2.1 |
| | 2923.307 | $PEA_1•Hex_1•Hep_2•HexNAc_1•Kdo_2$ | $P_3•HexN_2•C12_1•C12OH_2•C14OH_2$ | 2923.309 | 0.6 |
| | 3142.375 | $PEA_1•Hex_2•Hep_2•HexNAc_1•Kdo_2•Gly_1$ | $P_3•HexN_2•C12_1•C12OH_2•C14OH_2$ | 3142.383 | 2.6 |
| | 3085.354 | $PEA_1•Hex_2•Hep_2•HexNAc_1•Kdo_2$ | $P_3•HexN_2•C12_1•C12OH_2•C14OH_2$ | 3085.362 | 2.5 |
| ΔlptA-pagL | 2964.328 | $PEA_1•Hex_1•Hep_2•HexNAc_1•Kdo_2•Gly_1$ | $P_3•HexN_2•C12_2•C12OH_1•C14OH_2$ | 2964.335 | 2.5 |
| | 2986.309* | $PEA_1•Hex_1•Hep_2•HexNAc_1•Kdo_2•Gly_1$ | $P_3•HexN_2•C12_2•C12OH_1•C14OH_2$ | 2986.318 | 3.0 |
| | 2907.311 | $PEA_1•Hex_1•Hep_2•HexNAc_1•Kdo_2$ | $P_3•HexN_2•C12_2•C12OH_1•C14OH_2$ | 2907.314 | 1.0 |
| | 2929.290* | $PEA_1•Hex_1•Hep_2•HexNAc_1•Kdo_2$ | $P_3•HexN_2•C12_2•C12OH_1•C14OH_2$ | 2929.296 | 2.2 |
| | 3069.359 | $PEA_1•Hex_2•Hep_2•HexNAc_1•Kdo_2$ | $P_3•HexN_2•C12_2•C12OH_2•C14OH_2$ | 3069.367 | 2.5 |
| | 3105.468 | $PEA_1•Hex_1•Hep_2•HexNAc_1•Kdo_2$ | $P_3•HexN_2•C12_2•C12OH_2•C14OH_2$ | 3105.476 | 2.6 |
| | 3126.379 | $PEA_1•Hex_2•Hep_2•HexNAc_1•Kdo_2•Gly_1$ | $P_3•HexN_2•C12_2•C12OH_2•C14OH_2$ | 3126.388 | 3.0 |
| | 3162.488 | $PEA_1•Hex_1•Hep_2•HexNAc_1•Kdo_2•Gly_1$ | $P_3•HexN_2•C12_2•C12OH_2•C14OH_2$ | 3162.497 | 3.0 |
| | 2725.144 | $PEA_1•Hex_1•Hep_2•HexNAc_1•Kdo_2$ | $P_3•HexN_2•C12_1•C12OH_1•C14OH_2$ | 2725.147 | 1.1 |
| | 2782.165 | $PEA_1•Hex_1•Hep_2•HexNAc_1•Kdo_2•Gly_1$ | $P_3•HexN_2•C12_1•C12OH_1•C14OH_2$ | 2782.168 | 1.2 |

SUPPLEMENTAL TABLE 1-continued

Composition of the main ion peaks observed in charge-deconvoluted ESI-FT mass spectra of intact LOS from twelve mutants of *N. meningitidis* (see FIG. 1).

| Bacteria | Measured mass (u) | Proposed LOS composition Oligosaccharide | Lipid A | Calculated mass (u) | Deviation (ppm) |
|---|---|---|---|---|---|
| | 2827.344 | $PEA_1 \cdot Hex_1 \cdot Hep_2 \cdot HexNAc_1 \cdot Kdo_2$ | $P_2 \cdot HexN_2 \cdot C12_2 \cdot C12OH_1 \cdot C14OH_2$ | 2827.348 | 1.3 |
| | 2687.254 | $PEA_1 \cdot Hex_1 \cdot Hep_2 \cdot HexNAc_1 \cdot Kdo_1$ | $P_3 \cdot HexN_2 \cdot C12_2 \cdot C12OH_1 \cdot C14OH_2$ | 2687.256 | 0.6 |
| ΔlptA-lpxE | 3082.525 | $PEA_1 \cdot Hex_1 \cdot Hep_2 \cdot HexNAc_1 \cdot Kdo_2 \cdot Gly_1$ | $P_2 \cdot HexN_2 \cdot C12_2 \cdot C12OH_2 \cdot C14OH_2$ | 3082.531 | 2.0 |
| | 3104.507* | $PEA_1 \cdot Hex_1 \cdot Hep_2 \cdot HexNAc_1 \cdot Kdo_2 \cdot Gly_1$ | $P_2 \cdot HexN_2 \cdot C12_2 \cdot C12OH_2 \cdot C14OH_2$ | 3104.514 | 2.1 |
| | 3025.508 | $PEA_1 \cdot Hex_1 \cdot Hep_2 \cdot HexNAc_1 \cdot Kdo_2$ | $P_2 \cdot HexN_2 \cdot C12_2 \cdot C12OH_2 \cdot C14OH_2$ | 3025.510 | 0.5 |
| | 3047.488* | $PEA_1 \cdot Hex_1 \cdot Hep_2 \cdot HexNAc_1 \cdot Kdo_2$ | $P_2 \cdot HexN_2 \cdot C12_2 \cdot C12OH_2 \cdot C14OH_2$ | 3047.492 | 1.3 |
| | 3069.468** | $PEA_1 \cdot Hex_1 \cdot Hep_2 \cdot HexNAc_1 \cdot Kdo_2$ | $P_2 \cdot HexN_2 \cdot C12_2 \cdot C12OH_2 \cdot C14OH_2$ | 3069.475 | 2.1 |
| | 3244.576 | $PEA_1 \cdot Hex_2 \cdot Hep_2 \cdot HexNAc_1 \cdot Kdo_2 \cdot Gly_1$ | $P_2 \cdot HexN_2 \cdot C12_2 \cdot C12OH_2 \cdot C14OH_2$ | 3244.584 | 2.4 |
| | 3187.556 | $PEA_1 \cdot Hex_2 \cdot Hep_2 \cdot HexNAc_1 \cdot Kdo_2$ | $P_2 \cdot HexN_2 \cdot C12_2 \cdot C12OH_2 \cdot C14OH_2$ | 3187.562 | 2.0 |
| | 2805.449 | $PEA_1 \cdot Hex_1 \cdot Hep_2 \cdot HexNAc_1 \cdot Kdo_1$ | $P_2 \cdot HexN_2 \cdot C12_2 \cdot C12OH_2 \cdot C14OH_2$ | 2805.451 | 0.8 |

*Monosodium adduct.
**Disodium adduct.
Abbreviations:
Kdo, 3-deoxy-D-manno-oct-2-ulosonic acid;
Hep, L-glycero-D-manno-heptose;
Hex, hexose;
HexNAc, N-acetylhexosamine;
Gly, glycine;
PEA, phosphoethanolamine;
P, phosphate;
C12OH, 3-hydroxy-dodecanoic acid;
C14OH, 3-hydroxy-tetradecanoic acid;
C12, dodecanoic acid;
C16:1, 9-hexadecenoic acid

SUPPLEMENTAL TABLE 2

Proposed compositions for charge-deconvoluted fragment ion peaks obtained by in-source collision-induced dissociation ESI-FT MS of LOS.

| Bacteria | Fragment ion type[a] | Measured mass (u) | Proposed LOS composition Oligosaccharide | Lipid A | Calculated mass (u) | Deviation (ppm) |
|---|---|---|---|---|---|---|
| HB-1 | B | 1369.404 | $PE_1 \cdot Hex_1 \cdot Hep_2 \cdot HexNAc_1 \cdot Kdo_2 \cdot Gly_1$ | | 1369.406 | 1.1 |
| | B-Kdo-CO2 | 1105.355 | $PE_1 \cdot Hex_1 \cdot Hep_2 \cdot HexNAc_1 \cdot Kdo_2 \cdot Gly_1$ | | 1105.357 | 2.2 |
| | B-Kdo-CO2 | 1048.334 | $PE_1 \cdot Hex_1 \cdot Hep_2 \cdot HexNAc_1 \cdot Kdo_2$ | | 1048.336 | 1.9 |
| | Y | 1916.098 | | $P_3 \cdot PE_1 \cdot HexN_2 \cdot C12_2 \cdot C12OH_2 \cdot C14OH_2$ | 1916.100 | 1.2 |
| | Y | 2039.106 | | $P_3 \cdot PE_2 \cdot HexN_2 \cdot C12_2 \cdot C12OH_2 \cdot C14OH_2$ | 2039.109 | 1.4 |
| ΔlpxL1 | B | 1369.405 | $PE_1 \cdot Hex_1 \cdot Hep_2 \cdot HexNAc_1 \cdot Kdo_2 \cdot Gly_1$ | | 1369.406 | 0.4 |
| | B-Kdo-CO2 | 1105.356 | $PE_1 \cdot Hex_1 \cdot Hep_2 \cdot HexNAc_1 \cdot Kdo_2 \cdot Gly_1$ | | 1105.357 | 1.3 |
| | B-Kdo-CO2 | 1048.335 | $PE_1 \cdot Hex_1 \cdot Hep_2 \cdot HexNAc_1 \cdot Kdo_2$ | | 1048.336 | 0.9 |
| | Y | 1733.933 | | $P_3 \cdot PE_1 \cdot HexN_2 \cdot C12_1 \cdot C12OH_2 \cdot C14OH_2$ | 1733.933 | 0.2 |
| | Y | 1856.942 | | $P_3 \cdot PE_2 \cdot HexN_2 \cdot C12_1 \cdot C12OH_2 \cdot C14OH_2$ | 1856.942 | 0.1 |
| ΔlpxL2 | B | 1369.404 | $PE_1 \cdot Hex_1 \cdot Hep_2 \cdot HexNAc_1 \cdot Kdo_2 \cdot Gly_1$ | | 1369.406 | 1.1 |
| | B-Kdo-CO2 | 1105.356 | $PE_1 \cdot Hex_1 \cdot Hep_2 \cdot HexNAc_1 \cdot Kdo_2 \cdot Gly_1$ | | 1105.357 | 1.3 |
| | B-Kdo-CO2 | 1048.335 | $PE_1 \cdot Hex_1 \cdot Hep_2 \cdot HexNAc_1 \cdot Kdo_2$ | | 1048.336 | 0.9 |
| | B-Kdo-CO2 | 1267.409 | $PE_1 \cdot Hex_2 \cdot Hep_2 \cdot HexNAc_1 \cdot Kdo_2 \cdot Gly_1$ | | 1267.410 | 1.0 |
| | B-Kdo-CO2 | 1210.387 | $PE_1 \cdot Hex_2 \cdot Hep_2 \cdot HexNAc_1 \cdot Kdo_2$ | | 1210.389 | 1.5 |
| | Y | 1530.957 | | $P_2 \cdot HexN_2 \cdot C12_1 \cdot C12OH_2 \cdot C14OH_2$ | 1530.958 | 0.9 |
| | Y | 1653.965 | | $P_2 \cdot PE_1 \cdot HexN_2 \cdot C12_1 \cdot C12OH_2 \cdot C14OH_2$ | 1653.967 | 1.2 |
| pagL | B | 1369.404 | $PE_1 \cdot Hex_1 \cdot Hep_2 \cdot HexNAc_1 \cdot Kdo_2 \cdot Gly_1$ | | 1369.406 | 1.1 |
| | B | 1312.381 | $PE_1 \cdot Hex_1 \cdot Hep_2 \cdot HexNAc_1 \cdot Kdo_2$ | | 1312.384 | 2.4 |
| | B-Kdo-CO2 | 1105.356 | $PE_1 \cdot Hex_1 \cdot Hep_2 \cdot HexNAc_1 \cdot Kdo_2 \cdot Gly_1$ | | 1105.357 | 1.3 |
| | B-Kdo-CO2 | 1048.335 | $PE_1 \cdot Hex_1 \cdot Hep_2 \cdot HexNAc_1 \cdot Kdo_2$ | | 1048.336 | 0.9 |
| | B-Kdo-CO2 | 1210.387 | $PE_1 \cdot Hex_2 \cdot Hep_2 \cdot HexNAc_1 \cdot Kdo_2$ | | 1210.389 | 1.5 |
| | Y | 1717.937 | | $P_3 \cdot PE_1 \cdot HexN_2 \cdot C12_2 \cdot C12OH_1 \cdot C14OH_2$ | 1717.938 | 0.8 |
| | Y | 1840.946 | | $P_3 \cdot PE_2 \cdot HexN_2 \cdot C12_2 \cdot C12OH_1 \cdot C14OH_2$ | 1840.947 | 0.5 |
| ΔlpxL1-pagL | B | 1369.404 | $PE_1 \cdot Hex_1 \cdot Hep_2 \cdot HexNAc_1 \cdot Kdo_2 \cdot Gly_1$ | | 1369.406 | 1.1 |
| | B-Kdo-CO2 | 1105.356 | $PE_1 \cdot Hex_1 \cdot Hep_2 \cdot HexNAc_1 \cdot Kdo_2 \cdot Gly_1$ | | 1105.357 | 1.3 |
| | B-Kdo-CO2 | 1048.335 | $PE_1 \cdot Hex_1 \cdot Hep_2 \cdot HexNAc_1 \cdot Kdo_2$ | | 1048.336 | 0.9 |
| | B-Kdo-$CO_2$ | 1267.409 | $PE_1 \cdot Hex_2 \cdot Hep_2 \cdot HexNAc_1 \cdot Kdo_2 \cdot Gly_1$ | | 1267.410 | 1.0 |
| | B-Kdo-$CO_2$ | 1210.387 | $PE_1 \cdot Hex_2 \cdot Hep_2 \cdot HexNAc_1 \cdot Kdo_2$ | | 1210.389 | 1.5 |
| | Y | 1535.77 | | $P_3 \cdot PE_1 \cdot HexN_2 \cdot C12_1 \cdot C12OH_2 \cdot C14OH_2$ | 1535.771 | 0.8 |
| | Y | 1658.779 | | $P_3 \cdot PE_2 \cdot HexN_2 \cdot C12_1 \cdot C12OH_2 \cdot C14OH_2$ | 1658.780 | 0.5 |
| | Y | 1856.943 | | $P_3 \cdot PE_2 \cdot HexN_2 \cdot C12_1 \cdot C12OH_2 \cdot C14OH_2$ | 1856.942 | 0.6 |
| | Y | 1733.933 | | $P_3 \cdot PE_1 \cdot HexN_2 \cdot C12_1 \cdot C12OH_2 \cdot C14OH_2$ | 1733.933 | 0.2 |

SUPPLEMENTAL TABLE 2-continued

Proposed compositions for charge-deconvoluted fragment ion peaks obtained by in-source collision-induced dissociation ESI-FT MS of LOS.

| Bacteria | Fragment ion type[a] | Measured mass (u) | Proposed LOS composition Oligosaccharide | Lipid A | Calculated mass (u) | Deviation (ppm) |
|---|---|---|---|---|---|---|
| ΔlpxL2-pagL | B-Kdo-CO2 | 1105.355 | $PE_1 \cdot Hex_1 \cdot Hep_2 \cdot HexNAc_1 \cdot Kdo_2 \cdot Gly_1$ | | 1105.357 | 2.2 |
| | B-Kdo-CO2 | 1048.334 | $PE_1 \cdot Hex_1 \cdot Hep_2 \cdot HexNAc_1 \cdot Kdo_2$ | | 1048.336 | 1.9 |
| | B-Kdo-CO2 | 1267.408 | $PE_1 \cdot Hex_2 \cdot Hep_2 \cdot HexNAc_1 \cdot Kdo_2 \cdot Gly_1$ | | 1267.410 | 1.8 |
| | B-Kdo-CO2 | 1210.387 | $PE_1 \cdot Hex_2 \cdot Hep_2 \cdot HexNAc_1 \cdot Kdo_2$ | | 1210.389 | 1.5 |
| | Y | 1455.802 | | $P_2 \cdot PE_1 \cdot HexN_2 \cdot C12_1 \cdot C12OH_1 \cdot C14OH_2$ | 1455.805 | 2.0 |
| | Y | 1653.964 | | $P_2 \cdot PE_1 \cdot HexN_2 \cdot C12_1 \cdot C12OH_2 \cdot C14OH_2$ | 1653.967 | 1.8 |
| | Y | 1530.955 | | $P_2 \cdot HexN_2 \cdot C12_1 \cdot C12OH_2 \cdot C14OH_2$ | 1530.958 | 2.2 |
| ΔlpxL1-LpxP 30° C. | B | 1369.403 | $PE_1 \cdot Hex_1 \cdot Hep_2 \cdot HexNAc_1 \cdot Kdo_2 \cdot Gly_1$ | | 1369.406 | 1.9 |
| | B-Kdo-CO2 | 1105.356 | $PE_1 \cdot Hex_1 \cdot Hep_2 \cdot HexNAc_1 \cdot Kdo_2 \cdot Gly_1$ | | 1105.357 | 1.3 |
| | B-Kdo-CO2 | 1048.335 | $PE_1 \cdot Hex_1 \cdot Hep_2 \cdot HexNAc_1 \cdot Kdo_2$ | | 1048.336 | 0.9 |
| | B-Kdo-CO2 | 1267.408 | $PE_1 \cdot Hex_2 \cdot Hep_2 \cdot HexNAc_1 \cdot Kdo_2 \cdot Gly_1$ | | 1267.410 | 1.8 |
| | B-Kdo-CO2 | 1210.387 | $PE_1 \cdot Hex_2 \cdot Hep_2 \cdot HexNAc_1 \cdot Kdo_2$ | | 1210.389 | 1.5 |
| | Y | 1856.941 | | $P_3 \cdot PE_2 \cdot HexN_2 \cdot C12_1 \cdot C12OH_2 \cdot C14OH_2$ | 1856.942 | 0.4 |
| | Y | 1733.932 | | $P_3 \cdot PE_1 \cdot HexN_2 \cdot C12_1 \cdot C12OH_2 \cdot C14OH_2$ | 1733.933 | 0.7 |
| | Y-P | 1653.965 | | $P_3 \cdot PE_1 \cdot HexN_2 \cdot C12_1 \cdot C12OH_2 \cdot C14OH_2$ | 1653.967 | 1.2 |
| | Y-2P-H2O | 1555.988 | | $P_3 \cdot PE_1 \cdot HexN_2 \cdot C12_1 \cdot C12OH_2 \cdot C14OH_2$ | 1555.990 | 1.3 |
| | Y | 2093.153 | | $P_3 \cdot PE_2 \cdot HexN_2 \cdot C12_1 \cdot C12OH_2 \cdot C14OH_2 \cdot C16{:}1_1$ | 2093.156 | 1.4 |
| | Y | 1970.147 | | $P_3 \cdot PE_1 \cdot HexN_2 \cdot C12_1 \cdot C12OH_2 \cdot C14OH_2 \cdot C16{:}1_1$ | 1970.147 | 0.2 |
| | Y-P | 1890.182 | | $P_3 \cdot PE_1 \cdot HexN_2 \cdot C12_1 \cdot C12OH_2 \cdot C14OH_2 \cdot C16{:}1_1$ | 1890.181 | 0.5 |
| | Y-2P-H2O | 1792.202 | | $P_3 \cdot PE_1 \cdot HexN_2 \cdot C12_1 \cdot C12OH_2 \cdot C14OH_2 \cdot C16{:}1_1$ | 1792.204 | 1.2 |
| ΔlpxL1-LpxP 25° C. | B | 1369.404 | $PE_1 \cdot Hex_1 \cdot Hep_2 \cdot HexNAc_1 \cdot Kdo_2 \cdot Gly_1$ | | 1369.406 | 1.1 |
| | B | 1312.379 | $PE_1 \cdot Hex_1 \cdot Hep_2 \cdot HexNAc_1 \cdot Kdo_2$ | | 1312.384 | 3.9 |
| | B-Kdo-CO2 | 1105.356 | $PE_1 \cdot Hex_1 \cdot Hep_2 \cdot HexNAc_1 \cdot Kdo_2 \cdot Gly_1$ | | 1105.357 | 1.3 |
| | B-Kdo-CO2 | 1048.335 | $PE_1 \cdot Hex_1 \cdot Hep_2 \cdot HexNAc_1 \cdot Kdo_2$ | | 1048.336 | 0.9 |
| | B-Kdo-CO2 | 1267.409 | $PE_1 \cdot Hex_2 \cdot Hep_2 \cdot HexNAc_1 \cdot Kdo_2 \cdot Gly_1$ | | 1267.410 | 1.0 |
| | B-Kdo-CO2 | 1210.387 | $PE_1 \cdot Hex_2 \cdot Hep_2 \cdot HexNAc_1 \cdot Kdo_2$ | | 1210.389 | 1.5 |
| | Y | 1856.941 | | $P_3 \cdot PE_2 \cdot HexN_2 \cdot C12_1 \cdot C12OH_2 \cdot C14OH_2$ | 1856.942 | 0.4 |
| | Y | 1733.932 | | $P_3 \cdot PE_1 \cdot HexN_2 \cdot C12_1 \cdot C12OH_2 \cdot C14OH_2$ | 1733.933 | 0.7 |
| | Y-P | 1653.965 | | $P_3 \cdot PE_1 \cdot HexN_2 \cdot C12_1 \cdot C12OH_2 \cdot C14OH_2$ | 1653.967 | 1.2 |
| | Y-2P-H2O | 1555.988 | | $P_3 \cdot PE_1 \cdot HexN_2 \cdot C12_1 \cdot C12OH_2 \cdot C14OH_2$ | 1555.990 | 1.3 |
| | Y | 2093.152 | | $P_3 \cdot PE_2 \cdot HexN_2 \cdot C12_1 \cdot C12OH_2 \cdot C14OH_2 \cdot C16{:}1_1$ | 2093.156 | 1.8 |
| | Y | 1970.147 | | $P_3 \cdot PE_1 \cdot HexN_2 \cdot C12_1 \cdot C12OH_2 \cdot C14OH_2 \cdot C16{:}1_1$ | 1970.147 | 0.2 |
| | Y-P | 1890.18 | | $P_3 \cdot PE_1 \cdot HexN_2 \cdot C12_1 \cdot C12OH_2 \cdot C14OH_2 \cdot C16{:}1_1$ | 1890.181 | 0.5 |
| | Y-2P-H2O | 1792.203 | | $P_3 \cdot PE_1 \cdot HexN_2 \cdot C12_1 \cdot C12OH_2 \cdot C14OH_2 \cdot C16{:}1_1$ | 1792.204 | 0.6 |
| ΔlptA | B | 1369.404 | $PE_1 \cdot Hex_1 \cdot Hep_2 \cdot HexNAc_1 \cdot Kdo_2 \cdot Gly_1$ | | 1369.406 | 1.1 |
| | B | 1312.38 | $PE_1 \cdot Hex_1 \cdot Hep_2 \cdot HexNAc_1 \cdot Kdo_2$ | | 1312.384 | 3.1 |
| | B-Kdo-CO2 | 1105.356 | $PE_1 \cdot Hex_1 \cdot Hep_2 \cdot HexNAc_1 \cdot Kdo_2 \cdot Gly_1$ | | 1105.357 | 1.3 |
| | B-Kdo-CO2 | 1048.335 | $PE_1 \cdot Hex_1 \cdot Hep_2 \cdot HexNAc_1 \cdot Kdo_2$ | | 1048.336 | 0.9 |
| | B-Kdo-CO2 | 1267.408 | $PE_1 \cdot Hex_2 \cdot Hep_2 \cdot HexNAc_1 \cdot Kdo_2 \cdot Gly_1$ | | 1267.410 | 1.8 |
| | B-Kdo-CO2 | 1210.387 | $PE_1 \cdot Hex_2 \cdot Hep_2 \cdot HexNAc_1 \cdot Kdo_2$ | | 1210.389 | 1.5 |
| | Y | 1793.09 | | $P_3 \cdot HexN_2 \cdot C12_2 \cdot C12OH_2 \cdot C14OH_2$ | 1793.092 | 1.0 |
| | Y | 1713.123 | | $P_2 \cdot HexN_2 \cdot C12_2 \cdot C12OH_2 \cdot C14OH_2$ | 1713.125 | 1.5 |
| ΔlptA-ΔlpxL1 | B | 1369.405 | $PE_1 \cdot Hex_1 \cdot Hep_2 \cdot HexNAc_1 \cdot Kdo_2 \cdot Gly_1$ | | 1369.406 | 0.4 |
| | B | 1312.38 | $PE_1 \cdot Hex_1 \cdot Hep_2 \cdot HexNAc_1 \cdot Kdo_2$ | | 1312.384 | 3.1 |
| | B-Kdo-CO2 | 1105.356 | $PE_1 \cdot Hex_1 \cdot Hep_2 \cdot HexNAc_1 \cdot Kdo_2 \cdot Gly_1$ | | 1105.357 | 1.3 |
| | B-Kdo-CO2 | 1048.335 | $PE_1 \cdot Hex_1 \cdot Hep_2 \cdot HexNAc_1 \cdot Kdo_2$ | | 1048.336 | 0.9 |
| | B-Kdo-CO2 | 1267.409 | $PE_1 \cdot Hex_2 \cdot Hep_2 \cdot HexNAc_1 \cdot Kdo_2 \cdot Gly_1$ | | 1267.410 | 1.0 |
| | B-Kdo-CO2 | 1210.388 | $PE_1 \cdot Hex_2 \cdot Hep_2 \cdot HexNAc_1 \cdot Kdo_2$ | | 1210.389 | 0.7 |
| | Y | 1610.923 | | $P_3 \cdot HexN_2 \cdot C12_1 \cdot C12OH_2 \cdot C14OH_2$ | 1610.925 | 1.1 |
| ΔlptA-pagL | B | 1369.404 | $PE_1 \cdot Hex_1 \cdot Hep_2 \cdot HexNAc_1 \cdot Kdo_2 \cdot Gly_1$ | | 1369.406 | 1.1 |
| | B | 1312.382 | $PE_1 \cdot Hex_1 \cdot Hep_2 \cdot HexNAc_1 \cdot Kdo_2$ | | 1312.384 | 1.6 |
| | B-Kdo-CO2 | 1105.356 | $PE_1 \cdot Hex_1 \cdot Hep_2 \cdot HexNAc_1 \cdot Kdo_2 \cdot Gly_1$ | | 1105.357 | 1.3 |
| | B-Kdo-CO2 | 1048.335 | $PE_1 \cdot Hex_1 \cdot Hep_2 \cdot HexNAc_1 \cdot Kdo_2$ | | 1048.336 | 0.9 |
| | B-Kdo-CO2 | 1267.409 | $PE_1 \cdot Hex_2 \cdot Hep_2 \cdot HexNAc_1 \cdot Kdo_2 \cdot Gly_1$ | | 1267.410 | 1.0 |
| | B-Kdo-CO2 | 1210.387 | $PE_1 \cdot Hex_2 \cdot Hep_2 \cdot HexNAc_1 \cdot Kdo_2$ | | 1210.389 | 1.5 |
| | Y | 1594.928 | | $P_3 \cdot HexN_2 \cdot C12_2 \cdot C12OH_1 \cdot C14OH_2$ | 1594.930 | 1.2 |
| | Y | 1514.961 | | $P_2 \cdot HexN_2 \cdot C12_2 \cdot C12OH_1 \cdot C14OH_2$ | 1514.964 | 1.7 |
| | Y | 1793.092 | | $P_3 \cdot HexN_2 \cdot C12_2 \cdot C12OH_2 \cdot C14OH_2$ | 1793.092 | 0.1 |
| | Y | 1713.125 | | $P_2 \cdot HexN_2 \cdot C12_2 \cdot C12OH_2 \cdot C14OH_2$ | 1713.125 | 0.3 |

SUPPLEMENTAL TABLE 2-continued

Proposed compositions for charge-deconvoluted fragment ion peaks obtained by in-source collision-induced dissociation ESI-FT MS of LOS.

| Bacteria | Fragment ion type[a] | Measured mass (u) | Proposed LOS composition Oligosaccharide | Lipid A | Calculated mass (u) | Deviation (ppm) |
|---|---|---|---|---|---|---|
| ΔlptA- | B | 1369.404 | $PE_1 \cdot Hex_1 \cdot Hep_2 \cdot HexNAc_1 \cdot Kdo_2 \cdot Gly_1$ | | 1369.406 | 1.1 |
| LpxE | B | 1312.382 | $PE_1 \cdot Hex_1 \cdot Hep_2 \cdot HexNAc_1 \cdot Kdo_2$ | | 1312.384 | 1.6 |
| | B | 1474.436 | $PE_1 \cdot Hex_2 \cdot Hep_2 \cdot HexNAc_1 \cdot Kdo_2$ | | 1474.437 | 0.6 |
| | B-Kdo-CO2 | 1105.355 | $PE_1 \cdot Hex_1 \cdot Hep_2 \cdot HexNAc_1 \cdot Kdo_2 \cdot Gly_1$ | | 1105.357 | 2.2 |
| | B-Kdo-CO2 | 1048.335 | $PE_1 \cdot Hex_1 \cdot Hep_2 \cdot HexNAc_1 \cdot Kdo_2$ | | 1048.336 | 0.9 |
| | B-Kdo-CO2 | 1210.387 | $PE_1 \cdot Hex_2 \cdot Hep_2 \cdot HexNAc_1 \cdot Kdo_2$ | | 1210.389 | 1.5 |
| | Y | 1713.124 | | $P_2 \cdot HexN_2 \cdot C12_2 \cdot C12OH_2 \cdot C14OH_2$ | 1713.125 | 0.9 |

In-source collision-induced dissociation of LOS produced B- and Y-type fragment ions corresponding to oligosaccharide and lipid A domains due to the rupture of the glycosidic bond between Kdo and lipid A. Fragment ions are assigned according to the nomenclature of Domon and Costello (24). Mass numbers given refer to monoisotopic masses of the neutral molecules.

Abbreviations:
Kdo, 3-deoxy-D-manno-oct-2-ulosonic acid;
Hep, L-glycero-D-manno-heptose;
Hex, hexose;
HexNAc, N-acetylhexosamine;
Gly, glycine;
PEA, phosphoethanolamine;
P, phosphate;
C12OH, 3-hydroxy-dodecanoic acid;
C14OH, 3-hydroxy-tetradecanoic acid;
C12, dodecanoic acid;
C16:1, 9-hexadece

REFERENCES

1. Aderem, A., and Ulevitch, R. J. (2000) Toll-like receptors in the induction of the innate immune response. *Nature* 406, 782-787
2. Loppnow, H., Brade, H., Durrbaum, I., Dinarello, C. A., Kusumoto, S., Rietschel, E. T., and Flad, H. D. (1989) IL-1 induction-capacity of defined lipopolysaccharide partial structures. *Journal of immunology* 142, 3229-3238
3. Zariri, A., and van der Ley, P. (2015) Biosynthetically engineered lipopolysaccharide as vaccine adjuvant. *Expert review of vaccines* 14, 861-876
4. Akira, S., and Takeda, K. (2004) Toll-like receptor signalling. *Nature reviews. Immunology* 4, 499-511
5. Raetz, C. R., and Whitfield, C. (2002) Lipopolysaccharide endotoxins. *Annual review of biochemistry* 71, 635-700
6. Salomao, R., Brunialti, M. K., Rapozo, M. M., Baggio-Zappia, G. L., Galanos, C., and Freudenberg, M. (2012) Bacterial sensing, cell signalling, and modulation of the immune response during sepsis. *Shock* 38, 227-242
7. Park, B. S., Song, D. H., Kim, H. M., Choi, B. S., Lee, H., and Lee, J. O. (2009) The structural basis of lipopolysaccharide recognition by the TLR4-MD-2 complex. *Nature* 458, 1191-1195
8. Raetz, C. R., Reynolds, C. M., Trent, M. S., and Bishop, R. E. (2007) Lipid A modification systems in gram-negative bacteria. *Annual review of biochemistry* 76, 295-329
9. Ohto, U., Fukase, K., Miyake, K., and Shimizu, T. (2012) Structural basis of species-specific endotoxin sensing by innate immune receptor TLR4/MD-2. *Proceedings of the National Academy of Sciences of the United States of America* 109, 7421-7426
10. Gandhapudi, S. K., Chilton, P. M., and Mitchell, T. C. (2013) TRIF is required for TLR4 mediated adjuvant effects on T cell clonal expansion. *PloS one* 8, e56855
11. Mata-Haro, V., Cekic, C., Martin, M., Chilton, P. M., Casella, C. R., and Mitchell, T. C. (2007) The vaccine adjuvant monophosphoryl lipid A as a TRIF-biased agonist of TLR4. *Science* 316, 1628-1632
12. Casella, C. R., and Mitchell, T. C. (2008) Putting endotoxin to work for us: monophosphoryl lipid A as a safe and effective vaccine adjuvant. *Cellular and molecular life sciences:CMLS* 65, 3231-3240
13. Pupo, E., Hamstra, H. J., Meiring, H., and van der Ley, P. (2014) Lipopolysaccharide engineering in *Neisseria meningitidis*: structural analysis of different pentaacyl lipid A mutants and comparison of their modified agonist properties. *The Journal of biological chemistry* 289, 8668-8680
14. Zughaier, S. M., Lindner, B., Howe, J., Garidel, P., Koch, M. H., Brandenburg, K., and Stephens, D. S. (2007) Physicochemical characterization and biological activity of lipooligosaccharides and lipid A from *Neisseria meningitidis*. *Journal of endotoxin research* 13, 343-357
15. van der Ley, P., Steeghs, L., Hamstra, H. J., ten Hove, J., Zomer, B., and van Alphen, L. (2001) Modification of lipid A biosynthesis in *Neisseria meningitidis* lpxL mutants: influence on lipopolysaccharide structure, toxicity, and adjuvant activity. *Infection and immunity* 69, 5981-5990
16. van de Waterbeemd, B., Streefland, M., van der Ley, P., Zomer, B., van Dijken, H., Martens, D., Wijffels, R., and van der Pol, L. (2010) Improved OMV vaccine against *Neisseria meningitidis* using genetically engineered strains and a detergent-free purification process. *Vaccine* 28, 4810-4816
17. Steeghs, L., Keestra, A. M., van Mourik, A., Uronen-Hansson, H., van der Ley, P., Callard, R., Klein, N., and van Putten, J. P. (2008) Differential activation of human and mouse Toll-like receptor 4 by the adjuvant candidate LpxL1 of *Neisseria meningitidis*. *Infection and immunity* 76, 3801-3807
18. Geurtsen, J., Steeghs, L., Hamstra, H. J., Ten Hove, J., de Haan, A., Kuipers, B., Tommassen, J., and van der Ley, P. (2006) Expression of the lipopolysaccharide-modifying enzymes PagP and PagL modulates the endotoxic activity of *Bordetella pertussis*. *Infection and immunity* 74, 5574-5585
19. Westphal, O., and Jann, K. (1965) Bacterial lipopolysaccharides. Extraction with phenol-water and further applications of the procedure in *Methods in Carbohydrate Chemistry* (Whistler, R. L., and Wolfan, M. L. eds.), Academic Press, Inc., New York. pp 83-91
20. Karkhanis, Y. D., Zeltner, J. Y., Jackson, J. J., and Carlo, D. J. (1978) A new and improved microassay to determine 2-keto-3-deoxyoctonate in lipopolysaccharide of Gram-negative bacteria. *Analytical biochemistry* 85, 595-601
21. Tsai, C. M., and Frasch, C. E. (1982) A sensitive silver stain for detecting lipopolysaccharides in polyacrylamide gels. *Analytical biochemistry* 119, 115-119
22. Kondakov, A., and Lindner, B. (2005) Structural characterization of complex bacterial glycolipids by Fourier transform mass spectrometry. *European journal of mass spectrometry* 11, 535-546
23. Wilm, M. S., and Mann, M. (1994) Electrospray and Taylor-Cone theory, Dole's beam of macromolecules at last? *Int J Mass Spectrom Ion Proc* 136, 167-180
24. Domon, B., and Costello, C. E. (1988) A Systematic Nomenclature for Carbohydrate Fragmentations in FAB-MS/MS Spectra of Glycoconjugates. *Glycoconjugate J* 5, 397-409
25. Pavliak, V., Brisson, J. R., Michon, F., Uhrin, D., and Jennings, H. J. (1993) Structure of the sialylated L3 lipopolysaccharide of *Neisseria meningitidis*. The Journal of biological chemistry 268, 14146-14152
26. van der Ley, P., Kramer, M., Martin, A., Richards, J. C., and Poolman, J. T. (1997) Analysis of the icsBA locus required for biosynthesis of the inner core region from *Neisseria meningitidis* lipopolysaccharide. *FEMS microbiology letters* 146, 247-253
27. Carty, S. M., Sreekumar, K. R., and Raetz, C. R. (1999) Effect of cold shock on lipid A biosynthesis in *Escherichia coli*. Induction At 12 degrees C. of an acyltransferase specific for palmitoleoyl-acyl carrier protein. *The Journal of biological chemistry* 274, 9677-9685
28. Golenbock, D. T., Hampton, R. Y., Qureshi, N., Takayama, K., and Raetz, C. R. (1991) Lipid A-like molecules that antagonize the effects of endotoxins on human monocytes. *The Journal of biological chemistry* 266, 19490-19498
29. Findlow, J., Borrow, R., Snape, M. D., Dawson, T., Holland, A., John, T. M., Evans, A., Telford, K. L., Ypma, E., Toneatto, D., Oster, P., Miller, E., and Pollard, A. J. (2010) Multicenter, open-label, randomized phase II controlled trial of an investigational recombinant Meningococcal serogroup B vaccine with and without outer membrane vesicles, administered in infancy. *Clinical infectious diseases: an official publication of the Infectious Diseases Society of America* 51, 1127-1137
30. Snape, M. D., Dawson, T., Oster, P., Evans, A., John, T. M., Ohene-Kena, B., Findlow, J., Yu, L. M., Borrow, R., Ypma, E., Toneatto, D., and Pollard, A. J. (2010) Immunogenicity of two investigational serogroup B meningococcal vaccines in the first year of life: a randomized comparative trial. *The Pediatric infectious disease journal* 29, e71-79
31. Keiser, P. B., Biggs-Cicatelli, S., Moran, E. E., Schmiel, D. H., Pinto, V. B., Burden, R. E., Miller, L. B., Moon, J. E., Bowden, R. A., Cummings, J. F., and Zollinger, W. D. (2011) A phase 1 study of a meningococcal native outer membrane vesicle vaccine made from a group B strain with deleted lpxL1 and synX, over-expressed factor H binding protein, two PorAs and stabilized OpcA expression. *Vaccine* 29, 1413-1420
32. Needham, B. D., Carroll, S. M., Giles, D. K., Georgiou, G., Whiteley, M., and Trent, M. S. (2013) Modulating the innate immune response by combinatorial engineering of endotoxin. *Proceedings of the National Academy of Sciences of the United States of America* 110, 1464-1469
33. Wang, X., Karbarz, M. J., McGrath, S. C., Cotter, R. J., and Raetz, C. R. (2004) MsbA transporter-dependent lipid A 1-dephosphorylation on the periplasmic surface of the inner membrane: topography of francisella novicida LpxE expressed in *Escherichia coli*. *The Journal of biological chemistry* 279, 49470-49478
34. John, C. M., Liu, M., Phillips, N. J., Yang, Z., Funk, C. R., Zimmerman, L. I., Griffiss, J. M., Stein, D. C., and Jarvis, G. A. (2012) Lack of lipid A pyrophosphorylation and functional lptA reduces inflammation by Neisseria commensals. *Infection and immunity* 80, 4014-4026
35. Michaud, J. P., Halle, M., Lampron, A., Theriault, P., Prefontaine, P., Filali, M., Tribout-Jover, P., Lanteigne, A. M., Jodoin, R., Cluff, C., Brichard, V., Palmantier, R., Pilorget, A., Larocque, D., and Rivest, S. (2013) Toll-like receptor 4 stimulation with the detoxified ligand monophosphoryl lipid A improves Alzheimer's disease-related pathology. *Proceedings of the National Academy of Sciences of the United States of America* 110, 1941-1946
36. Peri, F., and Piazza, M. (2012) Therapeutic targeting of innate immunity with Toll-like receptor 4 (TLR4) antagonists. *Biotechnology advances* 30, 251-260
37. Adams, S. (2009) Toll-like receptor agonists in cancer therapy. *Immunotherapy* 1, 949-964

The invention claimed is:

1. A composition comprising a mixture of
   i) a neisserial LPS having a hexa-acylated lipid A moiety, wherein the hexa-acylated lipid A moiety is modified as compared to the lipid A moiety of a wild-type neisserial LPS in that it has a palmitoleoyl (instead of a lauroyl) as secondary acyl chain bound to the primary acyl chain on the glucosamine at the non-reducing end of the lipid A moiety; and
   ii) a neisserial LPS with a penta-acylated lipid A moiety wherein the penta-acylated lipid A moiety is modified as compared to the lipid A moiety of a wild-type neisserial LPS in that it lacks the secondary acyl chain bound to the primary acyl chain on the glucosamine at the non-reducing end of the lipid A moiety.

2. The composition of claim 1, wherein the hexa-acylated neisserial LPS, except for the hexa-acylated lipid A moiety, has the structure of an LPS of *Neisseria meningitidis*, *Neisseria gonorrhoeae* or *Neisseria lactamica*.

3. The composition of claim 1, wherein the hexa-acylated neisserial LPS, except for the hexa-acylated lipid A moiety, hard the structure of an LPS of a genetically modified *Neisseria meningitidis*, *Neisseria gonorrhoeae* or *Neisseria lactamica* that is at least one of lgtB⁻ and galE⁻.

4. The composition of claim 1, wherein the hexa-acylated lipid A moiety has the structure of formula (I):

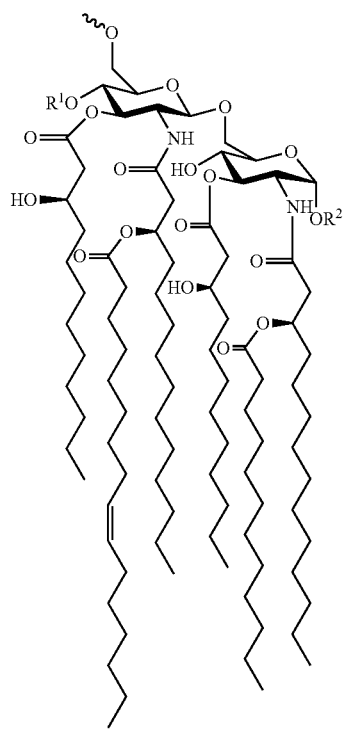

(I)

wherein $R_1$ and $R_2$, independently, are either —P(O)(OH)$_2$, —[P(O)(OH)—O]$_2$—H, —[P(O)(OH)—O]$_2$—CH$_2$CH$_2$NH$_2$, —[P(O)(OH)—O]$_3$—CH$_2$CH$_2$NH$_2$, —[P(O)(OH)—O]$_3$—H or —P(O)(OH)—O—CH$_2$CH$_2$NH$_2$.

5. The composition of claim 1, wherein the penta-acylated neisserial LPS, except for the penta-acylated lipid A moiety, has the structure of an LPS of *Neisseria meningitidis*, *Neisseria gonorrhoeae* or *Neisseria lactamica*.

6. The composition of claim 1, wherein the penta-acylated neisserial LPS, except for the penta-acylated lipid A moiety, has the structure of an LPS of a genetically modified *Neisseria meningitidis*, *Neisseria gonorrhoeae* or *Neisseria lactamica* that is at least one of lgtB⁻ and galE⁻.

7. The composition of claim 1, wherein the penta-acylated lipid A moiety has the structure of formula (II):

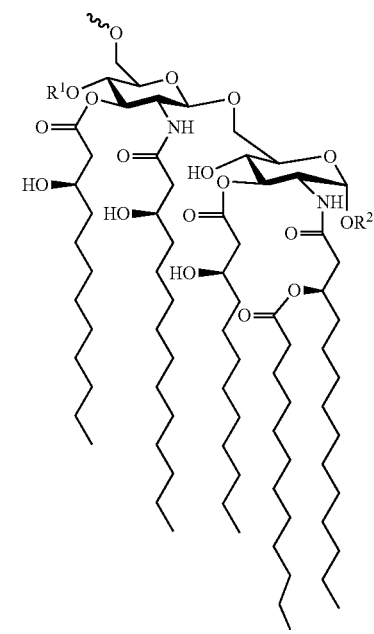

(II)

wherein $R_1$ and $R_2$, independently, are either —P(O)(OH)$_2$, —[P(O)(OH)—O]$_2$—H, —[P(O)(OH)—O]$_2$—CH$_2$CH$_2$NH$_2$, —[P(O)(OH)—O]$_3$—CH$_2$CH$_2$NH$_2$, —[P(O)(OH)—O]$_3$—H or —P(O)(OH)—O—CH$_2$CH$_2$NH$_2$.

8. The composition of claim 1, wherein the composition comprises the hexa-acylated neisserial LPS and the penta-acylated neisserial LPS in a molar ratio in the range of 1:400 to 1:1.25.

9. The composition of claim 1, wherein the composition is an acellular vaccine, and wherein the composition optionally further comprises at least one non-neisserial antigen.

10. The composition of claim 1, wherein the composition comprises an outer membrane vesicle (OMV) comprising the mixture of the hexa-acylated neisserial LPS and the penta-acylated neisserial LPS.

11. The composition of claim 10, wherein the composition is an acellular vaccine and wherein the composition optionally further comprises at least one non-neisserial antigen.

12. The composition of claim 1, wherein the composition comprises a genetically modified bacterium comprising the mixture of the hexa-acylated neisserial LPS and the penta-acylated neisserial LPS, wherein the genetically modified bacterium is a bacterium of the genus *Neisseria*, and wherein the bacterium comprises:
 a) a genetic modification that eliminates the activity of a lipid A biosynthesis lauroyl acyltransferase encoded by an endogenous lpxL1 gene; and,
 b) a genetic modification that confers to the bacterium lipid A biosynthesis palmitoleoyltransferase activity, wherein the genetic modification introduces the expression of an LpxP lipid A palmitoleyltransferase that has at least 95% amino acid sequence identity with SEQ ID NO: 4.

13. The composition of claim 12, wherein the composition is a whole cell vaccine and wherein the composition optionally further comprises at least one non-neisserial antigen.

14. A process for producing the composition of claim 1, wherein the process comprises the steps of:
 a) cultivating a genetically modified bacterium of the genus *Neisseria* at a temperature in the range of 20-42° C., wherein the bacterium comprises:
  i) a genetic modification that eliminates the activity of a lipid A biosynthesis lauroyl acyltransferase encoded by an endogenous lpxL1 gene; and,
  ii) a genetic modification that confers to the bacterium lipid A biosynthesis palmitoleoyltransferase activity, wherein the genetic modification introduces the expression of an LpxP lipid A palmitoleoytransferase that has at least 95% amino acid sequence identity with SEQ ID No: 4; and,
 b) optionally, at least one of extraction and purification of the mixture of LPSs.

15. The process of claim 14, wherein the bacterium is a genetically modified *Neisseria meningitidis, Neisseria gonorrhoeae* or *Neisseria lactamica*.

16. The process of claim 14, wherein:
 the endogenous lxL1 gene is a gene encoding an LpxL1 protein having an amino acid sequence with at least 90% sequence identity with at least one of SEQ ID NO's: 1-3.

17. A process for producing the composition of claim 10, wherein the process comprises the steps of:
 a) cultivating a genetically modified bacterium of the genus *Neisseria* at a temperature in the range of 20-42° C., wherein the bacterium comprises:
  i) a genetic modification that eliminates the activity of a lipid A biosynthesis lauroyl acyltransferase encoded by an endogenous lpxL1 gene; and,
  ii) a genetic modification that confers to the bacterium lipid A biosynthesis palmitoleoyltransferase activity, wherein the genetic modification introduces the expression of an LpxP lipid A palmitoleoyltransferase that has at least 95% amino acid sequence identity with SEQ ID NO: 4; and,
 b) optionally, extracting the OMV; and,
 c) recovering the OMV, wherein the recovery at least comprises removal of the bacteria from the OMV.

18. The process of claim 17, wherein the process is a detergent-free process.

19. The process of claim 14, wherein in step a) the bacterium is cultured at a temperature lower than 37° C.

20. The process of claim 17, wherein in step a) the bacterium is cultured at a temperature lower than 37° C.

* * * * *